US010597649B2

(12) United States Patent
Moe et al.

(10) Patent No.: US 10,597,649 B2
(45) Date of Patent: *Mar. 24, 2020

(54) TAU PROTEASE COMPOSITIONS AND METHODS OF USE

(71) Applicant: Oligomerix, Inc., New York, NY (US)

(72) Inventors: James G. Moe, Stamford, CT (US); Eliot J. Davidowitz, West Hempstead, NY (US); Patricia Lopez, East Elmhurst, NY (US)

(73) Assignee: Oligomerix, Inc., Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/358,984

(22) Filed: Nov. 22, 2016

(65) Prior Publication Data

US 2017/0198273 A1 Jul. 13, 2017

Related U.S. Application Data

(63) Continuation of application No. 14/119,154, filed as application No. PCT/US2012/038672 on May 18, 2012, now Pat. No. 9,506,051.

(60) Provisional application No. 61/488,493, filed on May 20, 2011, provisional application No. 61/544,090, filed on Oct. 6, 2011, provisional application No. 61/569,558, filed on Dec. 12, 2011.

(51) Int. Cl.
*C12N 9/64* (2006.01)
*C12Q 1/37* (2006.01)
*G01N 33/68* (2006.01)
*A61K 38/48* (2006.01)
*A61K 39/395* (2006.01)
*C07K 16/40* (2006.01)
*G01N 33/573* (2006.01)
*A61K 38/00* (2006.01)

(52) U.S. Cl.
CPC .......... *C12N 9/6424* (2013.01); *A61K 38/482* (2013.01); *A61K 39/3955* (2013.01); *C07K 16/40* (2013.01); *C12Q 1/37* (2013.01); *G01N 33/573* (2013.01); *G01N 33/6896* (2013.01); *A61K 38/00* (2013.01); *G01N 2800/2821* (2013.01)

(58) Field of Classification Search
None
See application file for complete search history.

(56) References Cited

U.S. PATENT DOCUMENTS

| 6,200,768 | B1 | 3/2001 | Mandelkow et al. |
| 7,834,237 | B2 | 11/2010 | Wischik et al. |
| 9,161,520 | B2 | 10/2015 | Kontsekova |
| 2002/0168687 | A1* | 11/2002 | Wischik ............... A61K 31/54 435/7.1 |
| 2002/0188106 | A1 | 12/2002 | Mandelkow et al. |
| 2005/0009019 | A1* | 1/2005 | Van Lueven ...... C07K 14/4711 435/6.13 |
| 2007/0218491 | A1 | 9/2007 | Vasan et al. |
| 2008/0220449 | A1 | 9/2008 | Vasan et al. |
| 2010/0112602 | A1* | 5/2010 | Taylor ................ C07K 14/4738 435/7.21 |
| 2015/0183854 | A1* | 7/2015 | Mori ..................... C07K 16/18 424/133.1 |

FOREIGN PATENT DOCUMENTS

| JP | 2004-531224 A | 10/2004 |
| JP | 2006-515270 A | 5/2006 |
| WO | 2002059150 A2 | 8/2002 |
| WO | 2004007547 A2 | 1/2004 |
| WO | 2009000520 A1 | 12/2008 |
| WO | 10021755 A2 | 2/2010 |
| WO | 2010021755 A2 | 2/2010 |
| WO | 13004717 A1 | 1/2013 |

OTHER PUBLICATIONS

Clavaguera 2009 "transmission and spreading of tauopathy in transgenic mouse brain" Nat Cell Biol 11(7):909-913.*
Davies 2005 "FKBP52" IJBCB 37:42-47.*
Kirsch 2000 "BMP-2 antagonists emerge from alterations in the low-affinity binding epitope for receptor BMPR-II" EMBO 19(13):3314-3324.*
Friedhoff, P., et al. "A nucleated assembly mechanism of Alzheimer paired helical filaments," Proc. Natl. Acad. Sci. USA, vol. 95, pp. 15712-15717, Dec. 1998.
Funk, Kristen E., et al. "Lysine methylation is an endogenous post-translational modification of tau protein in human brain and a modulator of aggregation propensity," Biochem. J. (2014) 462, 77-88.
Iqbal, Khalid, et al. "Hyperphosphorylation-induced tau oligomers," Frontiers in Neurology. Aug. 2013, vol. 4, Article 112.
Martin, Ludovic, et al. "Post-translational modifications of tau protein: Implications for Alzheimer's disease," Neurochemistry International, 58 (2011) 458-471.
Mietelska-Porowska, Anna, et al. "Tau Protein Modifications and Interactions: Their Role in Function and Dysfunction," Int. J. Mol. Sci., 2014, 15, 4671-4713.
Tian, Huilai, et al. "Trimeric Tau Is Toxic to Human Neuronal Cells at Low Nanomolar Concentrations," International Journal of Cell Biology, vol. 2013, Article ID 260787, 9 pages, Hindawi Publishing Corp.
Tian, Huilai, et al. "Isolation and characterization of antibody fragments selective for toxic oligomeric tau," Neurobiology of Aging, 36 (2015) 1342-1355.
Bhattacharya, et al., Biochem. Biophys. Res. Comm., vol. 285, pp. 20-26, 2001.

(Continued)

Primary Examiner — Adam Weidner
(74) Attorney, Agent, or Firm — Sorell, Lenna & Schmidt LLP; William D. Schmidt, Esq.

(57) ABSTRACT

Disclosed are mammalian tau proteases, as well as proteolytically-active fragments, variants, and mutants thereof. Also disclosed are polynucleotides and recombinant expression vectors that encode these polypeptides, as well as methods for producing such proteins in selected recombinant host cells, and for using the compositions in a variety of diagnostic and analytical assays.

16 Claims, 31 Drawing Sheets
Specification includes a Sequence Listing.

(56) References Cited

OTHER PUBLICATIONS

Ruben, et al. JBC, vol. 266, 1991, pp. 22019-22027.
Carrell, et al. a1-Antitrypsin and the serpins: Variation and countervariation, Trends Biochem. Sci. (1985) 10:20-24.
A_Geneseq_201314 database Acc#ATS01478 from Grossman et al US2008241840. Alignment with SEQ ID No. 5.
AEBSF from Sigma, Inc. Downloaded Dec. 16, 2014.
Arai, et al. "Proteolysis of non-phosphorylated and phosphorylated tau by thrombin" J. Biol. Chem. Feb. 18, 2005; 280(7): 5145-53.
GenEmbl database Acc#AY730549 from Chun et al., 2004 direct submission. Alignment with SEQ ID No. 5.
Gamblin et al. "Caspase cleavage of tau: Linking amyloid and neurofibrillary tangles in Alzheimer's Disease." 10032-10037_PNAS_Aug. 19, 2003_vol. 100_No. 17.
Yao, et al. Aggregation Analysis of the Microtubule Binding Domain in Tau Protein by Spectroscopic Methods. J. Biochem. 134, 91-99 (2003).
Neumann, et al. Pick's Disease associated with the novel Tau gene mutation K3691. Ann Neurology Oct. 2001 vol. 50 No. 4 pp. 503-513. Abstract.
International Search Report of the International Searching Authority, dated Sep. 21, 2012, of International Application No. PCT/US12/38672, filed Aug. 18, 2012.
Extended European Search Report issued by the European Patent Office, dated Dec. 18, 2014, of European Patent Application No. EP 12 79 0384.7.
International Search Report of the International Searching Authority, dated Apr. 29, 2010, of International Application No. PCT/US09/04796, filed Aug. 20, 2009.
Later publication of International Search Report of the International Searching Authority, dated Apr. 29, 2010, of International Application No. PCT/US09/04796, filed Aug. 20, 2009, as published in WO 2010/021755 A3 on Jun. 24, 2010.
International Preliminary Report on Patentability (Chapter I) issued by the International Bureau of WIPO on Feb. 22, 2011 in International Application No. PCT/US2009/004796, filed Aug. 20, 2009.
International Preliminary Report on Patentability (Chapter 1) issued by the International Bureau of WIPO on Nov. 20, 2013 in International Application No. PCT/US2012/038672, filed May 18, 2012.
Written Opinion of the International Searching Authority, dated Apr. 29, 2010, of International Application No. PCT/US09/04796 filed on Aug. 20, 2009.
Supplementary European Search Report by the European Patent Office, Munich, of European Patent Application No. EP 12790384 (Applicant: James G. Moe) dated Dec. 18, 2014.
Abstract—Neumann et al. Pick's disease associated with the novel Tau gene mutation K3691. Ann Neurology Oct. 2001 vol. 50 No. 4 pp. 503-513. Especially p. 508 fig 5b.
PCT/US2012/038672 Written Opinion of the International Search Authority dated Sep. 21, 2012.

* cited by examiner

✗ TAU PROTEASE BLOCKS THIS STEP IN APP PROCESSING BY CLEAVING AT KS AND KM SITES AMONG OTHERS IN APP

↑ TAU PROTEASE ENHANCES OR ACTIVATES THIS STEP IN Aβ (1-42) PRODUCTION BY CUTTING AT KM GENERATING Aβ (-1-42) AND STIMULATING INFLAMATION THAT LEANS TO BACE EXPRESSION THEREBY ACTIVATING THE AMYLOID CASCADE IN AD

```
  1 ATGAGCAAAGACGGTACTGGTAGCGACGACAAAAAAGCAAAAGGT
    M   S   K   D   G   T   G   S   D   D   K   K   A   K   G
 46 GCTGATGGTAAAACCAAGATCGCAACCCCGCGTGGTGCAGCACCG
    A   D   G   K   T   K   I   A   T   P   R   G   A   A   P
 91 CCGGGCCAGAAAGGCCAGGCCAACGCCACCCGTATTCCGGCAAAA
    P   G   Q   K   G   Q   A   N   A   T   R   I   P   A   K
136 ACCCCGCCGGCTCCGAAAACCCCGCCGAGCTCTGGTGAACCGCCG
    T   P   P   A   P   K   T   P   P   S   S   G   E   P   P
181 AAATCTGGTGACCGTAGCGGCTACAGCAGCCCGGGCTCTCCGGGC
    K   S   G   D   R   S   G   Y   S   S   P   G   S   P   G
226 ACTCCGGGCAGCCGTTCTCGTACCCCGTCTCTTCCGACCCCGCCG
    T   P   G   S   R   S   R   T   P   S   L   P   T   P   P
271 ACCCGTGAACCGAAAAAGGTTGCAGTGGTCCGTACTCCGCCGAAA
    T   R   E   P   K   K   V   A   V   V   R   T   P   P   K
316 TCTCCGTCTTCTGCAAAGAGCCGTCTGCAGACCGCACCGGTTCCG
    S   P   S   S   A   K   S   R   L   Q   T   A   P   V   P
361 ATGCCGGACCTGAAAAATGTTAAATCTAAGATCGGCTCTACTGAA
    M   P   D   L   K   N   V   K   S   K   I   G   S   T   E
406 AACCTGAAACACCAGCCGGGTGGCGGTAAAGTTCAGATCATTAAT
    N   L   K   H   Q   P   G   G   G   K   V   Q   I   I   N
451 AAGAAACTGGACCTTAGCAACGTTCAGTCTAAATGTGGCTCTAAG
    K   K   L   D   L   S   N   V   Q   S   K   C   G   S   K
496 GACAATATCAAACACGTTCCGGGTGGCGGCTCTGTTCAAATCGTT
    D   N   I   K   H   V   P   G   G   G   S   V   Q   I   V
541 TACAAACCGGTTGACCTGAGCAAAGTTACCTCTAAGTGTGGCTCT
    Y   K   P   V   D   L   S   K   V   T   S   K   C   G   S
586 TTAGGCAACATCCATCATAAACCGGGTGGTGGCCAGGTTGAAGTA
    L   G   N   I   H   H   K   P   G   G   G   Q   V   E   V
631 AAATAG 636
    K
```

TP-210
SEQ ID NO:7 (NUCLEIC ACID)
AND SEQ ID NO:1 (AMINO ACID)

FIG. 19

```
  1 ATGCGTCTCCAGACCGCACCGGTTCCGATGCCGGACCTQAAAAAT
    M  R  L  Q  T  A  P  V  D  M  P  D  L  K  M
 46 GTTAAATCTAAGATCGGCTCTACTGAAAACCTGAAACACCAGCCG
    V  K  S  K  I  Q  S  T  E  N  L  K  M  Q  P
 81 GGTGGCGGTAAAGTTCAGATCATTAATAAGAAACTGGACCTTAGC
    G  C  G  K  V  Q  I  I  N  K  K  L  D  L  S
136 AACGTTCAGTCTAAATGTGGCTCTAAGGACAATATCAAACACGTT
    N  V  Q  S  K  C  G  S  K  D  N  I  K  H  V
181 CCGGGTGGCGGCTCTGTTCAAATCGTTACAAACCGGTTGACCTG
    P  G  G  G  S  V  Q  J  V  Y  K  P  V  D  L
226 AGCAAAGTTACCTCTAAGTGTGGCTCTTTAQGCAACATCCATCAT
    S  K  V  T  S  K  C  G  S  L  G  N  I  H  H
271 AAACCGCGTGGTGGCCAGGTTGAAGTAAAATAG   303
    K  P  G  G  G  Q  V  E  V  K  *
```

TP-99

SEQ ID NO:9 (NUCLEIC ACID) AND SEQ ID NO:3 (AMINO ACID)

FIG. 20

```
GROWTH & INDUCTION IN BL21 DB3 E.COLI CELLS
                    ⇩
CELLS LYSED UNDER REDUCING CONDITIONS WITH DETERGENT/SERINE
PROTEASE INHIBITORS & SONICATION (NO LYSOZYME USED)
                    ⇩
INCLUSION BODY EXTRACTED USING CELLYTIC B FOLLOWED
BY DESALTING/BUFFER EXCHANGE INTO 25 mM Tris-HCl pH 7.4
                    ⇩
INCLUSION BODY EXTRACT PURIFIED BY CONTINUOUS ELUTION ELECTROPHORESIS,
TP-210 MONOMER POOLED AND BUFFER EXCHANGED INTO 25 mM Tris-HCl pH 7.4
                    ⇩
OLIGOMERIZATION PERFORMED AT 37°C FOR 24 HOURS
                    ⇩
OLIGOMER PURIFIED BY CONTINUOUS ELUTION ELECTROPHORESIS
```

FIG. 21

MLPGLALLLLAAWTARALEVPTDGNAGLLAEPQIAMFCGRLNMHMNVQNGKWDSDPSGTKTCIDTKEGIL

QYCQEVYPELQITNVVEANQPVTIQNWCKRGRKQCKTHPHFVIPYRCLVGEFVSDALLVPDKCKFLHQER

MDVCETHLHWHTVAKETCSEKSTNLHDYGMLLPCGIDKFRGVEFVCCPLAEESDNVDSADAEEDDSDVWW

GGADTDYADGSEDKVVEVAEEEEVAEVEEEEADDDEDDEDGDEVEEEAEEPYEEATERTTSIATTTTTTT

ESVEEVVREVCSEQAETGPCARMISRWYFDVTEGKCAPFFYGGCGGNRNNFDTEEYCMAVCGSAMSQSLL

KTTQEPLARDPVKLPTTAASTPDAVDKYLETPGDENEHAHFQKAKERLEAKHRERMSQVMREWEEAERQA

KNLPKADKKAVIQHFQEKVESLEQEAANERQQLVETHMARVEAMLNDRRRLALENYITALQAVPPRPRHV

FNMLKKYVRAEQKDRQHTLKHFEHVRMVDPKKAAQIRSQVMTHLRVIYERMNQSLSLLYNVPAVAEEIQD

EVDELLQKEQNYSDDVLANMISEPRISYGNDALMPSLTETKTTVELLPVNGEFSLDDLQPWHSFGADSVP

ANTENEVEPVDARPAADRGLTTRPGSGLTNIKTEEISEVKMDAEFRHDSGYEVHHQKLVFFAEDVGSNKG

AIIGLMVGGVVIATVIVITLVMLKKKQYTSIHHGVVEVDAAVTPEERHLSKMQQNGYENPTYKFFEQMQN (SEQ ID NO:17)

FIG. 24

SEQUENCE LISTING

```
<160> NUMBER OF SEQ ID NOS: 40

<210> SEQ ID NO 1
<211> LENGTH: 211
<212> TYPE: PRT
<213> ORGANISM: Homo sapiens

<400> SEQUENCE: 1

Met Ser Lys Asp Gly Thr Gly Ser Asp Asp Lys Lys Ala Lys Gly Ala
1               5                   10                  15

Asp Gly Lys Thr Lys Ile Ala Thr Pro Arg Gly Ala Ala Pro Pro Gly
            20                  25                  30

Gln Lys Gly Gln Ala Asn Ala Thr Arg Ile Pro Ala Lys Thr Pro Pro
        35                  40                  45

Ala Pro Lys Thr Pro Ser Ser Gly Glu Pro Pro Lys Ser Gly Asp
    50                  55                  60

Arg Ser Gly Tyr Ser Ser Pro Gly Ser Pro Gly Thr Pro Gly Ser Arg
65                  70                  75                  80

Ser Arg Thr Pro Ser Leu Pro Thr Pro Thr Arg Glu Pro Lys Lys
            85                  90                  95

Val Ala Val Val Arg Thr Pro Pro Lys Ser Pro Ser Ser Ala Lys Ser
            100                 105                 110

Arg Leu Gln Thr Ala Pro Val Pro Met Pro Asp Leu Lys Asn Val Lys
        115                 120                 125

Ser Lys Ile Gly Ser Thr Glu Asn Leu Lys His Gln Pro Gly Gly Gly
    130                 135                 140

Lys Val Gln Ile Ile Asn Lys Lys Leu Asp Leu Ser Asn Val Gln Ser
145                 150                 155                 160

Lys Cys Gly Ser Lys Asp Asn Ile Lys His Val Pro Gly Gly Gly Ser
                165                 170                 175
```

```
Val Gln Ile Val Tyr Lys Pro Val Asp Leu Ser Lys Val Thr Ser Lys
            180                 185                 190

Cys Gly Ser Leu Gly Asn Ile His His Lys Pro Gly Gly Gly Gln Val
        195                 200                 205

Glu Val Lys
    210

<210> SEQ ID NO 2
<211> LENGTH: 119
<212> TYPE: PRT
<213> ORGANISM: Homo sapiens

<400> SEQUENCE: 2

Met His Gln Pro Gly Gly Lys Val Gln Ile Ile Asn Lys Lys Leu
1               5                   10                  15

Asp Leu Ser Asn Val Gln Ser Lys Cys Gly Ser Lys Asp Asn Ile Lys
            20                  25                  30

His Val Pro Gly Gly Gly Ser Val Gln Ile Val Tyr Lys Pro Val Asp
            35                  40                  45

Leu Ser Lys Val Thr Ser Lys Cys Gly Ser Leu Gly Asn Ile His His
    50                  55                  60

Lys Pro Gly Gly Gly Gln Val Glu Val Lys Ser Glu Lys Leu Asp Phe
65                  70                  75                  80

Lys Asp Arg Val Gln Ser Lys Ile Gly Ser Leu Asp Asn Ile Thr His
                85                  90                  95

Val Pro Gly Gly Gly Asn Lys Lys Ile Glu Thr His Lys Leu Thr Phe
            100                 105                 110

Arg Glu Asn Ala Lys Ala Lys
        115

<210> SEQ ID NO 3
<211> LENGTH: 100
<212> TYPE: PRT
<213> ORGANISM: Homo sapiens

<400> SEQUENCE: 3

Met Arg Leu Gln Thr Ala Pro Val Pro Met Pro Asp Leu Lys Asn Val
1               5                   10                  15

Lys Ser Lys Ile Gly Ser Thr Glu Asn Leu Lys His Gln Pro Gly Gly
            20                  25                  30

Gly Lys Val Gln Ile Ile Asn Lys Lys Leu Asp Leu Ser Asn Val Gln
            35                  40                  45

Ser Lys Cys Gly Ser Lys Asp Asn Ile Lys His Val Pro Gly Gly Gly
    50                  55                  60

Ser Val Gln Ile Val Tyr Lys Pro Val Asp Leu Ser Lys Val Thr Ser
65                  70                  75                  80

Lys Cys Gly Ser Leu Gly Asn Ile His His Lys Pro Gly Gly Gly Gln
                85                  90                  95

Val Glu Val Lys
    100

<210> SEQ ID NO 4
<211> LENGTH: 84
<212> TYPE: PRT
<213> ORGANISM: Homo sapiens

<400> SEQUENCE: 4

Met Ser Lys Ile Gly Ser Thr Glu Asn Leu Lys His Gln Pro Gly Gly
```

```
            1               5                   10                  15
        Gly Lys Val Gln Ile Ile Asn Lys Lys Leu Asp Leu Ser Asn Val Gln
                        20                  25                  30

Ser Lys Cys Gly Ser Lys Asp Asn Ile Lys His Val Pro Gly Gly Gly
                        35                  40                  45

Ser Val Gln Ile Val Tyr Lys Pro Val Asp Leu Ser Lys Val Thr Ser
                        50                  55                  60

Lys Cys Gly Ser Leu Gly Asn Ile His His Lys Pro Gly Gly Gly Gln
        65                  70                  75                  80

Val Glu Val Lys
```

```
<210> SEQ ID NO 5
<211> LENGTH: 82
<212> TYPE: PRT
<213> ORGANISM: Homo sapiens

<400> SEQUENCE: 5
```

```
        Met Ile Gly Ser Thr Glu Asn Leu Lys His Gln Pro Gly Gly Gly Lys
        1               5                   10                  15

Val Gln Ile Ile Asn Lys Lys Leu Asp Leu Ser Asn Val Gln Ser Lys
                        20                  25                  30

Cys Gly Ser Lys Asp Asn Ile Lys His Val Pro Gly Gly Gly Ser Val
                        35                  40                  45

Gln Ile Val Tyr Lys Pro Val Asp Leu Ser Lys Val Thr Ser Lys Cys
                        50                  55                  60

Gly Ser Leu Gly Asn Ile His His Lys Pro Gly Gly Gly Gln Val Glu
        65                  70                  75                  80

Val Lys
```

```
<210> SEQ ID NO 6
<211> LENGTH: 440
<212> TYPE: PRT
<213> ORGANISM: Homo sapiens

<400> SEQUENCE: 6
```

```
        Met Ala Glu Pro Arg Gln Glu Phe Glu Val Met Glu Asp His Ala Gly
        1               5                   10                  15

Thr Tyr Gly Leu Gly Asp Arg Lys Asp Gln Gly Gly Tyr Thr Met His
                        20                  25                  30

Gln Asp Gln Glu Gly Asp Thr Asp Ala Gly Leu Lys Glu Ser Pro Leu
                        35                  40                  45

Gln Thr Pro Thr Glu Asp Gly Ser Glu Glu Pro Gly Ser Glu Thr Ser
                        50                  55                  60

Asp Ala Lys Ser Thr Pro Thr Ala Glu Asp Val Thr Ala Pro Leu Val
        65                  70                  75                  80

Asp Glu Gly Ala Pro Gly Lys Gln Ala Ala Gln Pro His Thr Glu
                        85                  90                  95

Ile Pro Glu Gly Thr Thr Ala Glu Glu Ala Gly Ile Gly Asp Thr Pro
                        100                 105                 110

Ser Leu Glu Asp Glu Ala Ala Gly His Val Thr Gln Ala Arg Met Val
                        115                 120                 125

Ser Lys Ser Lys Asp Gly Thr Gly Ser Asp Asp Lys Lys Ala Lys Gly
                        130                 135                 140

Ala Asp Gly Lys Thr Lys Ile Ala Thr Pro Arg Gly Ala Ala Pro Pro
        145                 150                 155                 160
```

```
Gly Gln Lys Gly Gln Ala Asn Ala Thr Arg Ile Pro Ala Lys Thr Pro
            165                 170                 175

Pro Ala Pro Lys Thr Pro Ser Ser Gly Glu Pro Lys Ser Gly
        180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
                340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Trp Ser Gly
385                 390                 395                 400

Asp Thr Ser Pro Arg His Leu Ser Asn Val Ser Ser Thr Gly Ser Ile
                405                 410                 415

Asp Met Val Asp Ser Pro Gln Leu Ala Thr Leu Ala Asp Glu Val Ser
                420                 425                 430

Ala Ser Leu Ala Lys Gln Gly Leu
        435                 440

<210> SEQ ID NO 7
<211> LENGTH: 636
<212> TYPE: DNA
<213> ORGANISM: Homo sapiens

<400> SEQUENCE: 7
atgagcaaag acggtactgg tagcgacgac aaaaaagcaa aggtgctga tggtaaaacc      60 aagatcgcaa ccccgcgtgg tgcagcaccg ccgggccaga aaggccaggc caacgccacc     120
cgtattccgg caaaaacccc gccggctccg aaaacccccgc cgagctctgg tgaaccgccg    180
aaatctggtg accgtagcgg ctacagcagc ccgggctctc cgggcactcc gggcagccgt     240
tctcgtaccc cgtctcttcc gaccccgccg accgtgaac cgaaaaaggt tgcagtggtc     300
cgtactccgc cgaaatctcc gtcttctgca agagccgtc tgcagaccgc accggttccg     360
atgccggacc tgaaaaatgt taaatctaag atcggctcta ctgaaaacct gaaacaccag    420
ccgggtggcg gtaaagttca gatcattaat aagaaactgg accttagcaa cgttcagtct    480
aaatgtggct ctaaggacaa tatcaaacac gttccgggtg gcggctctgt tcaaatcgtt    540
```

```
tacaaaccgg ttgacctgag caaagttacc tctaagtgtg gctctttagg caacatccat    600
cataaaccgg gtggtggcca ggttgaagta aaatag                              636

<210> SEQ ID NO 8
<211> LENGTH: 360
<212> TYPE: DNA
<213> ORGANISM: Homo sapiens

<400> SEQUENCE: 8
atgcaccagc cgggaggcgg gaaggtgcag ataattaata agaagctgga tcttagcaac     60
gtccagtcca agtgtggctc aaaggataat atcaaacacg tcccgggagg cggcagtgtg    120
caaatagtct acaaaccagt tgacctgagc aaggtgacct ccaagtgtgg ctcattaggc    180
aacatccatc ataaaccagg aggtggccag gtggaagtaa aatctgagaa gcttgacttc    240
aaggacagag tccagtcgaa gattgggtcc ctggacaata tcacccacgt ccctggcgga    300
ggaaataaaa agattgaaac ccacaagctg accttccgcg agaacgccaa agccaagtag    360

<210> SEQ ID NO 9
<211> LENGTH: 303
<212> TYPE: DNA
<213> ORGANISM: Homo sapiens

<400> SEQUENCE: 9
atgcgtctgc agaccgcacc ggttccgatg ccggacctga aaatgttaa atctaagatc      60 ggctctactg aaaacctgaa acaccagccg ggtggcggta agttcagat cattaataag    120 aaactggacc ttagcaacgt tcagtctaaa tgtggctcta aggacaatat caaacacgtt    180
ccgggtggcg gctctgttca aatcgtttac aaaccggttg acctgagcaa agttacctct    240
aagtgtggct ctttaggcaa catccatcat aaaccgggtg gtggccaggt tgaagtaaaa    300
tag                                                                  303

<210> SEQ ID NO 10
<211> LENGTH: 255
<212> TYPE: DNA
<213> ORGANISM: Homo sapiens

<400> SEQUENCE: 10
atgtccaaga tcggctccac tgagaacctg aagcaccagc cgggaggcgg gaaggtgcag     60
ataattaata agaagctgga tcttagcaac gtccagtcca agtgtggctc aaaggataat    120
atcaaacacg tcccgggagg cggcagtgtg caaatagtct acaaaccagt tgacctgagc    180
aaggtgacct ccaagtgtgg ctcattaggc aacatccatc ataaaccagg aggtggccag    240
gtggaagtaa aatag                                                     255

<210> SEQ ID NO 11
<211> LENGTH: 249
<212> TYPE: DNA
<213> ORGANISM: Homo sapiens

<400> SEQUENCE: 11
atgatcggct ccactgagaa cctgaagcac cagccgggag gcgggaaggt gcagataatt     60
aataagaagc tggatcttag caacgtccag tccaagtgtg gctcaaagga taatatcaaa    120
cacgtcccgg gaggcggcag tgtgcaaata gtctacaaac cagttgacct gagcaaggtg    180
acctccaagt gtggctcatt aggcaacatc catcataaac caggaggtgg ccaggtggaa    240
``` gtaaaatag                                                                                      249

<210> SEQ ID NO 12
<211> LENGTH: 440
<212> TYPE: PRT
<213> ORGANISM: Homo sapiens

<400> SEQUENCE: 12

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

```
Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Trp Ser Gly
385                 390                 395                 400

Asp Thr Ser Pro Arg His Leu Ser Asn Val Ser Ser Thr Gly Ser Ile
                405                 410                 415

Asp Met Val Asp Ser Pro Gln Leu Ala Thr Leu Ala Asp Glu Val Ser
                420                 425                 430

Ala Ser Leu Ala Lys Gln Gly Leu
        435                 440

<210> SEQ ID NO 13
<211> LENGTH: 16
<212> TYPE: PRT
<213> ORGANISM: Homo sapiens

<400> SEQUENCE: 13

Tyr Gly Gly Phe Met Thr Ser Glu Lys Ser Gln Thr Pro Leu Val Thr
1               5                   10                  15

<210> SEQ ID NO 14
<211> LENGTH: 10
<212> TYPE: PRT
<213> ORGANISM: Homo sapiens

<400> SEQUENCE: 14

Ser Glu Val Lys Met Asp Ala Glu Phe Arg
1               5                   10

<210> SEQ ID NO 15
<211> LENGTH: 9
<212> TYPE: PRT
<213> ORGANISM: Homo sapiens

<400> SEQUENCE: 15

Gly Gly Gln Val Glu Val Lys Ser Glu
1               5

<210> SEQ ID NO 16
<211> LENGTH: 19
<212> TYPE: PRT
<213> ORGANISM: Homo sapiens

<400> SEQUENCE: 16

Gly Gln Val Glu Val Lys Ser Glu Lys Leu Asp Phe Lys Asp Arg Val
1               5                   10                  15

Gln Ser Lys

<210> SEQ ID NO 17
<211> LENGTH: 770
<212> TYPE: PRT
<213> ORGANISM: Homo sapiens

<400> SEQUENCE: 17

Met Leu Pro Gly Leu Ala Leu Leu Leu Ala Ala Trp Thr Ala Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
            35                  40                  45

Asn Gly Lys Trp Asp Ser Asp Pro Ser Gly Thr Lys Thr Cys Ile Asp
```

```
                    50                  55                  60
Thr Lys Glu Gly Ile Leu Gln Tyr Cys Gln Glu Val Tyr Pro Glu Leu
 65                  70                  75                  80

Gln Ile Thr Asn Val Val Glu Ala Asn Gln Pro Val Thr Ile Gln Asn
                     85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
                115                 120                 125

Val Pro Asp Lys Cys Lys Phe Leu His Gln Glu Arg Met Asp Val Cys
                130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Asn Val Asp Ser Ala Asp Ala Glu Glu Asp Asp Ser Asp Val
                195                 200                 205

Trp Trp Gly Gly Ala Asp Thr Asp Tyr Ala Asp Gly Ser Glu Asp Lys
                210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Glu Ser Val Glu Glu Val Val Arg
                275                 280                 285

Glu Val Cys Ser Glu Gln Ala Glu Thr Gly Pro Cys Arg Ala Met Ile
                290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Ala Met Ser Gln Ser Leu Leu Lys Thr
                340                 345                 350

Thr Gln Glu Pro Leu Ala Arg Asp Pro Val Lys Leu Pro Thr Thr Ala
                355                 360                 365

Ala Ser Thr Pro Asp Ala Val Asp Lys Tyr Leu Glu Thr Pro Gly Asp
                370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
                435                 440                 445

Glu Arg Gln Gln Leu Val Glu Thr His Met Ala Arg Val Glu Ala Met
                450                 455                 460

Leu Asn Asp Arg Arg Arg Leu Ala Leu Glu Asn Tyr Ile Thr Ala Leu
465                 470                 475                 480
```

```
Gln Ala Val Pro Pro Arg Pro Arg His Val Phe Asn Met Leu Lys Lys
            485                 490                 495
Tyr Val Arg Ala Glu Gln Lys Asp Arg Gln His Thr Leu Lys His Phe
        500                 505                 510
Glu His Val Arg Met Val Asp Pro Lys Lys Ala Ala Gln Ile Arg Ser
    515                 520                 525
Gln Val Met Thr His Leu Arg Val Ile Tyr Glu Arg Met Asn Gln Ser
530                 535                 540
Leu Ser Leu Leu Tyr Asn Val Pro Ala Val Ala Glu Glu Ile Gln Asp
545                 550                 555                 560
Glu Val Asp Glu Leu Leu Gln Lys Glu Gln Asn Tyr Ser Asp Asp Val
                565                 570                 575
Leu Ala Asn Met Ile Ser Glu Pro Arg Ile Ser Tyr Gly Asn Asp Ala
            580                 585                 590
Leu Met Pro Ser Leu Thr Glu Thr Lys Thr Thr Val Glu Leu Leu Pro
        595                 600                 605
Val Asn Gly Glu Phe Ser Leu Asp Asp Leu Gln Pro Trp His Ser Phe
    610                 615                 620
Gly Ala Asp Ser Val Pro Ala Asn Thr Glu Asn Glu Val Glu Pro Val
625                 630                 635                 640
Asp Ala Arg Pro Ala Ala Asp Arg Gly Leu Thr Thr Arg Pro Gly Ser
                645                 650                 655
Gly Leu Thr Asn Ile Lys Thr Glu Glu Ile Ser Glu Val Lys Met Asp
            660                 665                 670
Ala Glu Phe Arg His Asp Ser Gly Tyr Glu Val His His Gln Lys Leu
        675                 680                 685
Val Phe Phe Ala Glu Asp Val Gly Ser Asn Lys Gly Ala Ile Ile Gly
    690                 695                 700
Leu Met Val Gly Gly Val Val Ile Ala Thr Val Ile Val Ile Thr Leu
705                 710                 715                 720
Val Met Leu Lys Lys Lys Gln Tyr Thr Ser Ile His His Gly Val Val
                725                 730                 735
Glu Val Asp Ala Ala Val Thr Pro Glu Glu Arg His Leu Ser Lys Met
            740                 745                 750
Gln Gln Asn Gly Tyr Glu Asn Pro Thr Tyr Lys Phe Phe Glu Gln Met
        755                 760                 765
Gln Asn
    770

<210> SEQ ID NO 18
<211> LENGTH: 6
<212> TYPE: PRT
<213> ORGANISM: Homo sapiens

<400> SEQUENCE: 18

Ser Glu Lys Leu Asp Phe
1               5

<210> SEQ ID NO 19
<211> LENGTH: 19
<212> TYPE: PRT
<213> ORGANISM: Homo sapiens

<400> SEQUENCE: 19

Gly Gln Val Glu Val Lys Ser Glu Lys Leu Asp Phe Lys Asp Arg Val
1               5                   10                  15
```

Gln Ser Lys

<210> SEQ ID NO 20
<211> LENGTH: 15
<212> TYPE: PRT
<213> ORGANISM: Homo sapiens

<400> SEQUENCE: 20

Lys Glu Thr Cys Ser Glu Lys Ser Thr Asn Leu His Asp Tyr Gly
1               5                   10                  15

<210> SEQ ID NO 21
<211> LENGTH: 16
<212> TYPE: PRT
<213> ORGANISM: Homo sapiens

<400> SEQUENCE: 21

Thr Glu Glu Ile Ser Glu Val Lys Met Asp Ala Gly Phe Arg His Asp
1               5                   10                  15

<210> SEQ ID NO 22
<211> LENGTH: 14
<212> TYPE: PRT
<213> ORGANISM: Homo sapiens

<400> SEQUENCE: 22

Glu Arg His Leu Ser Lys Met Gln Gln Asn Gly Tyr Glu Asn
1               5                   10

<210> SEQ ID NO 23
<211> LENGTH: 67
<212> TYPE: PRT
<213> ORGANISM: Homo sapiens

<400> SEQUENCE: 23

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys
65

<210> SEQ ID NO 24
<211> LENGTH: 63
<212> TYPE: PRT
<213> ORGANISM: Homo sapiens

<400> SEQUENCE: 24

Ser Thr Pro Thr Ala Glu Asp Val Thr Ala Pro Leu Val Asp Glu Gly
1               5                   10                  15

Ala Pro Gly Lys Gln Ala Ala Gln Pro His Thr Glu Ile Pro Glu
                20                  25                  30

Gly Thr Thr Ala Glu Glu Ala Gly Ile Gly Asp Thr Pro Ser Leu Glu
            35                  40                  45

Asp Glu Ala Ala Gly His Val Thr Gln Ala Arg Met Val Ser Lys
        50                  55                  60

```
<210> SEQ ID NO 25
<211> LENGTH: 18
<212> TYPE: PRT
<213> ORGANISM: Homo sapiens

<400> SEQUENCE: 25

Ser Lys Asp Gly Thr Gly Ser Asp Asp Lys Lys Ala Lys Gly Ala Asp
1               5                   10                  15

Gly Lys

<210> SEQ ID NO 26
<211> LENGTH: 24
<212> TYPE: PRT
<213> ORGANISM: Homo sapiens

<400> SEQUENCE: 26

Ile Ala Thr Pro Arg Gly Ala Ala Pro Pro Gly Gln Lys Gly Gln Ala
1               5                   10                  15

Asn Ala Thr Arg Ile Pro Ala Lys
            20

<210> SEQ ID NO 27
<211> LENGTH: 6
<212> TYPE: PRT
<213> ORGANISM: Homo sapiens

<400> SEQUENCE: 27

Thr Pro Pro Ala Pro Lys
1               5

<210> SEQ ID NO 28
<211> LENGTH: 10
<212> TYPE: PRT
<213> ORGANISM: Homo sapiens

<400> SEQUENCE: 28

Thr Pro Pro Ser Ser Gly Glu Pro Pro Lys
1               5                   10

<210> SEQ ID NO 29
<211> LENGTH: 44
<212> TYPE: PRT
<213> ORGANISM: Homo sapiens

<400> SEQUENCE: 29

Ser Gly Asp Arg Ser Gly Tyr Ser Ser Pro Gly Ser Pro Gly Thr Pro
1               5                   10                  15

Gly Ser Arg Ser Arg Thr Pro Ser Leu Pro Thr Pro Pro Thr Arg Glu
            20                  25                  30

Pro Lys Lys Val Ala Val Val Arg Thr Pro Pro Lys
            35                  40

<210> SEQ ID NO 30
<211> LENGTH: 6
<212> TYPE: PRT
<213> ORGANISM: Homo sapiens

<400> SEQUENCE: 30

Ser Pro Ser Ser Ala Lys
1               5

<210> SEQ ID NO 31
```

```
<211> LENGTH: 17
<212> TYPE: PRT
<213> ORGANISM: Homo sapiens

<400> SEQUENCE: 31

Ser Arg Leu Gln Thr Ala Pro Val Pro Met Pro Asp Leu Lys Asn Val
1               5                   10                  15
Lys

<210> SEQ ID NO 32
<211> LENGTH: 81
<212> TYPE: PRT
<213> ORGANISM: Homo sapiens

<400> SEQUENCE: 32

Ile Gly Ser Thr Glu Asn Leu Lys His Gln Pro Gly Gly Gly Lys Val
1               5                   10                  15

Gln Ile Ile Asn Lys Lys Leu Asp Leu Ser Asn Val Gln Ser Lys Cys
                20                  25                  30

Gly Ser Lys Asp Asn Ile Lys His Val Pro Gly Gly Gly Ser Val Gln
            35                  40                  45

Ile Val Tyr Lys Pro Val Asp Leu Ser Lys Val Thr Ser Lys Cys Gly
        50                  55                  60

Ser Leu Gly Asn Ile His His Lys Pro Gly Gly Gly Gln Val Glu Val
65                  70                  75                  80

Lys

<210> SEQ ID NO 33
<211> LENGTH: 13
<212> TYPE: PRT
<213> ORGANISM: Homo sapiens

<400> SEQUENCE: 33

Ser Glu Lys Leu Asp Phe Lys Asp Arg Val Gln Ser Lys
1               5                   10

<210> SEQ ID NO 34
<211> LENGTH: 17
<212> TYPE: PRT
<213> ORGANISM: Homo sapiens

<400> SEQUENCE: 34

Ile Gly Ser Leu Asp Asn Ile Thr His Val Pro Gly Gly Gly Asn Lys
1               5                   10                  15

Lys

<210> SEQ ID NO 35
<211> LENGTH: 15
<212> TYPE: PRT
<213> ORGANISM: Homo sapiens

<400> SEQUENCE: 35

Ile Glu Thr His Lys Leu Thr Phe Arg Glu Asn Ala Lys Ala Lys
1               5                   10                  15

<210> SEQ ID NO 36
<211> LENGTH: 10
<212> TYPE: PRT
<213> ORGANISM: Homo sapiens

<400> SEQUENCE: 36
```

```
Thr Asp His Gly Ala Glu Ile Val Tyr Lys
1               5                   10
```

<210> SEQ ID NO 37
<211> LENGTH: 46
<212> TYPE: PRT
<213> ORGANISM: Homo sapiens

<400> SEQUENCE: 37

```
Ser Pro Val Val Ser Gly Asp Thr Ser Pro Arg His Leu Ser Asn Val
1               5                   10                  15

Ser Ser Thr Gly Ser Ile Asp Met Val Asp Ser Pro Gln Leu Ala Thr
                20                  25                  30

Leu Ala Asp Glu Val Ser Ala Ser Leu Ala Lys Gln Gly Leu
                35                  40                  45
```

<210> SEQ ID NO 38
<211> LENGTH: 439
<212> TYPE: PRT
<213> ORGANISM: Homo sapiens

<400> SEQUENCE: 38

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
                35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
                115                 120                 125

Ser Lys Ser Lys Asp Gly Thr Gly Ser Asp Asp Lys Lys Ala Lys Gly
                130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
                210                 215                 220

Lys Val Ala Trp Arg Thr Pro Pro Lys Ser Pro Ser Ser Ala Lys Ser
225                 230                 235                 240

Arg Leu Gln Thr Ala Pro Val Pro Met Pro Asp Leu Lys Asn Val Lys
                245                 250                 255

Ser Lys Ile Gly Ser Thr Glu Asn Leu Lys His Gln Pro Gly Gly Gly
                260                 265                 270
```

```
Lys Val Gln Ile Ile Asn Lys Lys Leu Asp Leu Ala Asn Val Gln Ser
            275                 280                 285

Lys Cys Gly Ser Lys Asp Asn Ile Lys His Val Pro Gly Gly Gly Ser
        290                 295                 300

Val Gln Ile Val Tyr Lys Pro Val Asp Leu Ser Lys Val Thr Ser Lys
305                 310                 315                 320

Cys Gly Ser Leu Gly Asn Ile His His Lys Pro Gly Gly Gly Gln Val
                325                 330                 335

Glu Val Lys Ser Glu Lys Leu Asp Phe Lys Asp Arg Val Gln Ser Lys
            340                 345                 350

Ile Gly Ser Leu Asp Asn Ile Thr His Val Pro Gly Gly Gly Asn Lys
        355                 360                 365

Lys Ile Glu Thr His Lys Leu Thr Phe Arg Glu Asn Ala Lys Ala Lys
    370                 375                 380

Thr Asp His Gly Ala Glu Ile Val Tyr Lys Ser Pro Trp Ser Gly Asp
385                 390                 395                 400

Thr Ser Pro Arg His Leu Ser Asn Val Ser Ser Thr Gly Ser Ile Asp
                405                 410                 415

Met Val Asp Ser Pro Gln Leu Ala Thr Leu Ala Asp Glu Val Ser Ala
            420                 425                 430

Ser Leu Ala Lys Gln Gly Leu
            435

<210> SEQ ID NO 39
<211> LENGTH: 439
<212> TYPE: PRT
<213> ORGANISM: Homo sapiens

<400> SEQUENCE: 39

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205
```

-continued

Arg Ser Arg Thr Pro Ser Leu Pro Thr Pro Thr Arg Glu Pro Lys
    210                 215                 220

Lys Val Ala Trp Arg Thr Pro Pro Lys Ser Pro Ser Ser Ala Lys Ser
225                 230                 235                 240

Arg Leu Gln Thr Ala Pro Val Pro Met Pro Asp Leu Lys Asn Val Lys
                245                 250                 255

Ser Lys Ile Gly Ser Thr Glu Asn Leu Lys His Gln Pro Gly Gly Gly
                260                 265                 270

Lys Val Gln Ile Ile Asn Lys Lys Leu Asp Leu Ser Asn Val Gln Ser
                275                 280                 285

Lys Cys Gly Ser Lys Asp Asn Ile Lys His Val Pro Gly Gly Gly Ala
    290                 295                 300

Val Gln Ile Val Tyr Lys Pro Val Asp Leu Ser Lys Val Thr Ser Lys
305                 310                 315                 320

Cys Gly Ser Leu Gly Asn Ile His His Lys Pro Gly Gly Gly Gln Val
                325                 330                 335

Glu Val Lys Ser Glu Lys Leu Asp Phe Lys Asp Arg Val Gln Ser Lys
                340                 345                 350

Ile Gly Ser Leu Asp Asn Ile Thr His Val Pro Gly Gly Gly Asn Lys
                355                 360                 365

Lys Ile Glu Thr His Lys Leu Thr Phe Arg Glu Asn Ala Lys Ala Lys
    370                 375                 380

Thr Asp His Gly Ala Glu Ile Val Tyr Lys Ser Pro Trp Ser Gly Asp
385                 390                 395                 400

Thr Ser Pro Arg His Leu Ser Asn Val Ser Ser Thr Gly Ser Ile Asp
                405                 410                 415

Met Val Asp Ser Pro Gln Leu Ala Thr Leu Ala Asp Glu Val Ser Ala
                420                 425                 430

Ser Leu Ala Lys Gln Gly Leu
        435

<210> SEQ ID NO 40
<211> LENGTH: 439
<212> TYPE: PRT
<213> ORGANISM: Homo sapiens

<400> SEQUENCE: 40

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly

```
                130             135             140
Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
                195                 200                 205

Arg Ser Arg Thr Pro Ser Leu Pro Thr Pro Pro Thr Arg Glu Pro Lys
                210                 215                 220

Lys Val Ala Trp Arg Thr Pro Pro Lys Ser Pro Ser Ser Ala Lys Ser
225                 230                 235                 240

Arg Leu Gln Thr Ala Pro Val Pro Met Pro Asp Leu Lys Asn Val Lys
                245                 250                 255

Ser Lys Ile Gly Ser Thr Glu Asn Leu Lys His Gln Pro Gly Gly Gly
                260                 265                 270

Lys Val Gln Ile Ile Asn Lys Lys Leu Asp Leu Ser Asn Val Gln Ser
                275                 280                 285

Lys Cys Gly Ser Lys Asp Asn Ile Lys His Val Pro Gly Gly Gly Ser
                290                 295                 300

Val Gln Ile Val Tyr Lys Pro Val Asp Leu Ala Lys Val Thr Ser Lys
305                 310                 315                 320

Cys Gly Ser Leu Gly Asn Ile His His Lys Pro Gly Gly Gly Gln Val
                325                 330                 335

Glu Val Lys Ser Glu Lys Leu Asp Phe Lys Asp Arg Val Gln Ser Lys
                340                 345                 350

Ile Gly Ser Leu Asp Asn Ile Thr His Val Pro Gly Gly Gly Asn Lys
                355                 360                 365

Lys Ile Glu Thr His Lys Leu Thr Phe Arg Glu Asn Ala Lys Ala Lys
                370                 375                 380

Thr Asp His Gly Ala Glu Ile Val Tyr Lys Ser Pro Trp Ser Gly Asp
385                 390                 395                 400

Thr Ser Pro Arg His Leu Ser Asn Val Ser Ser Thr Gly Ser Ile Asp
                405                 410                 415

Met Val Asp Ser Pro Gln Leu Ala Thr Leu Ala Asp Glu Val Ser Ala
                420                 425                 430

Ser Leu Ala Lys Gln Gly Leu
                435
```

TAU PROTEASE COMPOSITIONS AND METHODS OF USE

CROSS-REFERENCE TO RELATED APPLICATIONS

The present application claims priority to U.S. Provisional Patent Appl. Nos. 61/488,493, 61/544,090 and 61/569,558, filed May 20, 2011, Oct. 6, 2011, and Dec. 12, 2011, respectively; the contents of each of which is specifically incorporated herein in its entirety by express reference thereto.

BACKGROUND OF THE INVENTION

Field of the Invention

The present invention relates generally to the fields of molecular biology, and more specifically to tau protein, and protease-active fragments and variants thereof. In particular embodiments, truncated tau fragments and tau protease variants are provided that retain substantial serine protease.

Description of Related Art

Alzheimer's Disease

There is a large and rapidly growing unmet need for disease modifying drugs for Alzheimer's disease. Currently more than 30 million people suffer from AD worldwide and this number doubles about every 20 years. In the US, it is estimated that there are 5.4 million AD sufferers. AD affects 1 out of 4 people over age 75 and 1 out of 3 people over 80. Payments for care in 2012 are estimated to exceed $200 billion (2012 Alzheimer's disease Facts and Figures, Alzheimer's Association). Presently, only 5 mildly effective AD symptom-treating drugs exist, but none that treat the underlying neurodegenerative processes. FDA approved medications provide limited symptomatic relief, but do not halt, slow or reverse disease progression. It is estimated that the 2009 market for anti-Alzheimer's drugs was approximately $4.3 billion and is expected to increase to over $14 billion by the end of the decade based on the introduction of disease modifying drugs (DMDs), which are expected to fuel >50% of the market growth.

The symptoms of AD manifest slowly and the first symptom may only be mild forgetfulness. In this stage, individuals may forget recent events, activities, the names of familiar people or things and may not be able to solve simple math problems. As the disease progresses into moderate stages of AD, symptoms are more easily noticed and become serious enough to cause people with AD or their family members to seek medical help. Moderate-stage symptoms of AD include forgetting how to do simple tasks such as grooming, and problems develop with speaking, understanding, reading, or writing. Severe stage AD patients may become anxious or aggressive, may wander away from home and ultimately need total care.

The classical hallmarks of AD are inter-neuronal plaques consisting of precipitates or aggregates of amyloid β protein (Aβ), and intra-neuronal neurofibrillary tangles (NFTs) consisting of precipitates or aggregates of tau protein. The amyloid cascade hypothesis has been widely accepted as the pathological pathway of AD, that Aβ drives AD pathogenesis and secondarily induces the formation of abnormal tau protein. Genetic evidence suggests that that mutations leading to increased accumulation of Aβ aggregates leads to familial AD. However, there are a number of weaknesses in the Aβ cascade hypothesis in that it does not address the importance of other pathways that can cause neurodegeneration (Seabrook et al., 2007). The accumulation and distribution of NFTs in the brains of AD patients is highly correlated with disease progression and can be used to stage AD by post-mortem brain histopathology. A recent study was conducted in which two thousand three hundred and thirty two non-selected brains from 1- to 100-year-old individuals were examined for abnormal tau and for the detection of Aβ. This study showed that AD-related tauopathy begins in the early decades of life in the lower brainstem and before the occurrence of plaques contradicting the amyloid cascade hypothesis (Braak et al., 2011). Furthermore, there have been a number of late stage clinical failures that call into question the understanding of the molecular mechanism of AD pathology (see, e.g., Table 1.).

TABLE 1

LATE-STAGE FAILURES OF DRUGS TARGETING Aβ

| Compound | Mode of Action | Company | Status |
|---|---|---|---|
| Tramiprosate (Alzhemed ™) | β-amyloid antagonist | Neurochem | Failed to meet clinical endpoint in Phase III |
| R-flurbiprofen (Flurizan ™) | Reduces levels of Aβ42 | Myriad Genetics | Failed to meet clinical endpoint in Phase III |
| Semagacestat (LY450139 dihydrate) | γ-Secretase inhibitor | Eli Lilly | Failed to meet clinical endpoint in Phase III |
| Bapineuzumab | Humanized mAB specific for the ends of Aβ | Wyeth/Elan, Pfizer/J&J | Subjects were stratified according to APOE genotype in order to meet Phase II endpoint |

Causal Role for Tau in Neurodegenerative Diseases

That tau dysfunction is sufficient for neurodegeneration and dementia, even in the absence of other disease processes comes from direct evidence that mutations in the gene for tau MAPT cause frontotemporal dementia with Parkinsonism (FTDP) linked to chromosome-17 (FTDP-17). The 32 different mutations found in the study of over 100 families can be grouped into categories influencing splicing of the primary transcript and causing changes in amino acid sequence of tau. Most missense mutations are located in the assembly domain and generally reduce the affinity of tau to MTs. Several of these mutations promote aggregation of tau in vitro and in vivo such as P301L and P301S. Mutations in the stem-loop structure at the border of exon 10 and the following intron alter splicing causing aberrations in the ratio of 4R to 3R isoforms demonstrating that maintenance of the proper ratio of tau isoforms is necessary to prevent neurodegeneration and dementia (Goedert and Jakes, 2005). Recent work has shown that tau is a key mediator or enabler of both Aβ- and apoE4-dependent pathogenesis (reviewed in Morris et al., 2011; Huang and Mucke, 2012).

Extracellular Tau in Disease Progression

The role of extracellular tau in neurotoxicity is a relatively new but important concept in the field. There are a number of contributing findings that implicate extracellular tau in AD. Tau pathology spreads contiguously throughout the brain from early to late stage disease suggesting an "infectious" model of disease progression (Schonheit et al., 2004). This notion is supported by a recent report (Frost et al., 2009) that extracellular tau aggregates can propagate tau misfolding from outside to the inside of a cell. Additional backing for this concept comes from a recent report showing that injection of brain extract from a transgenic mouse with aggregated mutant human tau into the brain of transgenic mice with normal human tau transmits tau pathology and induces its spread throughout the brain (Clavaguera et al., 2009). Recently two transgenic models were independently developed that expressed pathological tau P301L in mouse entorhinal cortex (Liu et al., 2012; de Calignon et al., 2012). The published results demonstrated that the pathology spread to adjacent regions of the hippocampus consistent with the model that tau pathology can spread from diseased to healthy neurons. Induction of low levels of pro-aggregation human tau in transgenic mice results in the formation of tau aggregates and tangles composed of both human and normal murine tau (co-aggregation) providing evidence for the "infectious" model by transmission of pathological tau characteristics to normal host tau (Mocanu et al., 2008). A receptor-mediated mechanism for the spread of tau pathology by extracellular tau has been described based on work with cultured neurons (Gomez-Ramos et al., 2006; 2008; 2009). Levels of tau rise in CSF in AD, whereas A$\beta$ levels decrease (Shaw et al., 2009).

Tau Oligomers: A Target for Therapeutic Development

NFTs have been implicated in mediating neurodegeneration in AD and tauopathies as it correlates well with cognitive deficits and neuron loss (Arriagada et al., 1992; Bancher, 1993; Guillozet et al., 2003; Iqbal et al., 2009). However, the study of animal models of tauopathy has shown that memory impairment and neuron loss is dissociated from accumulation of NFT (Brunden et al., 2008). Strong support for this contention came from the analysis of transgenic mice rTg4510 that express tau P301L in the forebrain under control of a tetracycline-regulated promoter. These mice developed memory impairment, neuron loss and NFT when the construct was expressed. However, suppression of expression caused improvement in memory and reduction in neuron loss even as NFTs continued to accumulate clearly demonstrating that pretangle tau species were responsible for the neurodegenerative phenotype (Santacruz et al., 2005). Additionally, there was regional dissociation of neuron loss and NFT pathology (Spires et al., 2006). This mouse model was also used to show that soluble tau, but not tangles, contributed to impairment of hippocampal function (Fox et al., 2011). Transgenic mice expressing a human mutant tau P301S construct prone to aggregation developed hippocampal synapse loss and dysfunction, as well as, microglial activation months before the accumulation of filamentous tau inclusions (Yoshiyama et al., 2007). Similarly, a transgenic mouse model expressing human tau protein with two mutations found in FTDP-17 (P301S and G272V) exhibited axonopathy before tangle formation (Leroy et al., 2007). The triple transgenic AD mouse model accumulating both tau and A$\beta$ pathology was used to study the effects of immuno-reduction of tau and A$\beta$. Antibodies against both proteins were needed to improve learning and memory behavior in these mice. Soluble tau, but not NFT, was reduced by the treatment (Oddo et al., 2006).

A study of normal and AD CSF specimens using a tau oligomer-specific antibody showed AD-specific accumulation of tau oligomers early in disease (Lasagna-Reeves et al., 2012). Furthermore, tau oligomers caused impairment of memory and induced synaptic and mitochondrial dysfunction in mice (Lasagna-Reeves et al., 2011). However, the mechanism by which tau oligomers cause these neurodegenerative effects has not been established.

Proteases Cutting Tau

Tau cleavage has been shown to play an important role in tau aggregation and neurodegeneration (recently reviewed in Wang el al., 2010; Hanger and Wray, 2010). Tau truncation leads to the formation of aggregation-prone fragments leading to the formation of toxic aggregates and leads to the formation of toxic fragments which do not aggregate. Thus, targeting the proteolysis of tau would be beneficial for the development of therapeutics for AD and related tauopathies. Tau is a substrate for multiple proteases and because of its natively unfolded conformation it is very susceptible to proteolysis. Tau can be cut by trypsin and chymotrypsin in addition to endogenous proteases such as caspases, and calpain and puromycin-sensitive aminopetidase. The proteosome, which degrades misfolded proteins, also degrades tau but is inhibited when bound to filaments of tau. There are also unknown proteases that generate fragments of tau early in AD.

The Role of Tau in Alzheimer's Disease

The classical hallmarks of AD are inter-neuronal plaques consisting of precipitates or aggregates of amyloid beta protein (A$\beta$), and intra-neuronal neurofibrillary tangles (NFTs) of tau protein. Tau protein promotes microtubule assembly and stability and is critical for the function of axons, whereas the normal function of A$\beta$ is not fully understood. The amyloid cascade hypothesis has been widely accepted as the pathological pathway of AD. It holds that the generation of A$\beta$ and accumulation of A$\beta$ aggregates in the brain initiate the disease process. It is supported by genetic evidence that mutations leading to increased accumulation of A$\beta$ aggregates leads to familial AD. However, there are a number of weaknesses in the A$\beta$ cascade hypothesis in that it does not address the importance of other pathways that can cause neurodegeneration (Seabrook et al., 2007). The accumulation and distribution of NFTs in the brains of AD patients is highly correlated with disease progression and can be used to stage AD by post-mortem brain histopathology, whereas there is poor correlation between AD and the accumulation of neuritic plaques composed of $\beta$-amyloid. This has been used to challenge the amyloid hypothesis (Josephs et al., 2008). Lackluster results for A$\beta$-directed therapeutics in late stage clinical trials has increased interest in exploring alternative targets for drug discovery such as tau (Iqbal et al., 2009).

Deficiencies in the Prior Art

Unfortunately, no cure is yet available for AD. Today, medication therapy focuses on controlling the symptoms of AD and its various stages. For example, mild to moderate AD is often treated with cholinesterase inhibitors such as donepezil (ARICEPT®, Eisai Co., Ltd/Pfizer, Inc.), rivastigmine (EXELON®, Novartis AG/Sandoz AG), galantamine (RAZADYNE®, Johnson & Johnson), [and to a lesser extent, tacrine (COGNEX®), Warner-Lambert Co.], while moderate to severe AD is often treated with donepezil (ARICEPT®) or N-methyl D-aspartate antagonists such as memantine (NAMENDA®, Forest Laboratories, Inc.), or a combination thereof. Although these medications may help delay or prevent AD symptoms from becoming worse for a limited period of time, there is no clear evidence that these medications have any effect on the underlying progression of the disease itself.

While extensive research in the past decade has identified possible biomarkers for AD, there is still an urgent need for composition and methods that are specifically useful in diagnosing, treating, preventing, and monitoring the progress of AD in at-risk or affected individuals. New compositions and methods are also needed to serve as drug targets for the identification, synthesis, and/or adaptation of existing chemical compounds for use in the treatment of AD and its symptoms. Furthermore, there is also a need for development of new classes of drugs for treatment of the disease, including, for example, immunotherapeutic agents and next-generation therapeutics.

BRIEF SUMMARY OF THE INVENTION

The present invention overcomes these and other limitations inherent in the prior art by providing novel and nonobvious peptides, polypeptides, and proteins and related biological compositions, including polynucleotides that encode, as well as expression constructs, vectors and recombinant host cells that express one or more mammalian tau proteases, truncations, or variants thereof. The compositions of the present invention, which are based upon the autoproteolytic properties of portions of tau protein, are particularly beneficial as they also function as serine proteases, and may play an important part in the development of new drug candidates for the diagnosis, treatment, prevention, and/or amelioration of one or more symptoms of various diseases of the brain, neural deficit, and neurological conditions such as early-onset senility, dementia, age-related memory loss, Alzheimer's disease, and the like.

The invention was, in part, initially based upon the inventor's surprising discovery that tau protein possesses autoproteolytic properties, and can function in vitro and/or in vivo as a serine protease. The inventors further discovered that particular truncated forms of human tau protein retained significant protease activity, even when the truncated polypeptides contained less than a third of the amino acid sequence of the full-length tau protease. The inventors have also discovered that particular mutations in the wild-type tau protease sequence also gave rise to particularly useful tau protease variants, which further identified the functional domain(s) of tau protease, and led to characterization of protein variants useful in diagnostic and/or therapeutic applications, including new drug discovery.

The present invention also provides novel and non-obvious nucleic acid segments, expression vectors, recombinant host cells, oligonucleotide amplification primers, and oligonucleotide detection probes, and the like that are specific for, or that include at least one isolated gene, or nucleic acid segment that encodes all or a portion of a mammalian tau protease, or all or a portion of a protease-active tau fragment, tau protease variant, tau protease mutant, a tau protein fusion product, or one or more epitopes, active sites, binding domains, catalytic domains, or regulatory regions of a mammalian tau protease. Further provided are isolated genes, nucleic acid segments and expression constructs that encode a mammalian, and preferably human, tau protease, or a protease-active fragment, variant, mutant, epitope, or fusion protein thereof.

The present invention also provides methods for making the tau proteases of the present invention, for making active fragments of tau protein that are proteolytically active, and for making expression constructs, recombinant vectors, and transformed host cells that express tau protease polynucleotides to produce tau protease polypeptides as well as active fragments or epitopes thereof in selected recombinant expression systems. The invention also provides uses of the disclosed polypeptides and polynucleotides in a variety of diagnostic, therapeutic, investigational research, and drug discovery methodologies.

In one embodiment, the invention provides an isolated peptide or polypeptide of about 50 to about 300 amino acids in length, alternatively of about 70 to about 250 amino acids, or of about 80 to about 220 amino acids in length, wherein the peptide or polypeptide comprises, consists essentially of, or alternatively, consists of, an amino acid sequence that is at least 90% identical, alternatively at least 92% identical, 94% identical, 96% identical, or 98% or greater identical to an at least 50, an at least 60, an at least 70, or an at least 80 or more contiguous amino acid sequence as set forth in any one of SEQ ID NO:1, SEQ ID NO:2, SEQ ID NO:3, SEQ ID NO:4, SEQ ID NO:5, or SEQ ID NO:6. Preferably, the isolated peptide or polypeptide has tau protease activity, and preferably a serine protease-type biological activity in vitro and/or in vivo.

In another embodiment, the invention provides a tau protease variant peptide or polypeptide comprising an amino acid sequence of a starting mammalian tau protease that has been substituted in at least one, alternatively at least two, at least three, or at least four or more amino acid(s) at one or more position that corresponds to one or more amino acid residue 5, 257, 260, 266, 272, 273, 279, 280, 285, 296, 301, 303, 304, 305, 315, 317, 320, 332, 335, 336, 337, 342, 352, 356, 363, 369, 389, 406, or 427 of SEQ ID NO:6, wherein the substitution confers to the protease variant peptide or polypeptide an enhanced serine protease activity, when compared to that of the original, un-substituted tau protease peptide or polypeptide. Preferably, the one or more amino acid substitutions is an arginine-to-histidine substitution, an arginine-to-leucine substitution, an arginine-to-tryptophan substitution, an asparagine-to-alanine substitution, an asparagine-to-histidine substitution, an asparagine-to-lysine substitution, a glutamate-to-valine substitution, a glutamine-to-arginine substitution, a glycine-to-arginine substitution, a glycine-to-serine substitution, a glycine-to-valine substitution, an isoleucine-to-valine substitution, a leucine-to-arginine substitution, a leucine-to-valine substitution, a lysine-to-isoleucine substitution, a lysine-to-methionine substitution, a lysine-to-threonine substitution, a proline-to-leucine substitution, a proline-to-serine substitution, a proline-to-threonine substitution, a serine-to-asparagine substitution, a serine-to-isoleucine substitution, a serine-to-leucine substitution, a serine-to-phenalanine substitution, a threonine-to-methionine substitution, a valine-to-isoleucine substitution, a valine-to-methionine substitution, or any combination thereof. In illustrative embodiments, the one or more amino acid substitutions include an R5H substitution, an R5L substitution, a K257T substitution, a I260V substitution, a L266V substitution, a G272V substitution, a G273R substitution, a N279K substitution, a L284V substitution, a N296A substitution, a N296H substitution, a P301L substitution, a P301S substitution, a P301T substitution, a G303V substitution, a G304S substitution, a S305I substitution, a S305N substitution, a L315R substitution, a K317M substitution, a S320F substitution, a P332S substitution, a G335S substitution, a G335V substitution, a Q336R substitution, a V337M substitution, an E342V substitution, a S352L substitution, a S356T substitution, a V363I substitution, a K369I substitution, a G389R substitution, a R406W substitution, or a T427M substitution, or any combination thereof.

The present invention further provides an antibody, or an antigen binding fragment thereof, which binds specifically to a tau protein or protease, and in particular embodiments, specifically binds to one of the truncated tau proteases or substituted tau variants disclosed herein. In some embodiments, the antibody or antigen binding fragment specifically binds to one or more of the truncated or substituted tau proteases disclosed herein, but does not substantially bind to a polypeptide that comprises the entire wild-type tau protein sequence, such as the amino acid sequence set forth in SEQ ID NO:6, which is the 4R2N full-length sequence. Such antibodies may include monoclonal, polyclonal and/or monospecific antibodies and antigen binding fragments.

In another aspect, the invention provides isolated polynucleotides and nucleic acid segments that encode one or more of the tau protease peptides, polypeptides, proteins, or that encodes an antibody or antigen binding fragment specific for such a tau protease peptide, polypeptide, or protein.

Similarly, the invention provides expression constructs, recombinant vectors, and isolated host cells transformed with one or more such vectors, constructs, or polynucleotides that encode one or more of the disclosed tau protease peptides or polypeptides herein, or one or more of the tau-specific antibodies or antigen binding fragments as described herein. In illustrative embodiments, such constructs are adapted and configured for expression of the tau protease or tau-specific antibody or antigen binding fragment in one or more mammalian (and in particular, human) host cells. In related embodiments, such polynucleotides may be codon-optimized for expression in one or more non-mammalian cells or host systems, including for example, recombinant production of proteins (including pilot and large-scale preparation) in suitable bacterial, fungal, yeast, or other non-mammalian animal cells as described in detail elsewhere herein.

In further embodiments, the proteins, peptides, polypeptides, antibodies, antigen binding fragments, polynucleotides, nucleic acid segments, expression constructs, vectors, and/or recombinant host cells provided herein may be formulated in one or more buffers, diluents, vehicles, or pharmaceutically-acceptable excipients. Preferably, one or more of the tau protease-related compounds of the present invention may be formulated for pharmaceutical administration to a mammal, such as a human, or may be formulated for use in one or more diagnostic, therapeutic, investigational, research, or drug discovery methodologies, assays, protocols, or regimens.

In certain embodiments, such compositions may be prepared for use in therapy, diagnosis, amelioration of symptoms, or in one or more investigational assays, protocols, and/or drug discovery regimens. In particular embodiments, the disclosed compositions are formulated for use in the therapy, diagnosis, amelioration of symptoms, or drug discovery for one or more diseases, dysfunctions, abnormal conditions, deficits, defects, trauma, or injury in a mammal. Preferably, such compositions may be useful when formulated for use in the treatment, prevention, diagnosis, or the amelioration of one or more symptoms of a neurological condition in a human, including, without limitation, a tauopathy, a neural deficit, dementia, senility, age-related memory loss, traumatic brain injury, or Alzheimer's disease, or any combination thereof.

The invention also provides methods for producing one or more truncated tau proteases or one or more tau protease variants. Such methods generally involve culturing a population of recombinant host cells comprising a polynucleotide sequence that encodes the selected tau peptide or polypeptide, under conditions conducive to the expression of the truncated tau protease or the tau protease variant, and (b) recovering the expressed truncated tau protease or the tau protease variant from the population of host cells or the culture medium in which the host cells were grown or otherwise cultured.

The invention further provides methods of identifying a serine protease inhibitor from a population of compounds suspected of containing at least one serine protease inhibitor, including large-scale, and automated compound library screening, and such like. The method, in an overall and general sense includes at least the step of contacting a compound or population of compounds suspected of inhibiting serine protease activity with one or more of the tau protease peptides or polypeptides disclosed herein, under conditions effective for observing functional tau protease proteolytic activity, and determining whether or not one or more of the contacted compounds inhibits or reduces the tau proteolytic activity, wherein inhibition of the tau protease activity by a compound is indicative of that compound's having serine protease activity.

Each of the foregoing aspects of the invention are described in further detail in the text, examples, and figures which follow:

Tau Protease Polypeptides

As described above, the present invention provides recombinant tau protease-active peptides, proteins, or fusion proteins, preferably of human origin, prepared at levels that could not previously be obtained prior to the present invention. The methods comprise expressing a gene encoding a tau protease polypeptide, protein or fusion protein in a recombinant host cell and purifying the expressed polypeptide, protein or fusion protein away from total recombinant host cell components to prepare about 100 µg to about 1000 mg of a recombinant tau protease or a tau protease-active polypeptide, protein, variant, mutant, or a fusion protein thereof. With scale up, the inventor contemplates that 10-fold increases can be achieved yielding up to about 10 g of recombinant tau protease polypeptides.

Tau protease fusion proteins or constructs including a fragment of a tau protein or polypeptide sequence operatively linked to distinct, selected amino acid sequences, such as a selected antigenic amino acid sequence, a selected amino acid sequence with a particular binding affinity, and DNA binding or trans-activation amino acid sequences, are also encompassed within the invention. Particularly, tau protease-active amino acid sequences operatively attached to glutathione-S-transferase amino acid sequences are provided, as are fusion proteins with selectably-cleavable bonds, and such like, which are useful in a variety of diagnostic, therapeutic, and drug discovery protocols.

Tau Protease-Encoding Polynucleotides

As described above, the present invention also provides polynucleotides and nucleic acid segments that encode one or more of the tau proteases disclosed herein.

Preferably, these polynucleotides and nucleic acid segments will encode a mammalian, and preferably a human, tau protease, or a protease-active fragment, variant, mutant, epitope, or fusion protein thereof that comprises, consists essentially of, or alternatively, consists of, an amino acid sequence that is at least about 95% identical to an at least 50 contiguous amino acid sequence from any one or more of SEQ ID NO:1, SEQ ID NO:2, SEQ ID NO:3, SEQ ID NO:4, SEQ ID NO:5, or SEQ ID NO:6, or a biologically-functional equivalent thereof; or a protease-active fragment, variant, mutant, epitope, or fusion protein thereof, or a gene, polynucleotide, or nucleic acid segment that will hybridize thereto under stringent hybridization conditions. These isolated genes and coding regions will therefore preferably include a contiguous nucleic acid sequence that encodes a substantially full-length tau protease coding region as set forth in SEQ ID NO:6, or to a biologically functional equivalent thereof; or to a gene or DNA segment that will hybridize thereto under stringent hybridization conditions.

In certain embodiments, the DNA segments and coding regions may encode one or more mammalian or human tau proteases, or a protease-active fragment, variant, mutant, epitope, or fusion protein thereof. In illustrative examples, the DNA segments and coding sequences are provided that encode a mammalian tau protease-active fragment of about 210 amino acids in length; or a mammalian tau protease-active fragment of about 118 amino acids in length, or a mammalian tau protease-active fragment of about 99 amino acids in length, or a mammalian tau protease-active fragment of about 83 amino acids in length; or a mammalian tau protease-active fragment of about 81 amino acids in length, and preferably wherein the recombinant polypeptide encoded by the fragment possesses tau protease-activity in vitro and/or in vivo. Exemplary such truncated tau proteases include, without limitation, the sequences identified in SEQ ID NO:1, SEQ ID NO:2, SEQ ID NO:3, SEQ ID NO:4, and SEQ ID NO:5 herein, and those truncated tau proteases that are obtainable from within the sequence of the tau protein 4R2N sequence disclosed in SEQ ID NO:6.

Certain genes and DNA segments preferably encode a substantially full-length tau protease, or a truncated protease-active tau protein, or a peptide or polypeptide fragment, mutant, or variant thereof, that includes a contiguous amino acid sequence of at least about 20, about 25, or about 30 amino acids or more from SEQ ID NO:1, SEQ ID NO:2, SEQ ID NO:3, SEQ ID NO:4, SEQ ID NO:5, SEQ ID NO:6, or a biologically functional equivalent thereof; or the genes and DNA segments will hybridize to such a coding sequence under stringent hybridization conditions. More preferably, the genes encode a tau protease or a protease-active truncated polypeptide obtained therefrom, that includes a contiguous amino acid sequence of at least about 40, at least about 45, at least about 50, at least about 55, at least about 60, at least about 65, at least about 70, at least about 75, at least about 80, at least about 85, at least about 90, at least about 95, at least about 100, at least about 110, at least about 115, at least about 125, at least about 130, at least about 140, at least about 150, or even at least about 200 amino acids or more from SEQ ID NO:6, or a biologically functional equivalent thereof; or the genes and DNA segments will hybridize to such a coding sequence under stringent hybridization conditions. Most preferably, these genes and DNA segments will encode a tau protease that comprises, consists essentially of, or alternatively, consists of an amino acid sequence that is at least about 95% identical, at least about 96% identical, at least about 97% identical, at least about 98% identical, or even at least about 99% or greater identical to the amino acid sequence disclosed in any one or more of SEQ ID NO:1, SEQ ID NO:2, SEQ ID NO:3, SEQ ID NO:4, SEQ ID NO:5, or SEQ ID NO:6, or a biologically-functional equivalent thereof; or the genes and DNA segments will hybridize to such a coding sequence under stringent hybridization conditions.

Exemplary genes and DNA segments may also be characterized as encoding a substantially full-length tau protease, or a truncated or protease-active subfragment thereof, that includes within its amino acid sequence a contiguous amino acid sequence of at least about 10 amino acids, or more preferably, of at least about 20 amino acids, of at least about 30 amino acids, of at least about 40 amino acids, of at least about 50 amino acids, of at least about 60 amino acids, of at least about 70 amino acids, of at least about 80 amino acids, of at least about 90 amino acids, of at least about 100 amino acids, of at least about 110 amino acids, of at least about 120 amino acids, of at least about 130 amino acids, of at least about 140 amino acids, of at least about 150 amino acids, or more from any one or more of SEQ ID NO:1, SEQ ID NO:2, SEQ ID NO:3, SEQ ID NO:4, SEQ ID NO:5, or SEQ ID NO:6, or a biologically functional equivalent thereof; and as hybridizing to the nucleic acid sequence that encodes one or more of the protein sequences disclosed in SEQ ID NO:1, SEQ ID NO:2, SEQ ID NO:3, SEQ ID NO:4, SEQ ID NO:5, or SEQ ID NO:6, under moderately-stringent, to stringent hybridization conditions.

DNA segments and isolated genes may also be manipulated to encode a truncated, mutated, or variant tau protease, or a tau protease fusion protein or a polypeptide construct in which at least one tau protease-active protein, polypeptide or peptide-encoding polynucleotide sequence is operatively attached (i.e., operably linked) to a second coding region that encodes a selected peptide or protein sequence. The combination of tau protease-specific sequences, including human tau protease-specific proteins or peptides, with one or more additional selected antigenic amino acid sequences; selected non-antigenic carrier amino acid sequences, for use in immunization; selected adjuvant sequences; amino acid sequences with specific binding affinity for a selected molecule; amino acid sequences that form an active DNA binding or trans-activation domain are particularly contemplated. Certain fusion proteins may be linked together via a protease-sensitive peptide linker, allowing subsequent easy separation.

The DNA segments intended for use in expression will be operatively positioned under the control of, (i.e., "downstream" of), a first promoter that directs expression of a tau protease peptide or polypeptide in a desired host cell. The promoter may be a recombinant promoter, or a promoter naturally associated with tau protease. Recombinant vectors that express one or more nucleic acids that encode such a tau protease, thus form another important aspect of the present invention.

Although sequences encoding protease active polypeptides are particularly preferred, the invention further provides tau-derived oligonucleotides, such as oligonucleotide amplification primers, oligonucleotide detection probes, and other nucleic acid segments, including those characterized as comprising, consisting essentially of, consisting of, or otherwise containing or including: a sequence region that consists of at least about 20, 40, 60 or so contiguous nucleotides that have the same sequence as, or are complementary to, about 20, 40, 60 or so contiguous nucleotides selected from any region of SEQ ID NO:12; or a nucleic acid segment of from about 40, 80, 160 or so to about 5,000, 10,000, or even 20,000 nucleotides in length or more that hybridizes to an at least 15 nucleic acid contiguous sequence from any one of SEQ ID NO:7, SEQ ID NO:8, SEQ ID NO:9, SEQ ID NO:10, SEQ ID NO:11, or SEQ ID NO:12, or to a complement thereof, under standard hybridization conditions, and particularly under hybridization conditions. The nucleic acids of the present invention may also be DNA segments or RNA segments.

Recombinant Vectors and Host Cells Expressing Tau Protease

The present invention also provides recombinant host cells comprising at least one DNA segment or vector that comprises an isolated gene or coding region that encodes a mammalian (and preferably, a human) tau protease, truncate, mutant, or variant protein, polypeptide, domain or any fusion protein thereof. Eukaryotic and prokaryotic host cells are particularly preferred, including bacterial host cells (such as E. coli), fungal host cells, yeast host cells, as well as mammalian (and preferably human) host cells.

The recombinant host cells of the present invention preferably have one or more DNA segments introduced into them by means of a recombinant vector, and preferably express the DNA segment to produce the encoded tau protease. The recombinant host cells may express a substantially full-length tau protease, or one or more truncated tau proteases, or one or more mutants or variants derived from a tau protease, or a tau protease fusion protein, including, for example, those polypeptides that comprise an amino acid sequence that shares at least 95%, 96%, 97%, 98%, or 99% or greater primary amino acid sequence identity with one or more of the amino acid sequences as set forth in SEQ ID NO:1, SEQ ID NO:2, SEQ ID NO:3, SEQ ID NO:4, SEQ ID NO:5, or SEQ ID NO:6, and preferably express serine protease activity in vitro and/or in vivo in appropriate host cells.

Methods for detecting tau protease-specific oligonucleotides or polynucleotides in cells, tissues, or other biological samples are also provided, and generally comprise obtaining sample nucleic acids from a sample suspected of containing tau protease-specific nucleic acid sequences, contacting the sample nucleic acids with a nucleic acid segment that encodes a tau protease under conditions effective to allow hybridization of substantially complementary nucleic acids, and detecting the hybridized complementary nucleic acids thus formed.

Tau Protease Immunodetection Reagents

In addition to the embodiments heretofore described, the present invention also provides tau protease-specific antibodies, antigen binding fragments, immunodetection reagents, and methods for identifying, isolating, quantitating, and purifying tau protease compositions from a sample. The immunodetection reagents may be characterized as an antibody or an antigen binding fragment thereof that has immunospecificity for a mammalian tau protease, and preferably a protein of at least about 10 contiguous amino acids from any one or more of SEQ ID NO:1, SEQ ID NO:2, SEQ ID NO:3, SEQ ID NO:4, SEQ ID NO:5, or SEQ ID NO:6.

The immunodetection reagents of the present invention may further optionally include one or more detectable labels. The detectable labels for use in the present invention may include, for example, a radioactive label, a fluorescent label, a biotin label, or avidin or an enzyme that will generate a detectable product upon contact with an appropriate substrate. The antibodies or antigen binding fragments isolated therefrom used in the immunodetection reagents of the present invention may be made using conventional methods, and are preferably monoclonal antibodies derived from one or more hybridoma cell lines.

The immunodetection kits of the present invention provide a variety of immunodetection means. The immunodetection means may be a detectable label that is operatively attached to a tau protease or to a molecule that is cleaved by the enzymatic action of the tau protease. In other kits, the immunodetection means may be a first anti-tau antibody that binds to a tau protein, preferably wherein the first anti-tau antibody is operatively attached to a detectable label. Additionally, the immunodetection means may be a detectable label that is operatively attached to a human tau protease.

Alternatively, the immunodetection means may be a first anti-tau protease antibody that binds to a human tau protease. The invention further provides kits wherein the first anti-tau protease antibody binds to human tau protease subunits, human tau proteases, or to intact human tau protease enzyme complexes. Further, the first anti-tau protease antibody may be operatively attached to a detectable label.

Certain other kits may comprise a first anti-tau antibody or a secondary anti-antibody, wherein the immunodetection label is operatively attached to a second antibody that has binding affinity for the first anti-tau protease antibody. In such kits, the tau protease, or one or more of its substrates, may be bound to a solid support such as a filter, membrane, column, matrix, or such like. Similarly antibodies used for preparing purified tau proteases or tau protease derivatives may be immobilized on a solid support, with the extract fractionated by applying the extract to the solid support.

Diagnostic Kits for the Detection and Quantitation of Tau Proteins

Diagnostic kits represent another aspect of the invention. Such kits may also comprise one or more distinct container means within the kit for the probes, primers, fluorescent labels, or reaction buffers, polymerases, etc. The kit may also further comprise instructions for using the compositions comprised within the kit in real-time PCR assays, and in real-time PCR FRET-based assays in particular. Instructions may also be provided for the use of the reagents contained within the kit for the detection of polynucleotides encoding a tau protein or one or more tau-derived peptides or protein fragments that retain and/or express tau protease activity in vitro and/or in vivo.

The container means for such kits may typically comprise at least one vial, test tube, flask, bottle, syringe or other container means, into which the disclosed tau- or tau protease fragment-specific oligonucleotide composition(s) may be placed, and preferably suitably aliquoted. Where a second tau- or tau protease-specific primer composition is also provided, the kit may also contain a second distinct container means into which this second primer composition may be placed. Alternatively, the plurality of tau- or tau protease-specific oligonucleotide compositions may be prepared in a single formulation, and may be packaged in a single container means, such as a vial, flask, syringe, test tube, ampoule, or other suitable container means.

The various kits of the present invention will also typically include a means for containing the vial(s) contained therein in close confinement for commercial sale, such as, e.g., injection or blow-molded plastic containers, boxes, or other suitable commercial packaging, into which the desired vial(s) and/or reagent or kit components are retained. Likewise, the kits of the present invention also preferably comprise instructions for using the items contained within such kits in the real-time PCR based assays described herein, including, for example, the real-time PCR/microvolume fluorimetry FRET analyses facilitated by instrumentation such as the Roche LightCycler® platform.

Tau Protease-Specific Oligonucleotide Amplification Primers

In the practice of the invention, forward and reverse amplification primers for use in the amplification of polynucleotides that encode tau protein (and in particular, tau peptides and protein fragments possessing tau protease activity), preferably comprise at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 or more contiguous nucleic acids from any one of the "forward" oligonucleotide primer sequences disclosed in SEQ ID NO:20 or the "reverse" oligonucleotide primer sequences disclosed in SEQ ID NO:21; or from oligonucleotide sequences that are at least about 90% identical to the "forward" oligonucleotide primer sequence disclosed in SEQ ID NO:20 or the "reverse" oligonucleotide primer sequence disclosed in SEQ ID NO:21; or even from oligonucleotide sequences that are at least about 95% identical to the "forward" oligonucleotide primer sequence disclosed in SEQ ID NO:20, or the "reverse" oligonucleotide primer sequence disclosed in SEQ ID NO:21.

Likewise, the primer compositions preferred for the practice of the amplification methods of the present invention may consist of a nucleic acid sequence that is about 90% identical to a contiguous nucleic acid sequence of about 6, about 7, about 8, about 9, about 10, about 11, about 12, about 13, about 14, about 15, about 16, about 17, about 18, about 19, or about 20, or more nucleotides as disclosed in SEQ ID NO:20 and SEQ ID NO:21.

In other embodiments, the primer compositions preferred for the practice of the invention may consist essentially of a nucleic acid sequence that is at least about 6, at least about 7, at least about 8, at least about 9, at least about 10, at least about 11, at least about 12, at least about 13, at least about 14, at least about 15, at least about 16, at least about 17, at least about 18, at least about 19, or at least about 20 or more contiguous nucleic acids selected from any one of the oligonucleotide sequences disclosed in SEQ ID NO:20 or SEQ ID NO:21.

Tau- and Tau Protease-Specific Polynucleotide Amplification Kits

The present invention also provides kits for amplifying mammalian DNA, and in particular, DNAs comprising one or more tau- or tau protease-encoding polynucleotides. Such kits typically comprise two or more components necessary for amplifying mammalian DNA, and such components may be compounds, reagents, containers and/or equipment. For example, one container within a kit may contain a first primer, while a second container within the kit may comprise a second primer. A third container within the kit may contain a set of hybridization probes, or one or more fluorescent probes for labeling the probes. In addition, the kits of the invention may also comprise instructions for use, e.g., instructions for using the primers in amplification and/or detection reactions as described herein, as well as one or more fluorescent molecules, or other reagents as may be necessary, including for example, but not limited to, buffers enzymes, polymerases, RNases and such like.

The invention provides one or more tau or tau-protease-specific oligonucleotide compositions together with one or more excipients, buffers carriers, diluents, adjuvants, and/or other components, as may be employed in the formulation of particular tau- or tau protease-specific oligonucleotide assay reagents, and in the preparation of diagnostic tools. In certain embodiments the invention provides amplification kits for the amplification of polynucleotides that encode peptide or protein fragments of tau protein that possess serine protease activity in vitro and/or in vivo.

Methods for Detection of Polynucleotides Encoding a Tau Protease Active Fragment The invention provides for methods of identifying mammalian polynucleotide sequences that encode one or more tau protease-active fragments in a sample. The invention also provides methods and compositions for specifically detecting in a sample a polynucleotide that encodes a tau protein- (and, more specifically, a polynucleotide that encodes one or more tau protease active fragments), and particularly in a clinical or biological specimen obtained from a human.

The invention further provides methods for specifically detecting a polynucleotide sequence in a sample that encodes a truncated tau protein, a mutated tau protein, or a peptide or polypeptide fragment of a tau protein that possesses serine protease activity in vitro and/or in vivo. These methods preferably utilize the primer and probe compositions and kits disclosed herein for detecting PCR amplification products using a tau-specific target sequence, and particularly for detecting and quantitating such amplification products using FRET, and subsequent melting curve analysis.

In one embodiment, the invention provides a method for detecting the presence or absence of a tau- or tau protease active peptide-encoding polynucleotide, or a nucleic acid segment that encodes all or a portion of a tau protease, and in particular to a nucleic acid segment that encodes a protein that comprises, consists essentially of, or alternatively, consists of, a peptide that is at least about 98% identical to an at least 30, 40, 50, or 60 contiguous amino acid sequence from one or more of the tau protein amino acid sequences as set forth in any one of SEQ ID NO:1, SEQ ID NO:2, SEQ ID NO:3, SEQ ID NO:4, SEQ ID NO:5, or SEQ ID NO:6. In certain aspects, one or more biological samples may be taken from an individual, and screened for the presence of such a sequence. In particular embodiments, the sample may be screened for the presence of one or more peptide fragments that possess serine protease activity, including, for example, the truncated tau peptides disclosed in SEQ ID NO:1, SEQ ID NO:2, SEQ ID NO:3, SEQ ID NO:4, SEQ ID NO:5, or the full-length Tau 4R2N trimer sequence disclosed in SEQ ID NO:6.

In one aspect of the invention, there is provided a method for detecting the presence or absence of a tau protease-specific polynucleotide, and in particular, a polynucleotide that encodes a tau protease from within a plurality of polynucleotides comprised within a sample. In certain embodiments, the sample is a biological sample obtained from a mammal. Preferably the sample is obtained from a human being.

In particular application, these methods include a real-time PCR-based amplification step, which generally involves performing at least one cycling step (which includes at least a first "amplifying" step and at least a first "hybridizing" step). This amplifying step includes contacting the sample with a pair of tau- or tau protease-specific oligonucleotide primers to produce an amplification product if a tau or tau protease target polynucleotide was originally present in the sample. (If no target polynucleotide was originally present in the sample, then no specific product amplification would occur during the PCR process).

The hybridizing step typically includes contacting the sample that results from the amplifying step with a pair of tau-specific oligonucleotide probes. Generally, the first and second members of the pair of tau-specific oligonucleotide probes hybridizes to the amplification product within no more than about four or five nucleotides of each other. A first probe of the pair of detection probes is typically labeled with a donor fluorescent moiety and a second probe of the pair of detection probes is typically labeled with a corresponding acceptor fluorescent moiety. These detection probes and the moieties that may be operably linked to them for use in the hybridizing step have been described in more detail hereinabove.

The invention also concerns the use of one or more of tau- or tau protease-specific oligonucleotide amplification primer or detection probe sets described herein in the detection of a mutation in a population of polynucleotides suspected of comprising at least a first polynucleotide that encodes a mammalian tau polypeptide, and in particular, in the detection of a mutation in a population of polynucleotides suspected of comprising at least a first polynucleotide that encodes a mammalian peptide or polypeptide that possesses tau protease activity in vitro and/or in vivo.

Fret-Based Protease Detection Assay

Another aspect of the present Mention is the use of fluorescent resonance energy transfer (FRET)-based detection assays for detecting one or more tau polynucleotides or tau polypeptides in accordance with the present invention.

In FRET-based detection assays, a donor fluorescent moiety of a first probe and an acceptor fluorescent moiety of a second probe is utilized in which the presence of a FRET signal is indicative of the presence of the target compound in the sample being assayed. Conversely, the absence of a FRET signal is usually indicative of the absence of the target compound in the sample being assayed.

The FRET assay peptide substrate is composed of nine amino acids surrounding the autoproteolytic cut site after Lys 340 in tau 4R2N with the fluorescent molecule methylcoumarin (MCA) at the amino terminus and the fluorescence quenching molecule dinitrophenol (DNP) at the C-terminus using an additional Lys at the C-terminus to conjugate it to the peptide: MCA-GGQVEVKSE-{Lys(DNP} (SEQ ID NO:18). The concept is that when tau protease cuts the peptide the quench is dissociated from the fluor such that there is a detectable increase in the fluorescence signal in the assay. This assay can be used to monitor tau protease activity to screen small molecule compounds, peptides or antibodies that modulate tau protease activity. This assay can also be used to characterize enzyme kinetics and optimize the buffer conditions for tau protease. This assay can also be used to monitor the activity of different constructs and oligomer preparations of tau protease. The FRET peptide can be optimized by adjusting the length of the peptide substrate separating the fluor from the quench. Additional FRET peptides can be made to monitor tau protease activity based on other cleavage sites of tau protease.

BRIEF DESCRIPTION OF THE DRAWINGS

Reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates.

The following drawings form part of the present specification and are included to demonstrate certain aspects of the present invention. The invention may be better understood by reference to the following description taken in conjunction with the accompanying drawings, in which like reference numerals identify like elements, and in which:

FIG. 6A: Purified tau 4R2N monomer, dimer and trimer preparations were incubated for 0, 2 and 16 hr at 37° C. in buffer (25 mM Tris-HCl pH 7.4) and run on a 4-20% polyacrylamide Tris-HCl gel with sample buffer with reductant. From left to right, Lanes 1-3: monomer, 0, 2, 16 hr incubation; Lanes 4-6: dimer 0, 2, 16 hr incubation; Lanes 7-9: trimer, 0, 2, 16 hr incubation. The gel was stained with GelCode® Blue Safe (ThermoFisher Scientific) and the protein was transferred to a PVDF membrane (Merck Millipore). Immunoblots were performed using to identify fragments observed from a partial digest of tau 4R2N protein using an antibody specific for the C-terminus, epitope at amino acids 404-441 tau 4R2N (monoclonal T46, Life Technologies, Grand Island, N.Y., USA). The blot was stripped and reprobed with an antibody to the N-terminus, epitope at amino acids 83-120 tau 4R2N (monoclonal antibody T14, Life Technologies). FIG. 6B: The molecular weight of each fragment was determined using the tau oligomer ladder as a standard, and fitting the migration to the $_{log}$Mw. Matching the fragment pairs that summed to the molecular weight of the tau 4R2N MW of 45.8 KDa enabled identification of KS sites that were cut during the partial digest. In addition, fragments consistent with cutting at KT sites were also identified using this method. Thus, the tau cut site motifs identified from the mass spec and western blot were P1-K-(S, T or I)-P1';

(SEQ ID NO: 1)
MSKDGTGSDDKKAKGADGKTKIATPRGAAPPGQKGQANATRIPAKTPPAP

KTPPSSGEPPKSGDRSGYSSPGSPGTPGSRSRTPSLPTPPTREPKKVAVV

RTPPKSPSSAKSRLQTAPVPMPDLKNVKSKIGSTENLKHQPGGGKVQIIN

KKLDLSNVQSKCGSKDNIKHVPGGGSVQIVYKPVDLSKVTSKCGSLGNIH

HKPGGGQVEVK.

Figure 8:
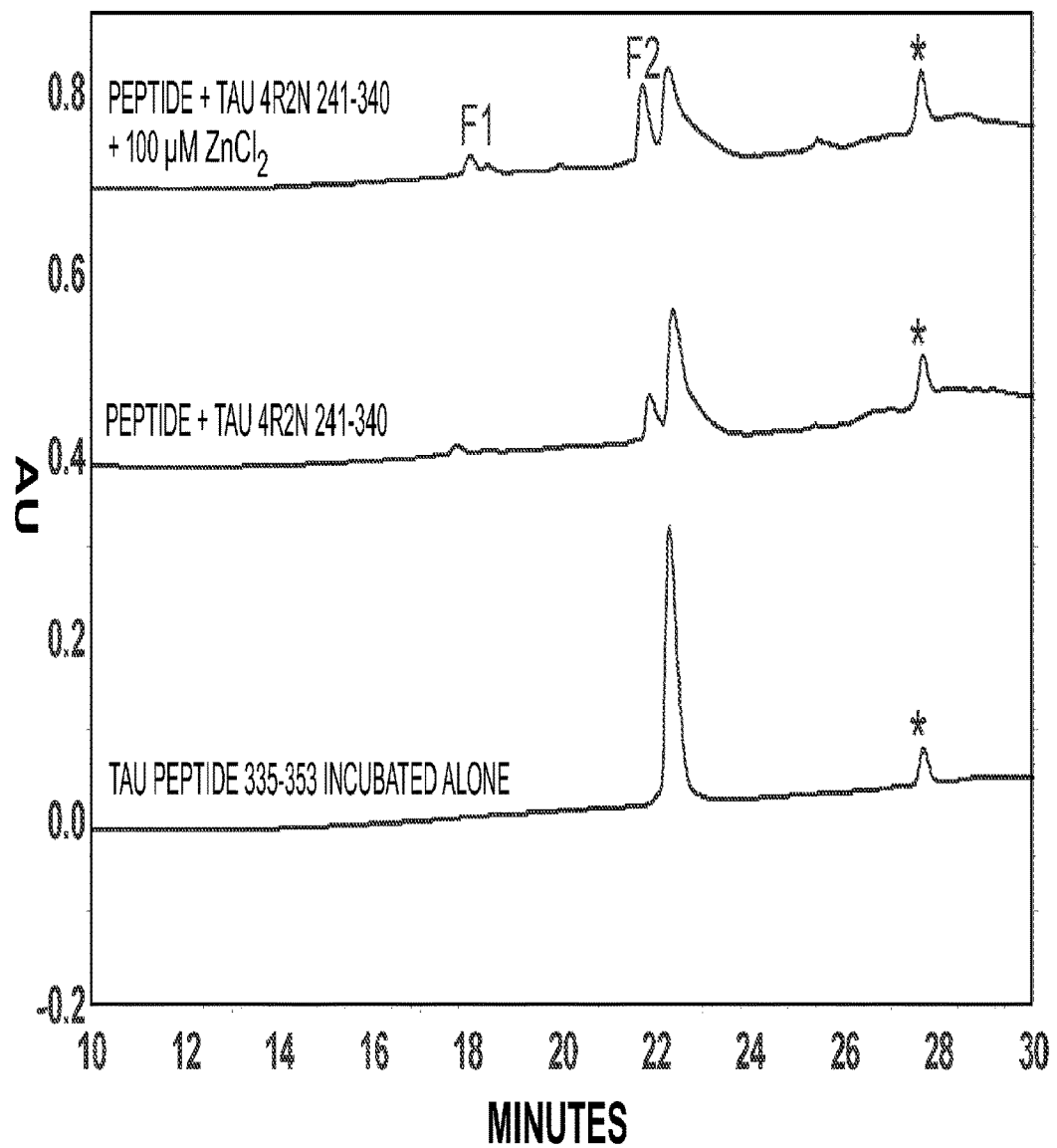

Cleavage of the peptide substrate for tau protease, Tau 4R2N (amino acids 335-353) GQVEVKSEKLDFKDRVQSK (SEQ ID NO.19), was used to monitor activity using reverse-phase HPLC. The lower trace shows the peptide incubated in reaction buffer in the absence of TP-210, and the upper trace shows the peptide incubated with TP-210. The large peak in the lower trace indicated intact peptide was greatly diminished in the upper trace and replaced with two smaller peaks F1 and F2 that represent fragments generated by TP-210. The asterisk indicates an artifact peak that is derived from a non-specific contaminant that was used as a marker. Twelve microgram of tau 4R2N peptide (amino acids 335-353) was incubated with or without oligomerized TP-210 overnight at 37° C. and analyzed by reverse phase HPLC (SystemGold® 32Karat™ LC-CE System, Beckman Coulter, Inc., (Indianapolis, Ind.)) using a linear gradient of acetonitrile in 0.1% TFA 0-60% acetonitrile on an analytical $C_{18}$ column (12.5 cm×2.1 mm, 5 μm (Supelco);

FIG. 8 demonstrates that the truncated tau protein TP-99 showed protease activity in peptide digest HPLC assays. It was determined that amino acids 241-340, a 99-amino acid fragment (plus an additional initiating methionine necessary for its expression) possessed tau protease activity, thereby further delimiting the proteolytic region of wild-type tau protein. The amino acid sequence of Tau 4R2N 241-340 (TP-99) is shown:

(SEQ ID NO: 3)
MRLQTAPVPMPDLKNVKSKIGSTENLKHQPGGGKVQIINKKLDLSNVQSK

CGSKDNIKHVPGGGSVQIVYKPVDLSKVTSKCGSLGNIHHKPGGGQVEV

K.

Figure 5:
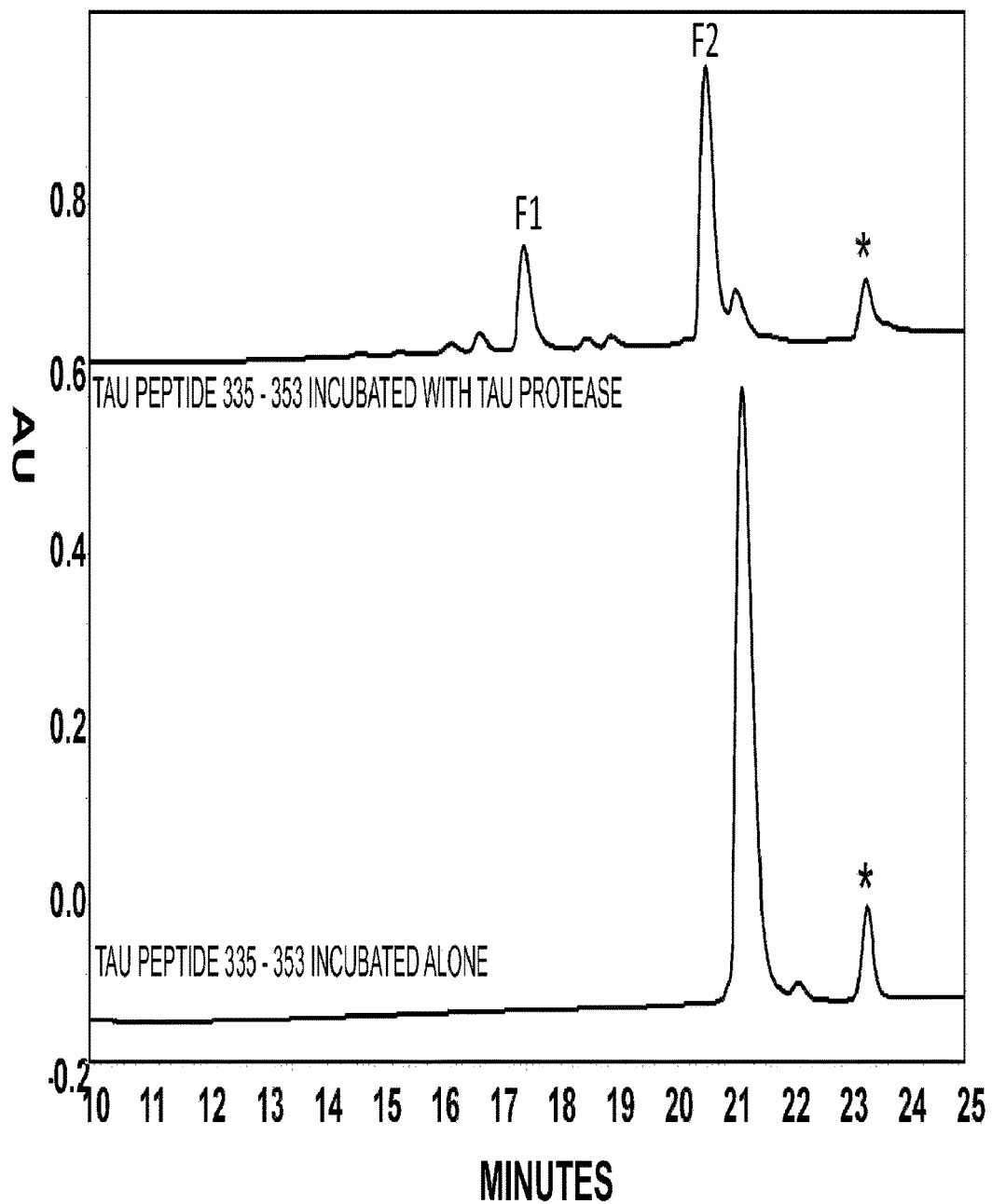
FIG. 5 shows that a peptide fragment of tau protein 4R2N (amino acids 335-353) was cut by tau 4R2N trimer protease. N-terminal sequencing of fragments using mass spectrometry identified autoproteolytic cut sites. In particular, cutting at the Lys340-Ser341 (340KS341) cut site occurred readily. Therefore, a 19-amino acid peptide corresponding to amino acids 335G to 353L of tau protein was synthesized that contained the KS cut site (340KS341). The reaction was monitored by reverse-phase high-pressure liquid chromatography (HPLC). The lower trace shows the peptide alone and the upper trace shows peptide incubated with tau 4R2N trimer protease both of which were incubated overnight at 37° C. In the lower trace, the uncut peptide shows a retention time of approximately 21.25 min. An asterisk marks a non-specific contaminant that was used as a marker. The upper trace shows the two product fragments had retention times of approximately 17.5 (F1) and 20.5 (F2) min. The reaction was more than 90% complete under the reaction conditions tested, and the results definitively demonstrated the ability of tau protease to cut peptides in addition to its autoproteolytic reaction. 10 μg of tau peptide 335-353 (GQVEVKSEKLDFKDRVQSK) (SEQ ID NO:19) was custom synthesized by Genscript (Piscataway, N.J., USA) and 1 mg was dissolved in 1 mL of buffer (25 mM Tris-HCl pH 7.4). 29 μs of peptide was incubated with 11 μg of tau trimer protease in 30 μL buffer 20 hr at 37° C. and analyzed by HPLC [SystemGold® 32Karat™ LC-CE System, Beckman Coulter, Inc., (Indianapolis, Ind.)] using a linear gradient of acetonitrile in 0.1% TFA 0-60% acetonitrile on an analytical $C_{18}$ column (12.5 cm×2.1 mm, 5 μm, (Supelco, Bellefonte, Pa., USA). 30 μg of peptide was incubated without tau protease as a negative control and analyzed with the same method.
Figure 7:
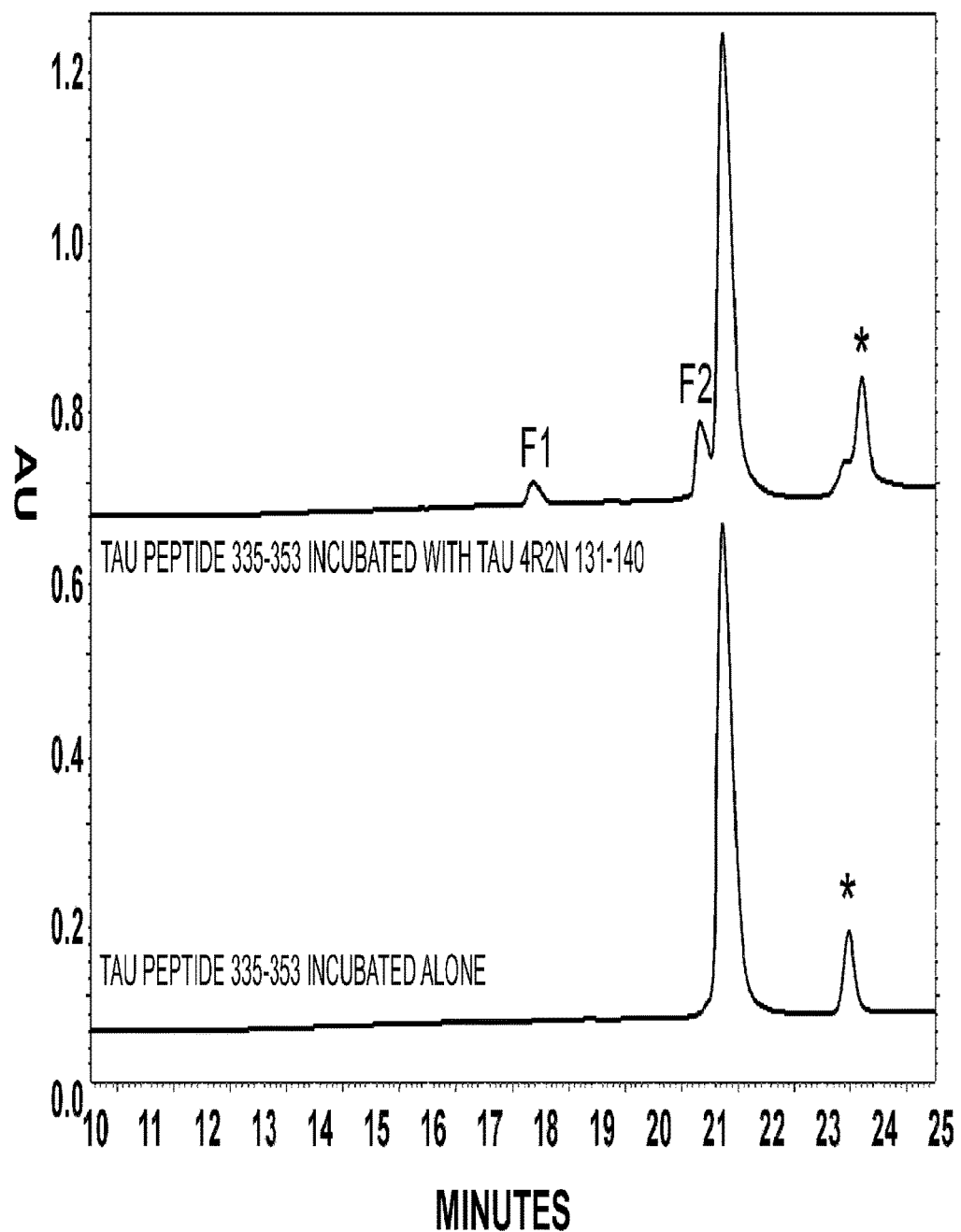
FIG. 7 shows that a 210-aa fragment of tau protein (TP-210; Tau 4R2N 131-340) retained proteolytic activity, thus delimiting the proteolytic region of tau. It was determined that amino acids 131-340, a 210-aa fragment (plus an additional initiating methionine necessary for its expression) possessed tau protease activity. The amino acid sequence of Tau 4R2N 131-340 (TP-210) is shown.
Figure 9A:
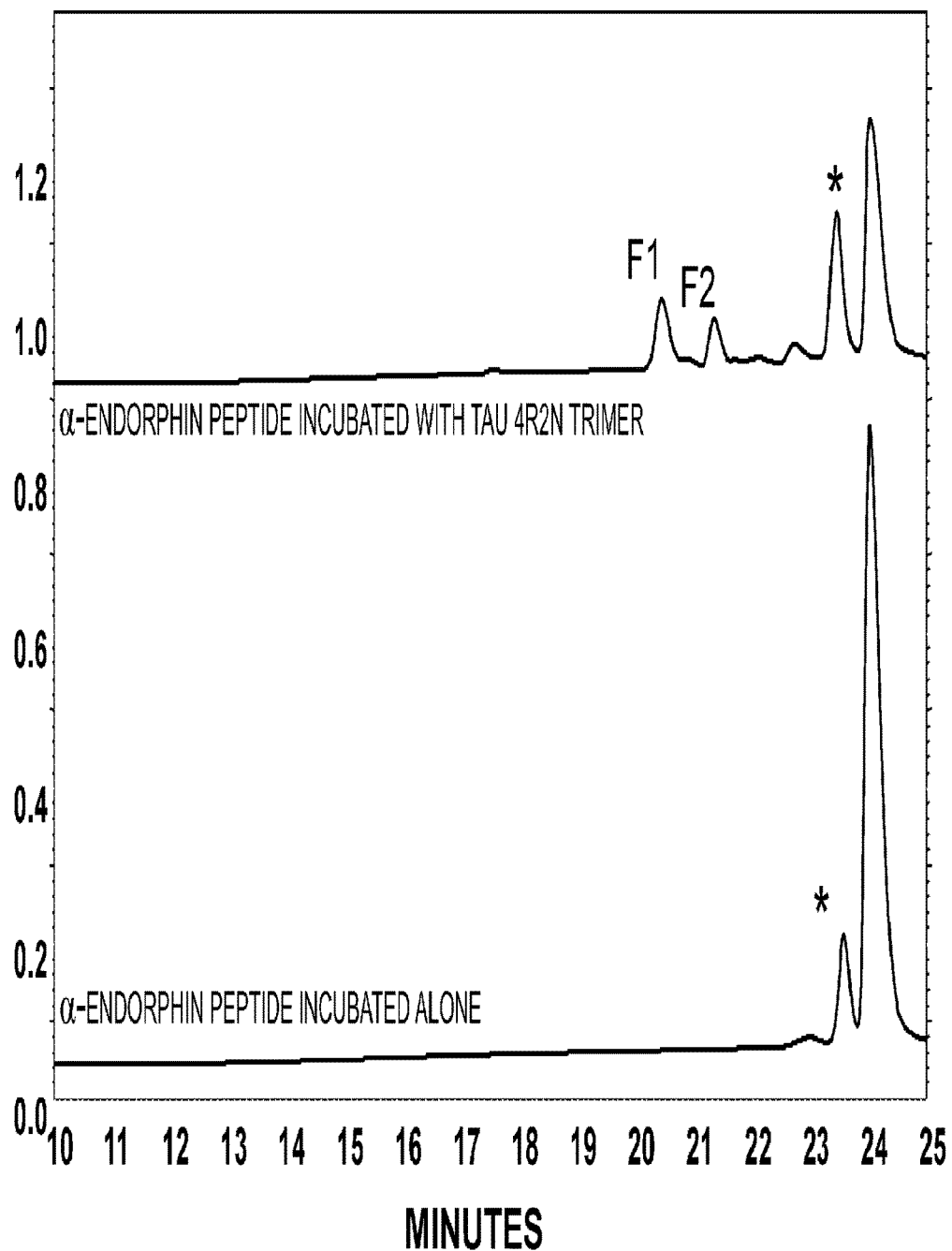
Figure 9B:
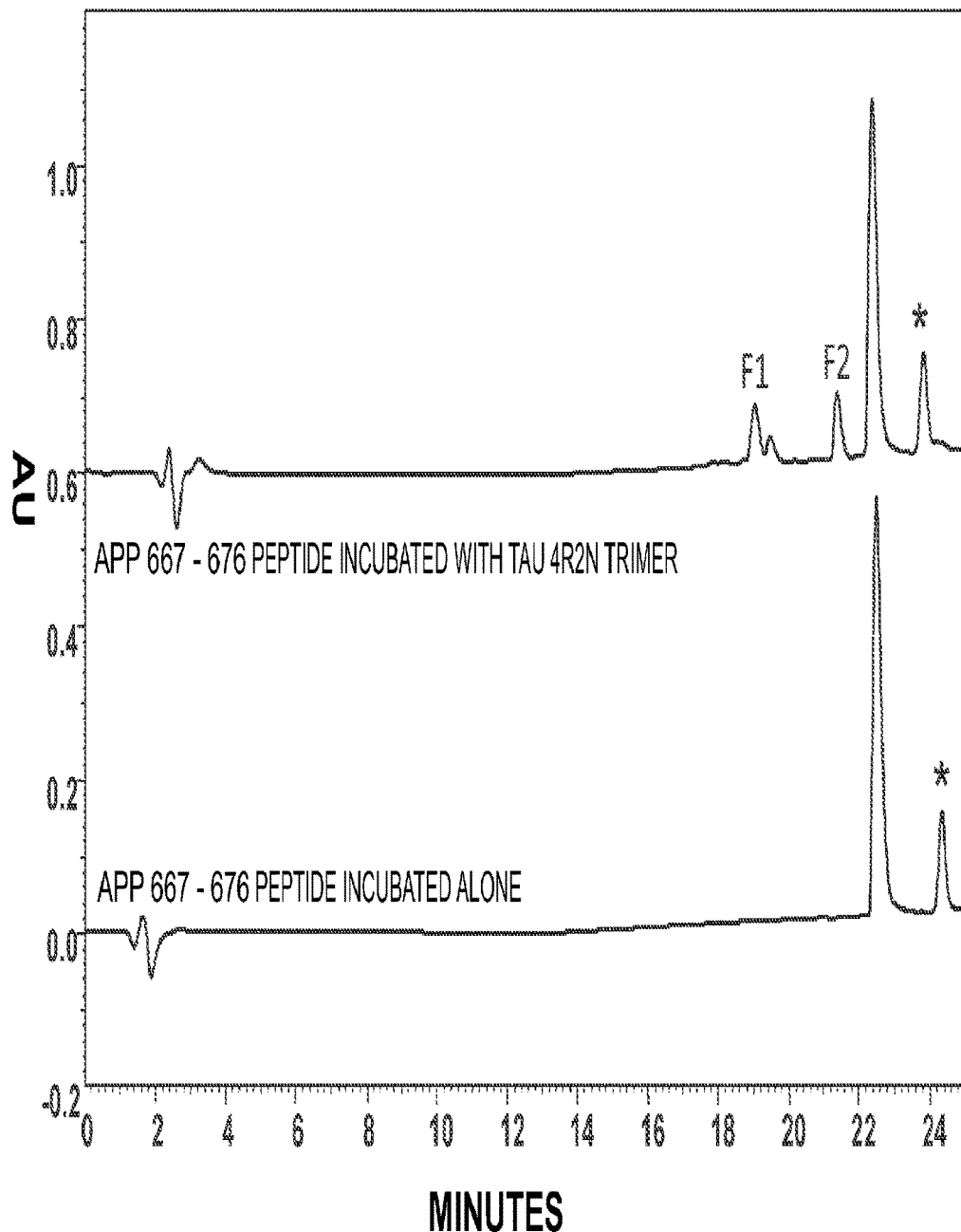
Figure 10:
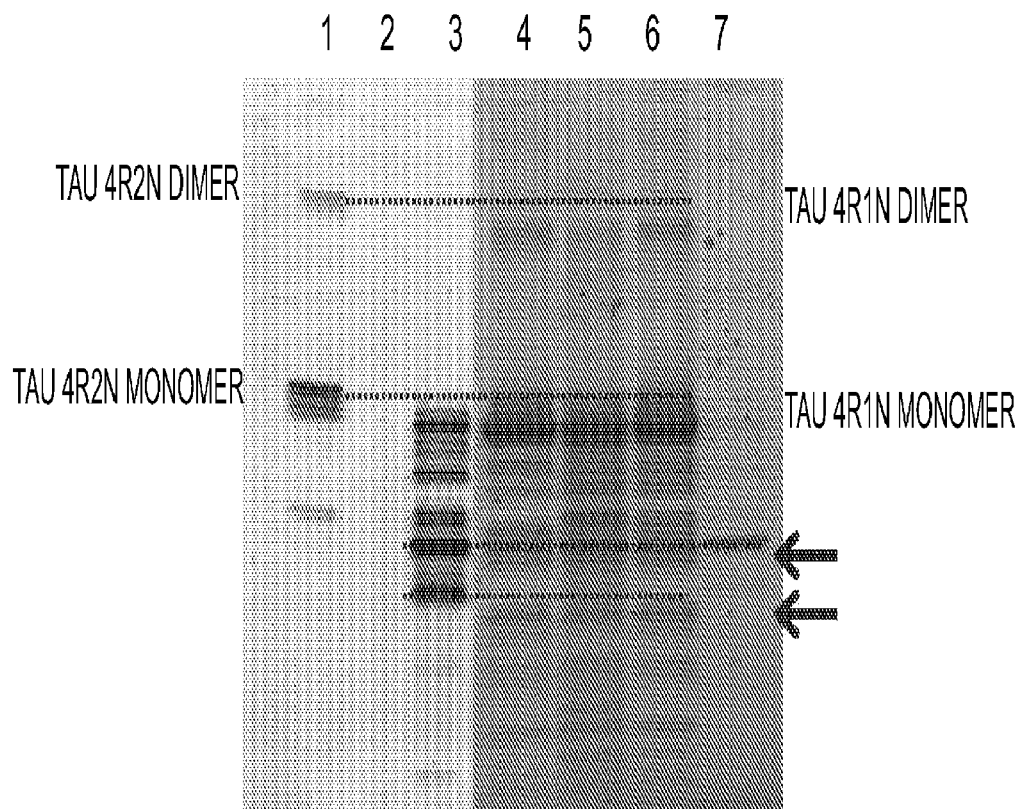
Figure 11:
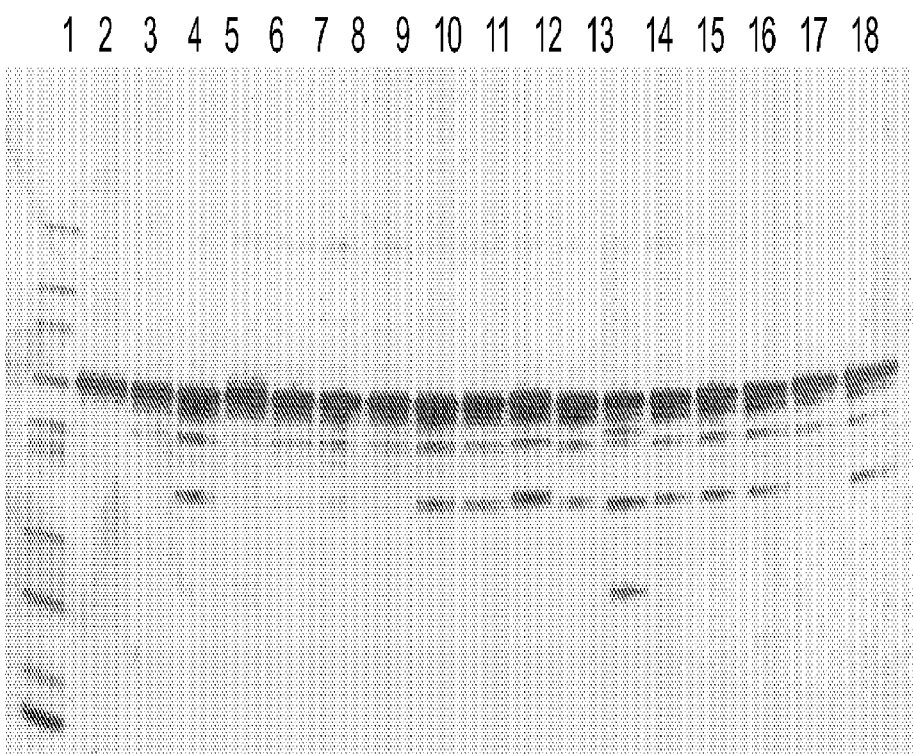
Figure 12:
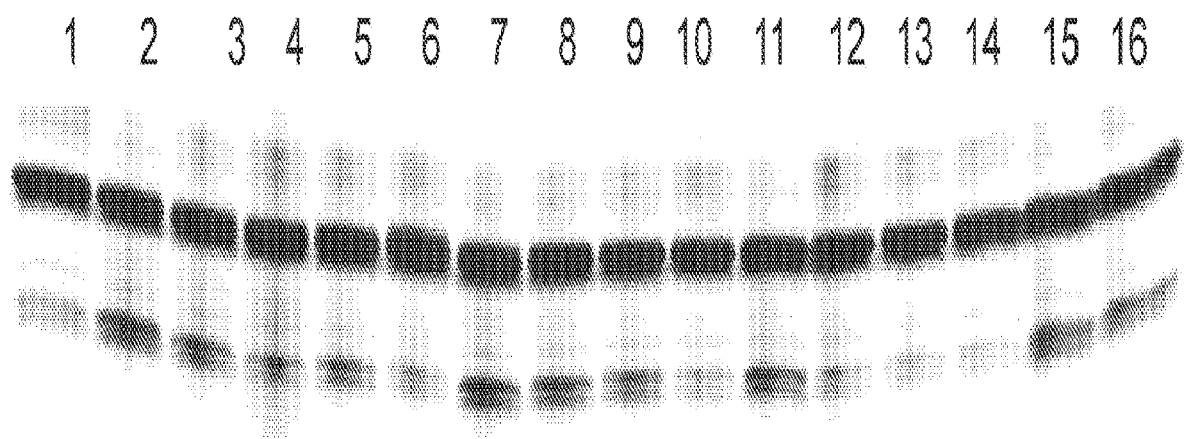
Figure 13:
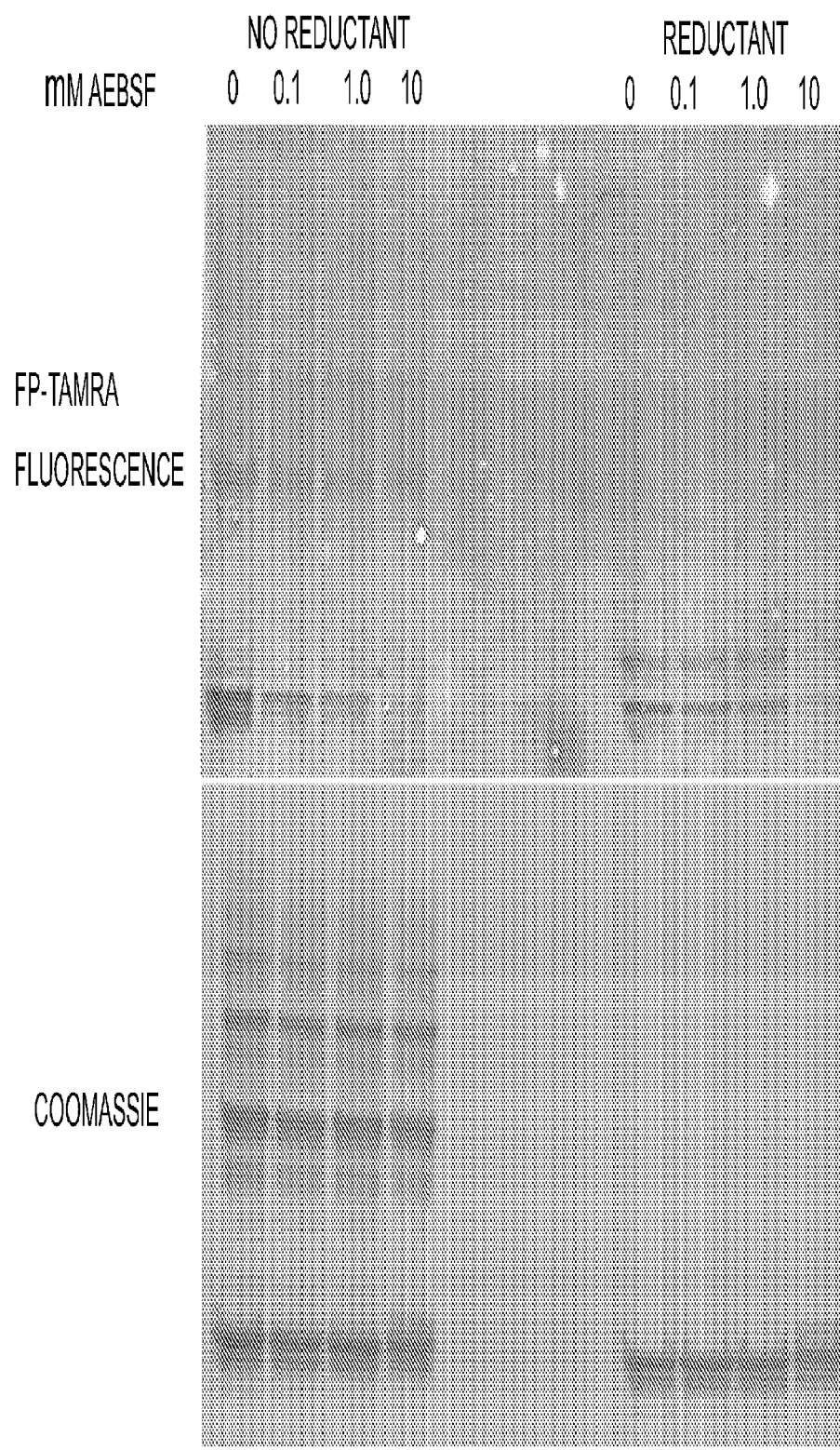
Figure 14A:
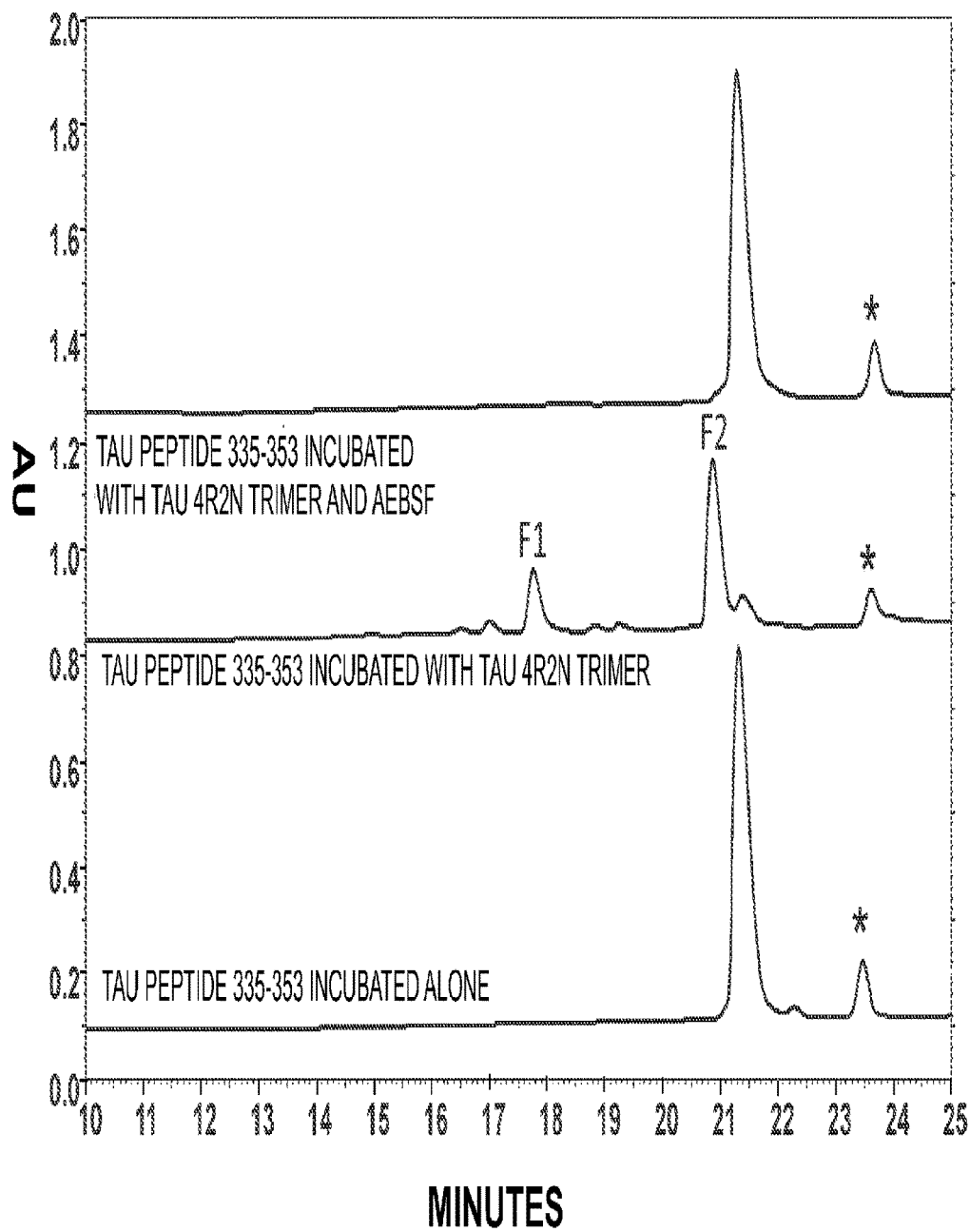
Figure 14B:
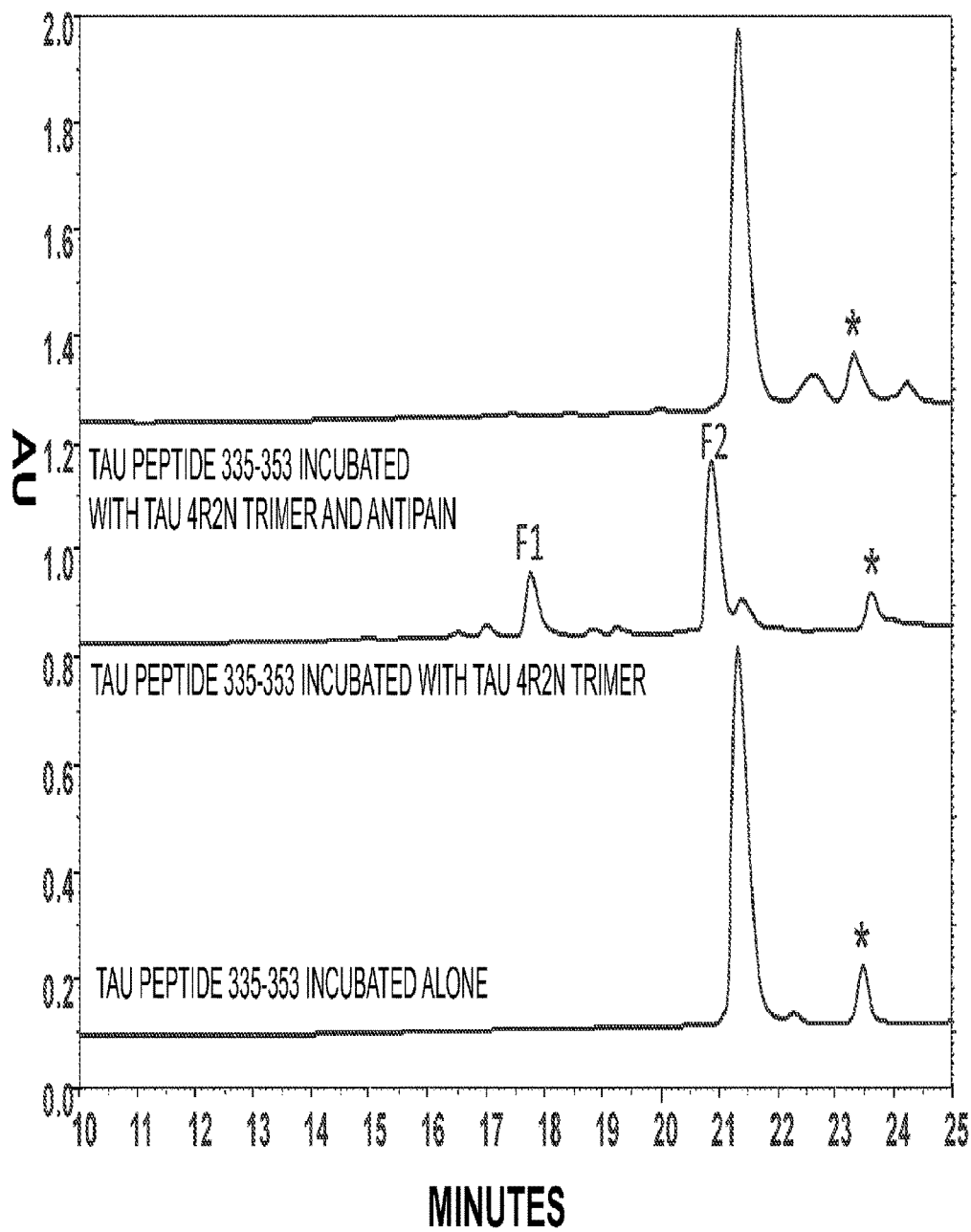
Figure 14C:
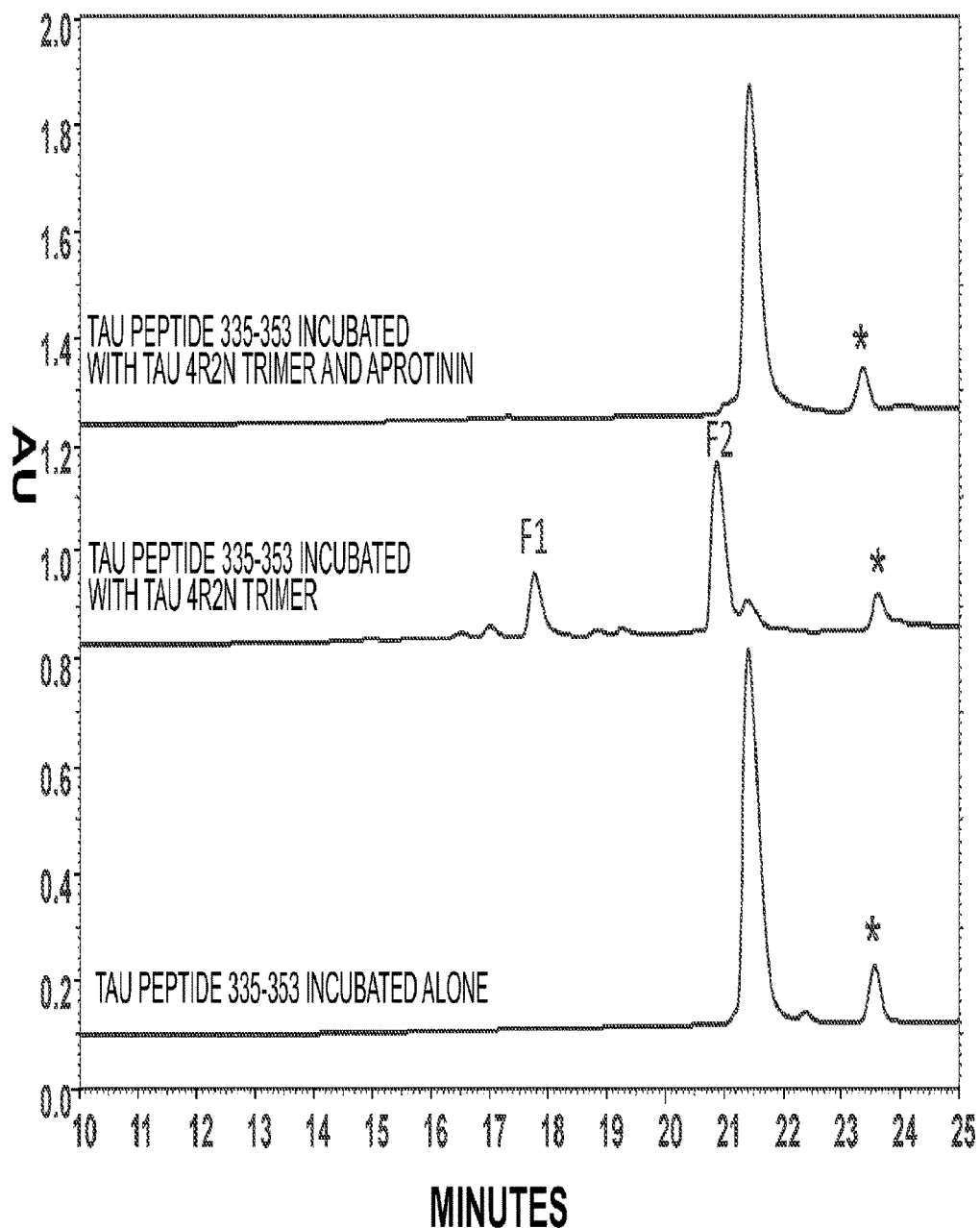
Figure 14D:
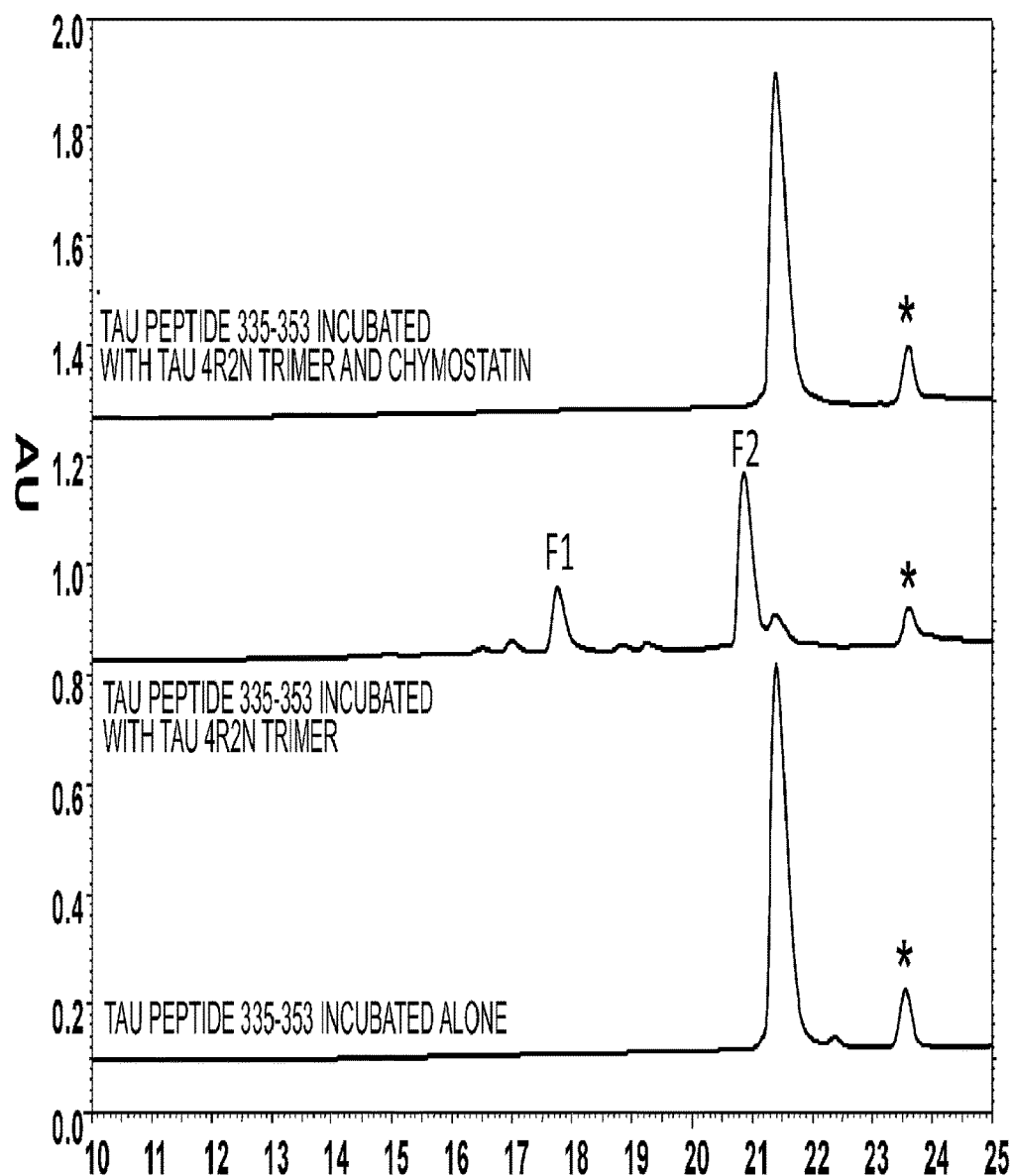
Figure 14E:
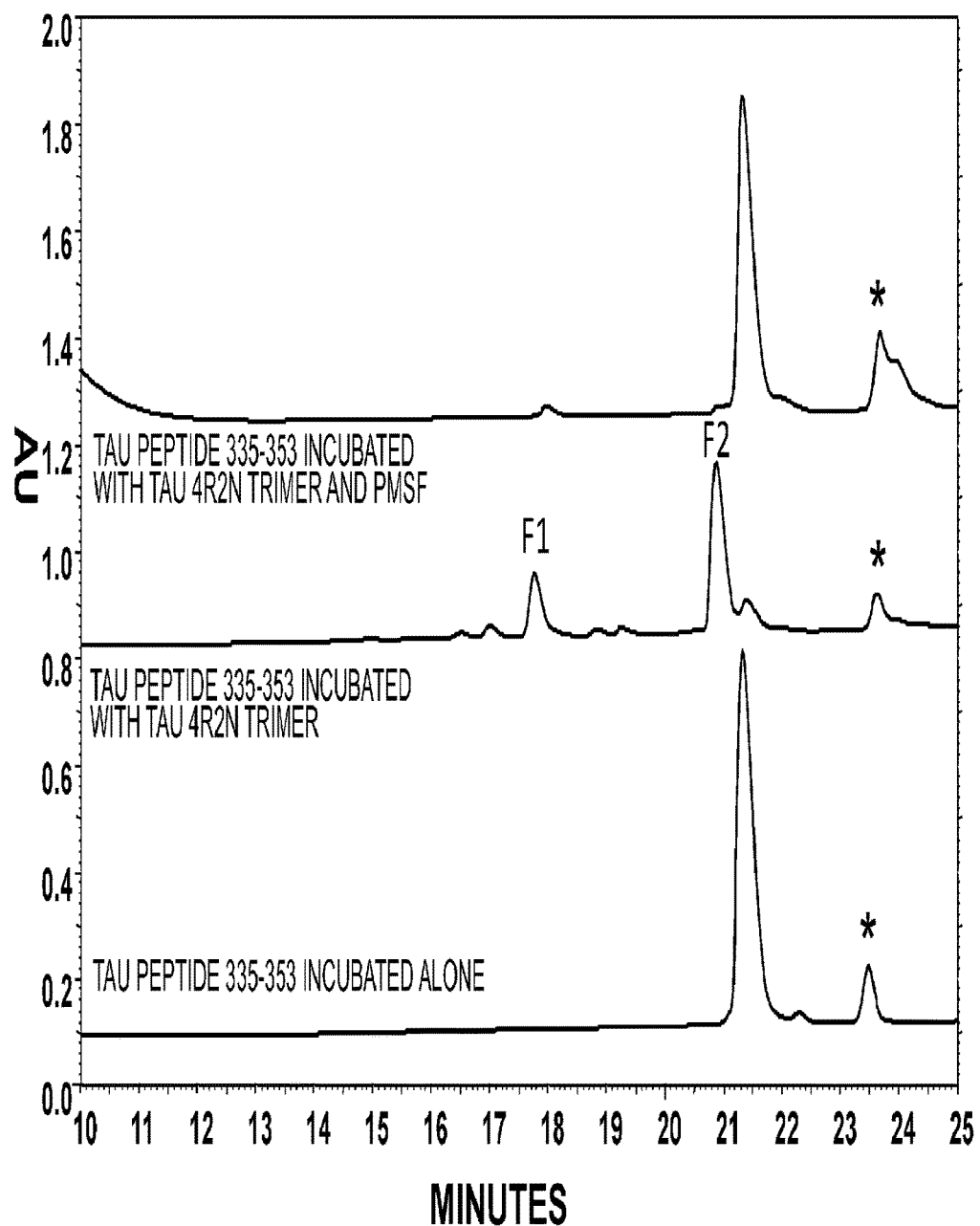
Figure 14F:
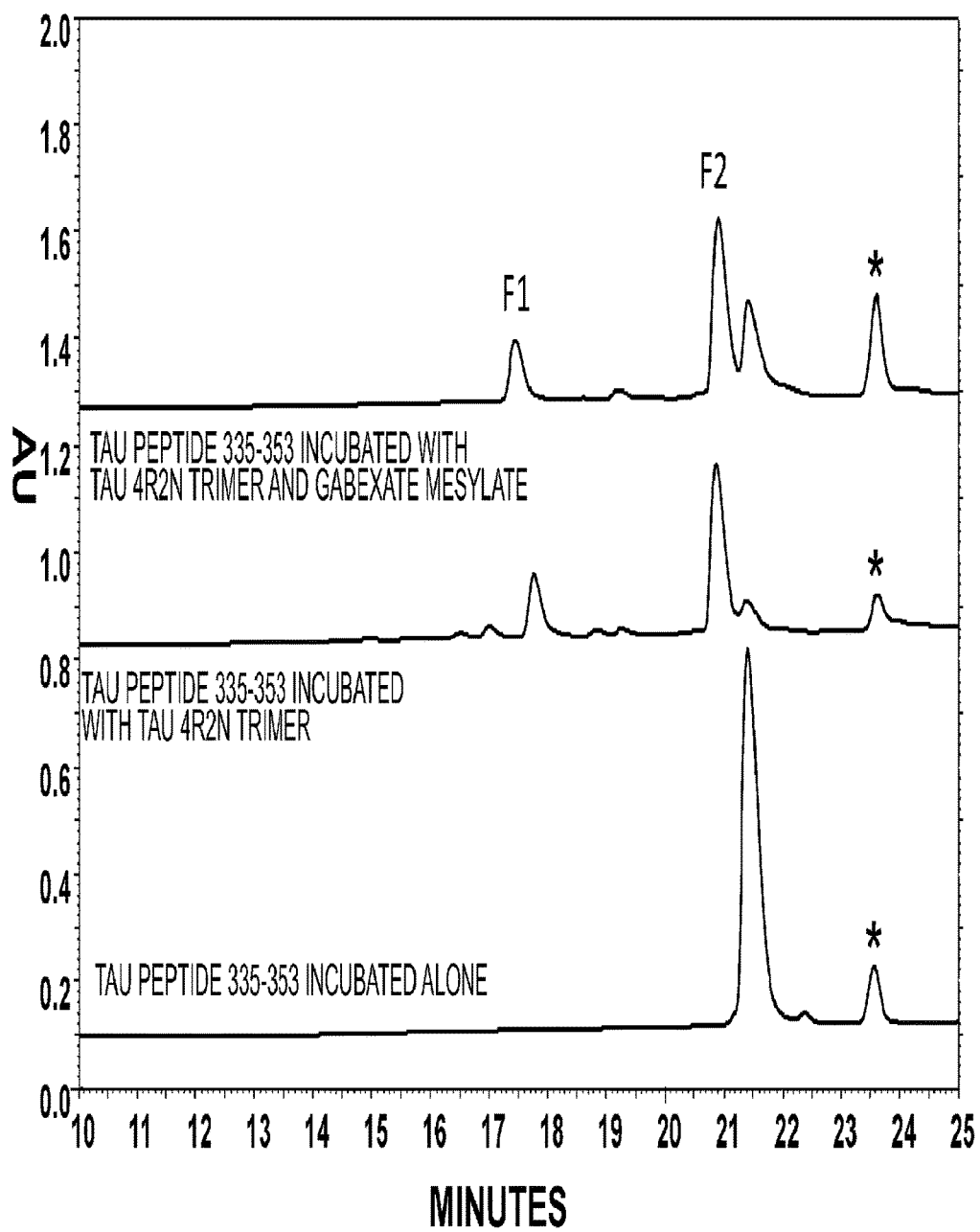
Figure 15:
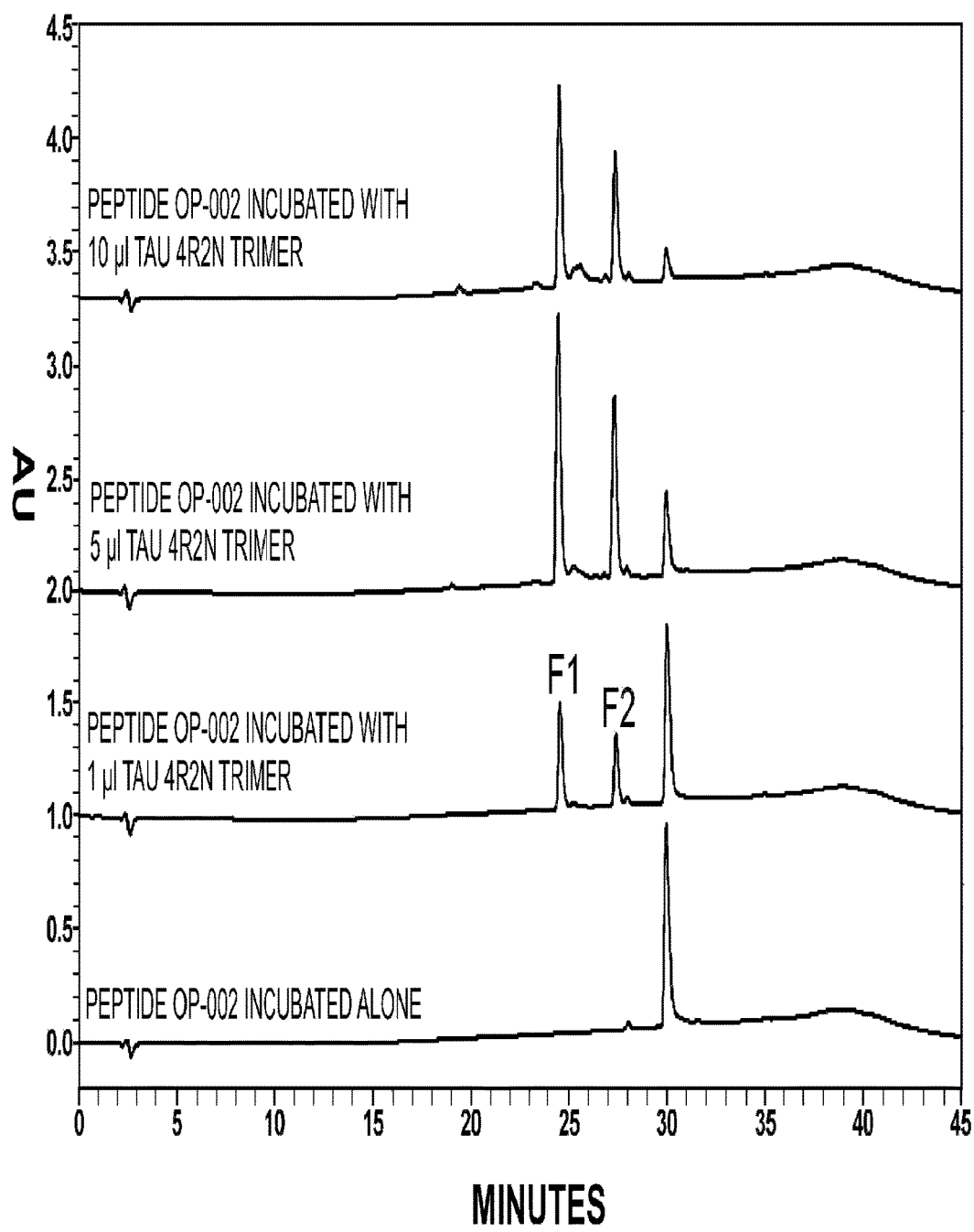
Figure 16:
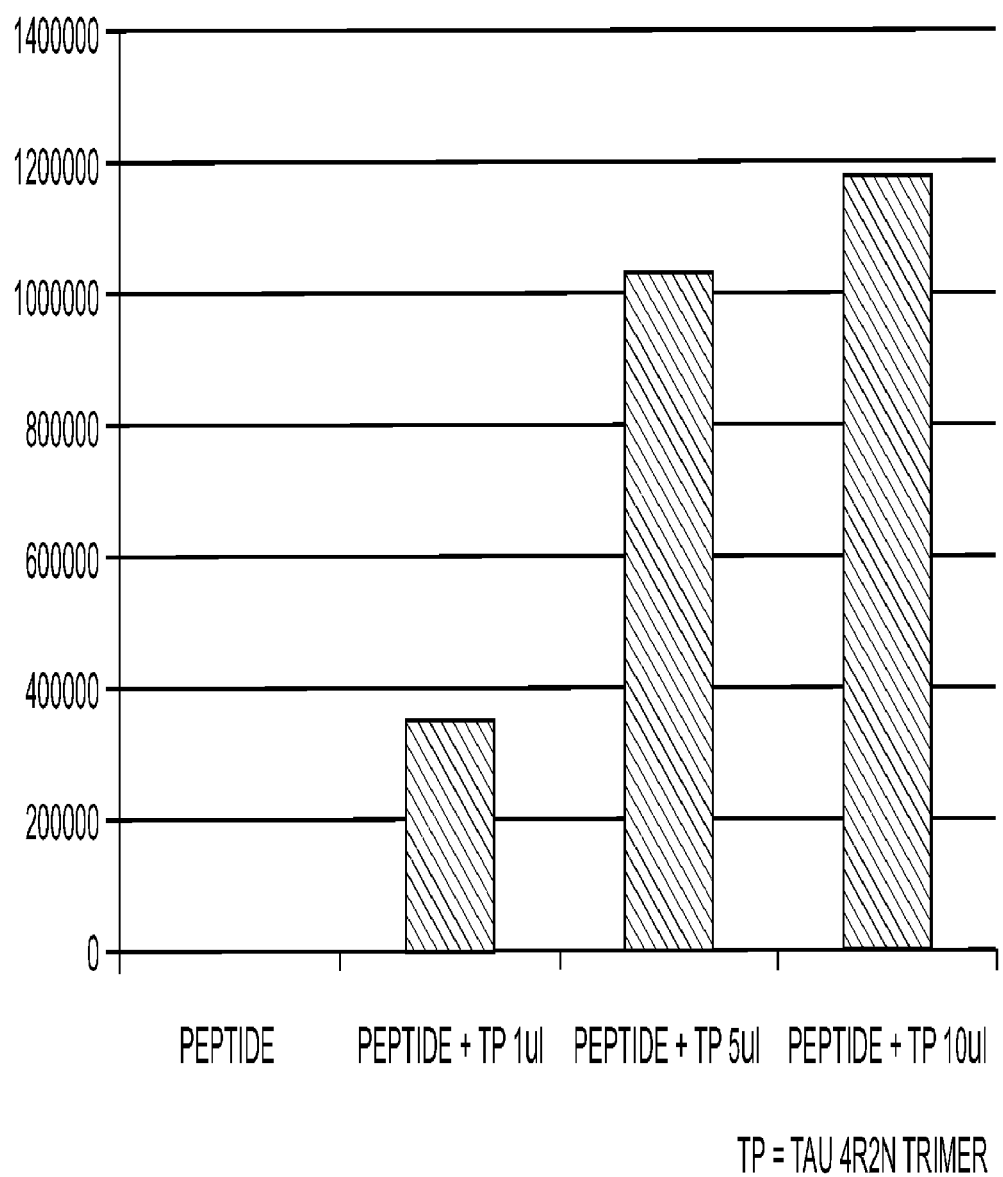
Figure 17:
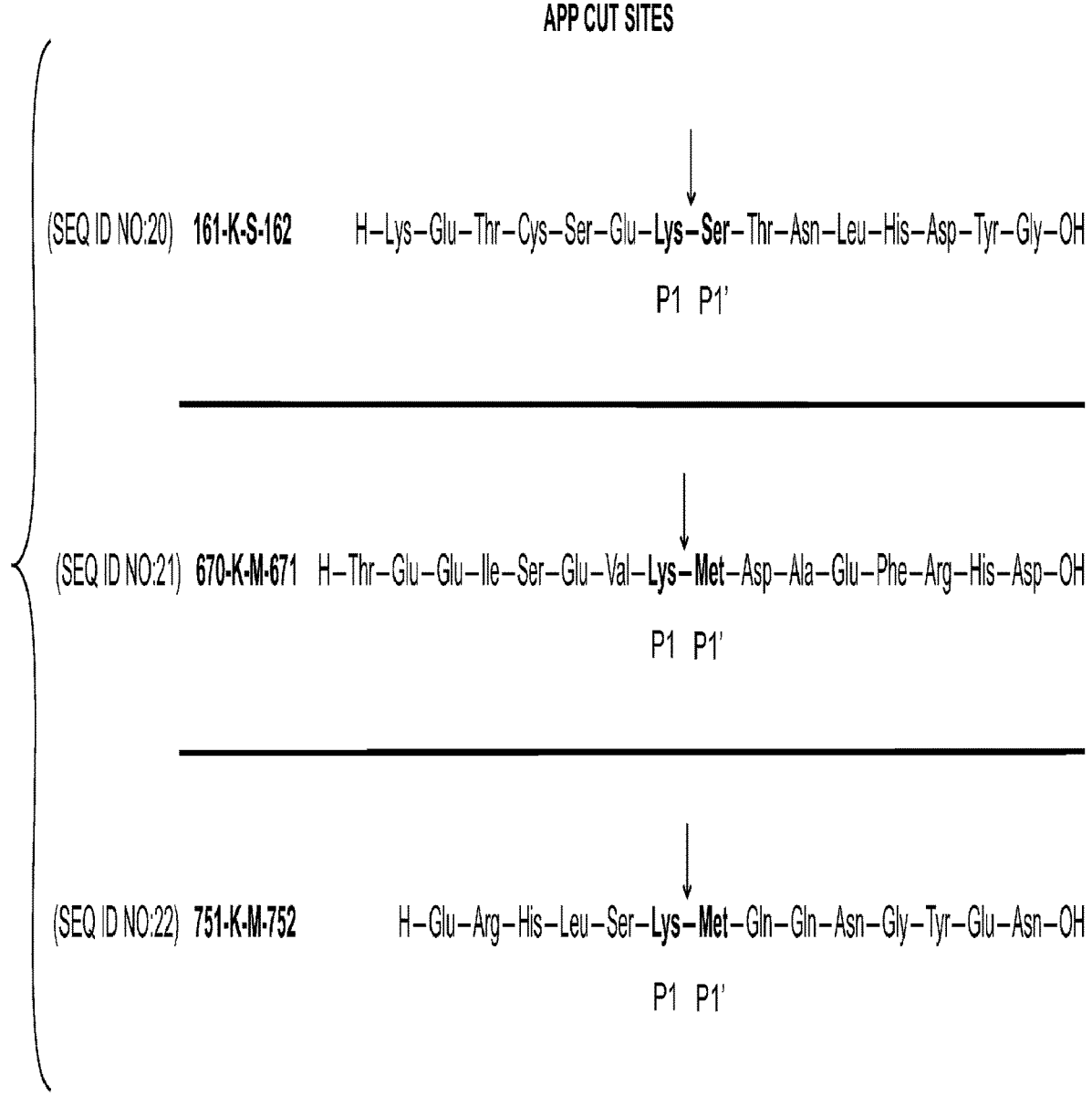
Figure 18:
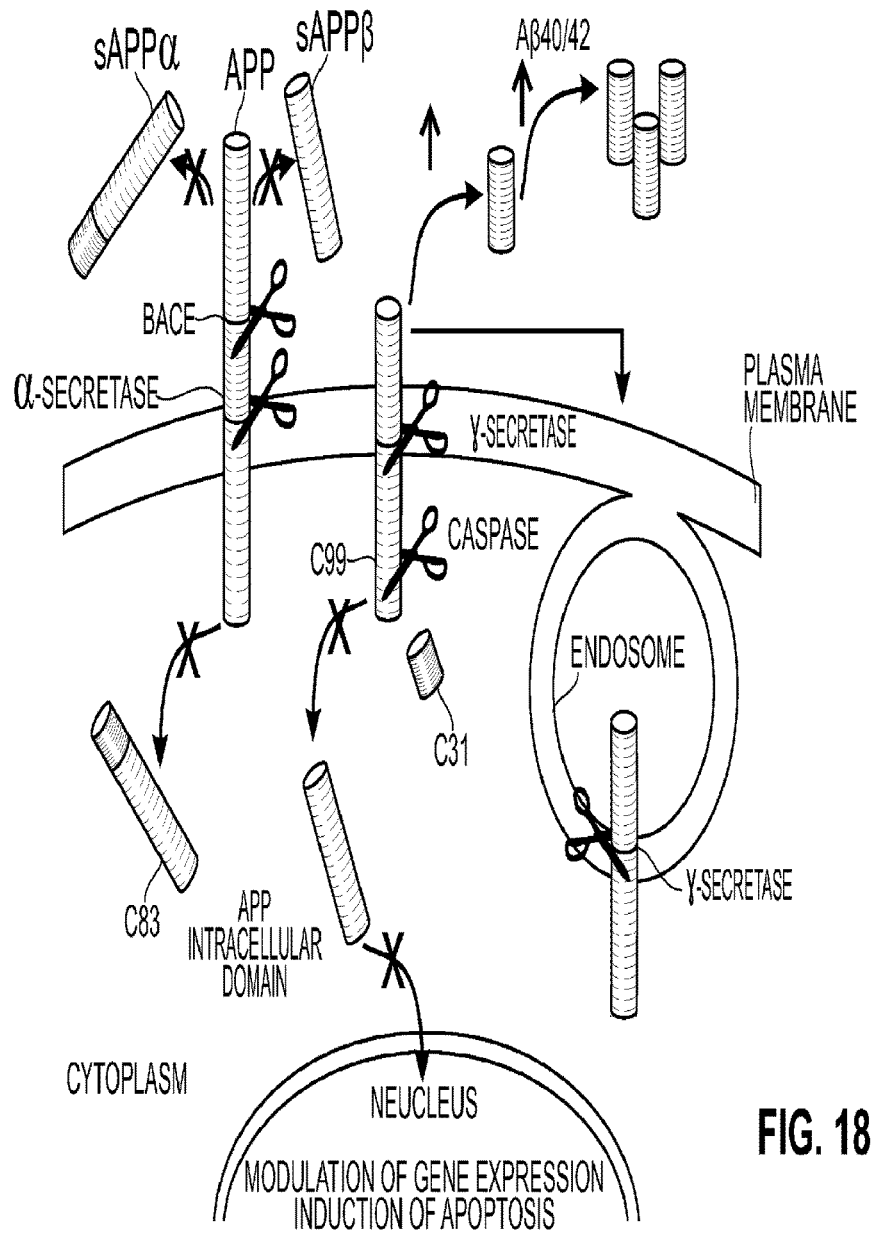
Figure 22:
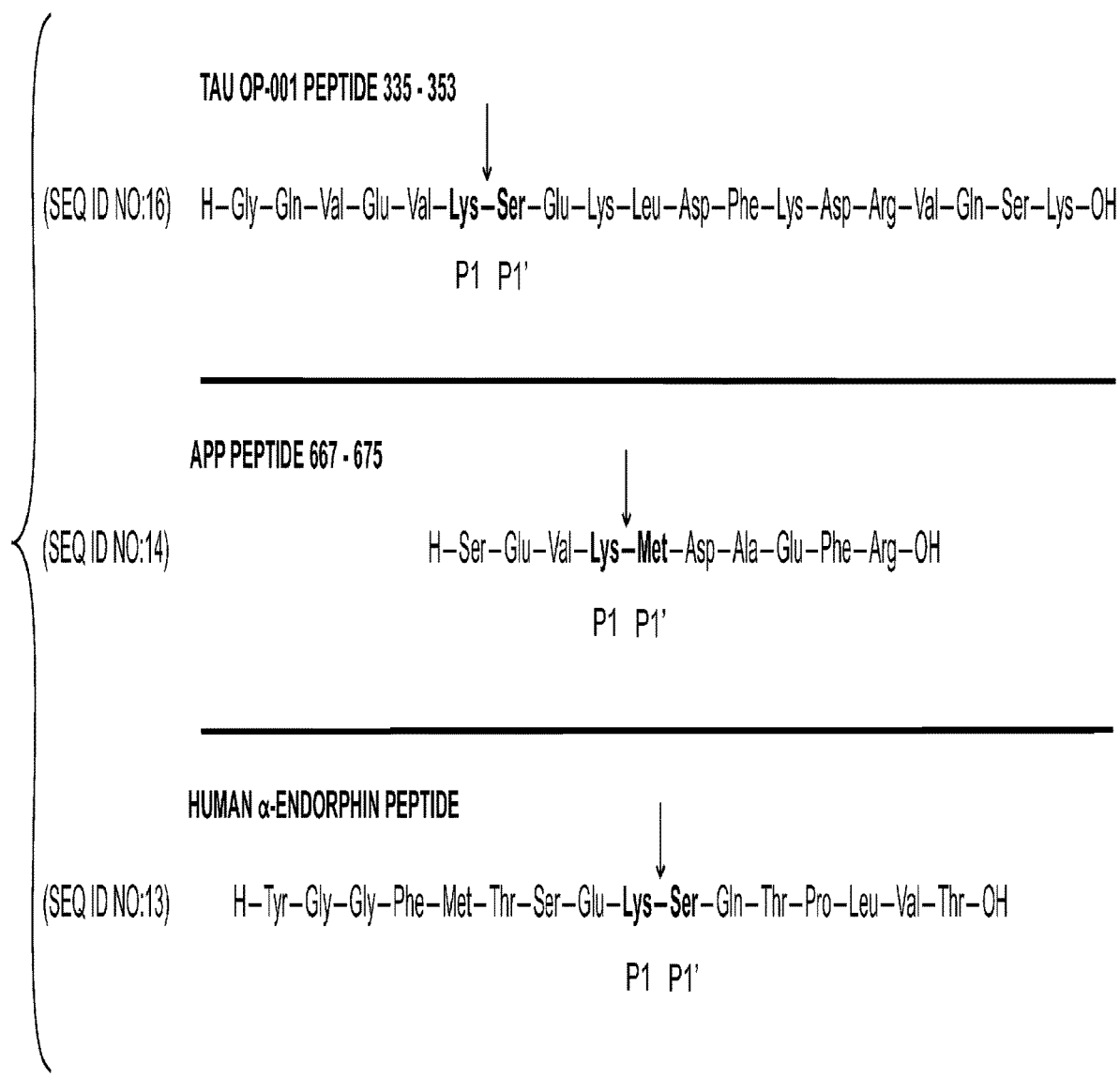
Figures 23A, 23B:
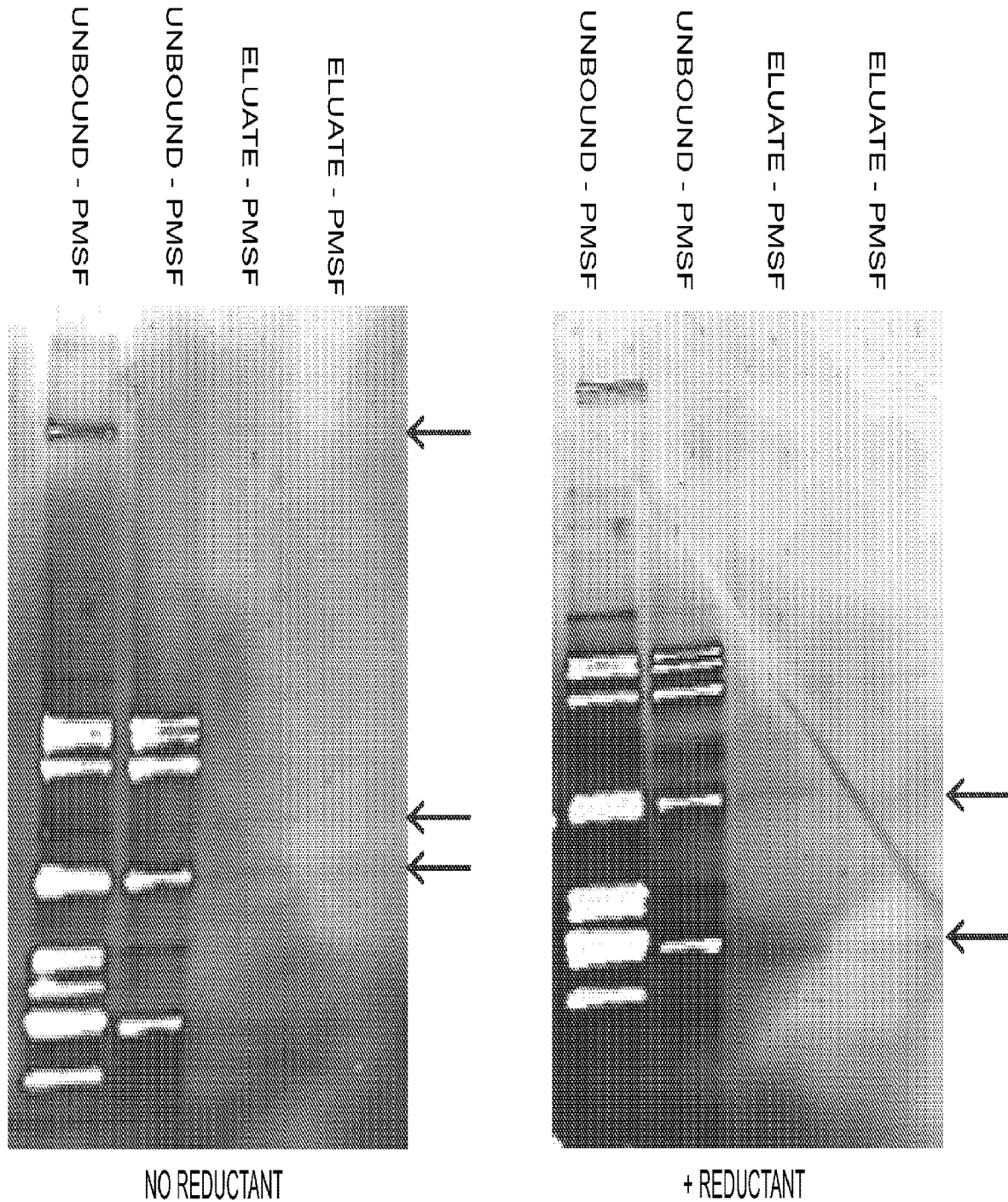
Figure 25:
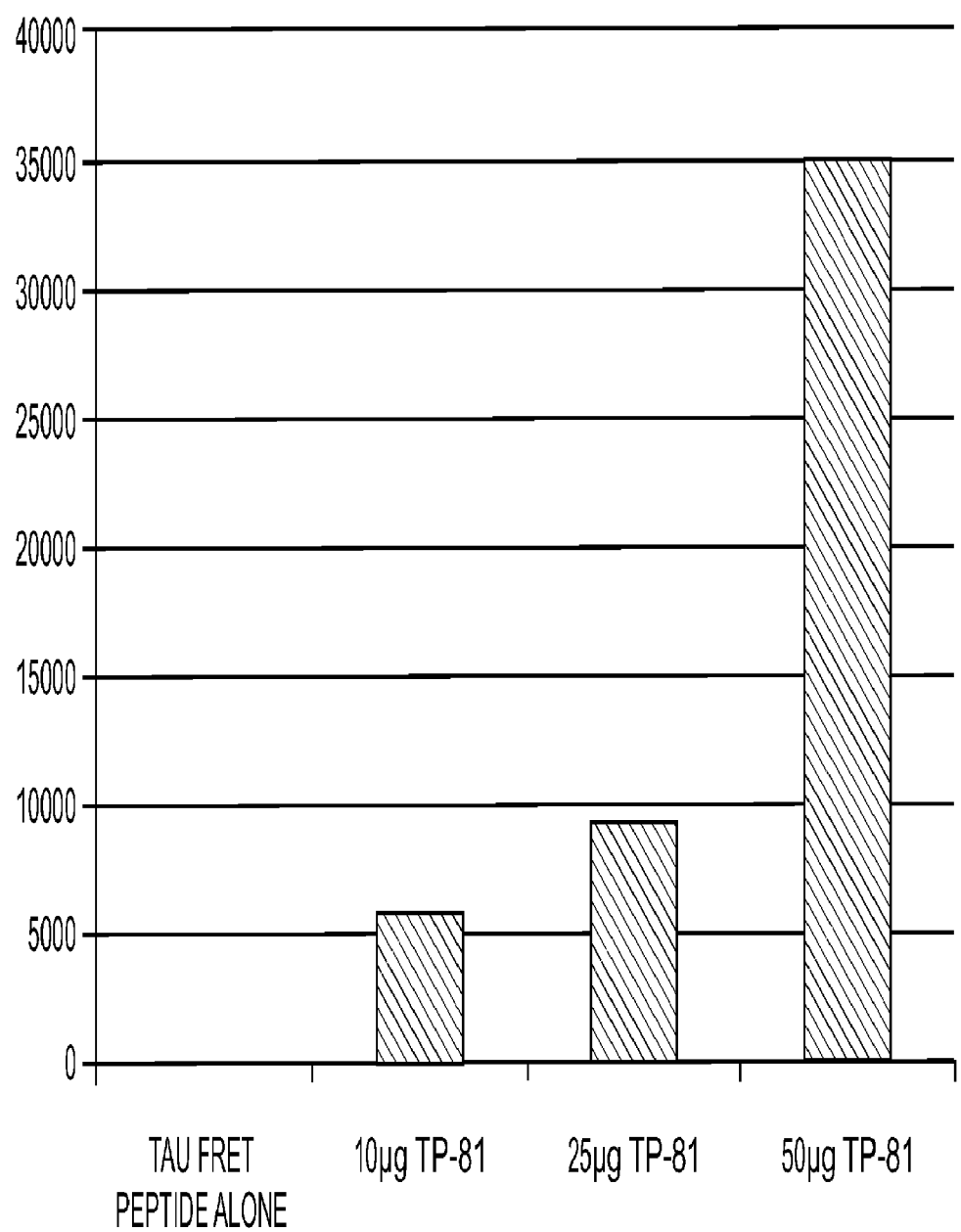

As in FIG. 7, cleavage of the peptide substrate for tau protease Tau 4R2N (amino acids 335-353) was used to monitor activity using reverse-phase HPLC. The lower trace shows the peptide incubated in reaction buffer in the absence of TP-99, and the middle trace shows the peptide incubated with TP-99. The large peak in the lower trace indicates intact peptide which is greatly diminished in the upper trace and replaced with two smaller peaks $F_1$ and $F_2$ that represent fragments generated by TP-99. Addition of 100 µM zinc chloride increased the activity of Tau 4R2n 241-340 (TP-99) (top trace). The asterisk indicates an artifact peak that is derived from the incubation tube. Ten microgram of Tau peptide 335-353 (OP-001) was incubated without TP-99, with 25 µL, TP-99 oligomer ladder, or with additional 100 µM zinc chloride, 44 hr at 37° C. in 30 µL buffer (25 mM Tris-HCl pH 7.4). Samples were analyzed by reverse phase HPLC (SystemGold® 32Karat™ LC-CE System, Beckman Coulter, Inc., (Indianapolis, Ind.)) using a linear gradient of acetonitrile in 0.1% TFA 0-60% acetonitrile on an analytical $C_{18}$ column (12.5 cm×2.1 mm, 5 µm, (Supelco);

FIG. 9A shows that tau 4R2N trimer protease cuts α-endorphin peptide. Human α-endorphin peptide [TyrGlyGlyPheMetThrSerGluLysSerGlnThrProLeuValThr (SEQ ID NO:13) (Abbiotech, LLC, San Diego, Calif., USA)] was incubated at 37° C. for 20 hrs with or without 1.2 pg tau 4R2N trimer protease, and analyzed by reverse phase HPLC (SystemGold® 32Karat™ LC-CE System, Beckman Coulter, Inc., Indianapolis, Ind., USA) using a linear gradient of acetonitrile in 0.1% TFA, 0-60% acetonitrile on an analytical $C_{18}$ column (12.5 cm×2.1 mm, 5 µm (Supelco). The peptide was hypothesized to be cut by tau protease because it contains Lys-Ser in its sequence which is found at autocatalytic cleavage sites in tau. Two fragment peaks were produced as predicted by tau 4R2N trimer protease. These results showed that tau 4R2N trimer protease could cleave neurotransmitter or neuroactive peptides. The asterisk indicates an artifactual peak unrelated to the peptide;

FIG. 9B shows that tau 4R2N trimer protease cuts APP 667-676 peptide. Human APP 667-676 peptide [Ser-Glu-Val-Lys-Met-Asp-Ala-Glu-Phe-Arg (SEQ ID NO:14) (Anaspec, Fremont, Calif., USA)] was incubated 20 hr at 37° C. with or without 1.2 pg tau 4R2N trimer protease and analyzed by reverse phase HPLC (SystemGold® 32Karat™ LC-CE System, Beckman Coulter, Inc.) using a linear gradient of 0 to 60% acetonitrile in 0.1% TFA on an analytical $C_{18}$ column (12.5 cm×2.1 mm, 5 pm, Supelco). Two major fragment peaks were produced by tau protease from the APP 667-676 peptide suggesting that tau protease cut after the Lys residue in the sequence. The asterisk indicates an artifactual peak unrelated to the peptide. Tau 4R2N trimer protease cut APP at the penultimate amino acid adjacent to the β-secretase (BACE) cut site thereby generating Aβ(1-42). Tau protease activity has been observed extracellularly in the CSF. Generation of Aβ(1-42) can stimulate inflammation within a neuron leading to BACE up-regulation. Furthermore Aβ(1-42) has been observed in plaques and can be converted to Aβ(1-42) by BACE cleavage of the N-terminal methionine. The implications are that tau protease may be the initial activation step for the amyloid cascade;

FIG. 10 demonstrates that tau 4R2N trimer protease cuts tau (4R1N) monomer and tau dimer. Tau oligomer formation leads to gain of toxic function and loss of function of tau monomer degraded by tau 4R2N trimer activity. Lane 1: Tau 4R2N monomer (0.1 µg); Lane 2: 1× Sample Buffer without reductant; Lane 3: 4R2N Trimer, no 4R1N; Lane 4:Tau 4R1N, no tau 4R2N trimer; Lane 5: Tau 4R2N trimer:tau 4R1N, 1:10; Lane 6: Tau 4R2N trimer:tau 4R1N trimer, 1:100; Lane 7: Tau 4R2N trimer:tau 4R1N 1:10. Tau trimer protease (4R2N) was incubated at 37° C. overnight with and without Tau 4R1N oligomer mixture followed by separation by SDS-PAGE on a 4-20% gradient Criterion™ gel (Bio-Rad, Hercules, Calif.) in the presence of reductant (final β-mercaptoethanol 5%), and specific cutting was observed for both monomer and dimer. The arrows indicate fragments of tau 4R1N that are generated from tau 4R2N trimer protease activity. For the upper arrow, the fragments have the same apparent MW between the two isoforms, the lower arrow fragments differ with the fragment from tau 4R1N migrating faster than the fragment from tau 4R2N;

FIG. 11 shows serine protease inhibitor panel for tau 4R2N protease. Tau 4R2N trimer was incubated overnight at 37° C. with and without serine-specific protease inhibitors (Sigma Aldrich, St. Louis, Mo.). The incubation volumes were 3.45 microliter at a final concentration of 0.145 mg/mL tau 4R2N trimer. Lane 1—Protein standards; Lane 2—Tau 4R2N monomer without incubation; Lane 3—Tau 4R2N trimer without incubation (no protease inhibitor); Lane 4—Tau 4R2N trimer with incubation (no protease inhibitor); Lane 5—Tau 4R2N trimer incubated with 1 mM 4-(2-Aminoethyl) benzenesulfonyl fluoride hydrochloride (AEBSF); Lane 6—Tau 4R2N trimer incubated with 800 nM aprotinin; Lane 7—Tau 4R2N trimer incubated with 100 µM antipain; Lane 8—Tau 4R2N trimer incubated with 100 µM chymostatin; Lane 9—Tau 4R2N trimer incubated with 100 micromolar elastatinal; Lane 10—Tau 4R2N trimer incubated with 38.1 mM s-amino caproic acid (EACA); Lane 11—Tau 4R2N trimer incubated with 500 µM gabexate mesylate; Lane 12—Tau 4R2N trimer incubated with 100 µM leupeptin; Lane 13—Tau 4R2N trimer incubated with 500 µM nafamostat mesylate; Lane 14—Tau 4R2N trimer incubated with 100 tosyllysine chloromethyl ketone hydrochloride (TLCK-HCL); Lane 15—Tau 4R2N trimer incubated with 100 µM N-p-tosyl-L-phenylalanine chloromethyl ketone (TPCK); Lane 16—Tau 4R2N trimer incubated with 4 µM trypsin inhibitor; Lane 17—Tau 4R2N trimer incubated with 1 mM phenylmethanesulfonyl fluoride (PMSF); Lane 18—Tau 4R2N trimer incubated with 20% dimethyl sulfoxide (DMSO);

FIG. 12 shows tau 4R2N trimer incubated with a serine protease inhibitor panel. Tau 4R2N trimer was incubated overnight at 37° C. with and without serine-specific protease inhibitors at low and high concentrations. Lane 1: Tau 4R2N trimer without incubation (no protease inhibitor); Lane 2: 4R2N trimer incubated without protease inhibitor; Lane 3: Tau 4R2N trimer incubated with 1 µM trypsin inhibitor; Lane 4: Tau 4R2N trimer incubated with 4 µM trypsin inhibitor; Lane 5: Tau 4R2N trimer incubated with 0.1 mM AEBSF; Lane 6: Tau 4R2N trimer incubated with 1 mM AEBSF; Lane 7: Tau 4R2N trimer incubated with 1 mg/mL EACA; Lane 8: Tau 4R2N trimer incubated with 5 mg/mL EACA; Lane 9: Tau 4R2N trimer incubated with 1 µM Antipain; Lane 10: Tau 4R2N trimer incubated with 100 µM antipain; Lane 11: Tau 4R2N trimer incubated with 10 nM aprotinin; Lane 12: Tau 4R2N trimer incubated with 800 nM aprotinin; Lane 13: Tau 4R2N trimer incubated with 10 µM chymostatin; Lane 14: Tau 4R2N trimer incubated with 100 µM chymostatin; Lane 15: Tau 4R2N trimer incubated with 10 µM leupeptin; Lane 16: Tau 4R2N trimer incubated with 100 µM leupeptin. Of the inhibitors tested, chymostatin showed the greatest inhibitory effect of the serine protease inhibitors tested. Moreover, tau protease activity was inhibited by serine protease inhibitor panels in a dose dependent manner. The activity was consistent with serine protease family based on specificity of protease inhibitors and on mass spec data showing cleavage after basic amino acid lysine (K) characteristic of some serine proteases such as trypsin;

FIG. 13 shows FP-TAMRA labeling of oligomerized tau 4R2N that was blocked by a serine hydrolase inhibitor AEBSF. This method independently indicated that tau is a serine hydrolase. Tau 4R2N oligomer ladder was labeled with fluorophosphonate (FP) linked to a fluorescent TAMRA tag (ThermoFisher Scientific), a probe that is specific for active site serines in serine proteases. FP probes specifically label the serines of enzymatically-active serine hydrolases. The serine protease-specific inhibitor, AEBSF, was used in a dose-response study to determine whether tau was being specifically labeled with FP. The 4-20% polyacrylamide gradient gel of the labeled samples was imaged with a Typhoon 9400™ scanner (GE Healthcare Biosciences, Pittsburgh, Pa.), and subsequently stained with a Coomassie product GelCodeBlue Safe (ThermoFisher Scientific) to visualize total protein and demonstrate equal loading of protein in the lanes. The results showed that tau labeling was inhibited in a dose-dependent manner as AEBSF concentration was increased. Samples were run without reductant or with reductant as indicated. For labeling, 10 µg of tau 4R2N was labeled with 5 micromolar FP-TAMRA in 10 µL buffer (25 mM Tris-HCl pH 7.4, 150 mM NaCl, 0.5 mM EDTA, 0.1% NP-40, 5% glycerol) for 4 hrs at room temperature in the dark. Samples were pretreated with 0, 0.1, 1.0, or 10.0 mM AEBSF for 1 hr at room temperature to block the active-site serine before the addition of the FP-TAMRA probe. Samples were divided in half and run with sample buffer with or without reductant as indicated;

FIG. 14A shows AEBSF inhibited tau 4R2n trimer protease activity. The peptide assay for tau 4R2N trimer activity described in FIG. 5 was used to screen a series of serine protease inhibitors. 1 mM AEBSF was incubated with tau 4R2N trimer for 1 hr at room temperature before addition of the peptide substrate. This result indicated that tau 4R2N trimer is in the class of serine proteases and that molecules may be screened using this assay to identify inhibitors of tau protease. The asterisk indicates an artifactual peak unrelated to the peptide;

FIG. 14B shows antipain inhibited tau 4R2N trimer activity. 100 pM antipain, a reversible inhibitor of serine/cysteine proteases and some trypsin-like serine proteases, strongly inhibited cleavage of the peptide. The peptide assay for tau protease activity described in FIG. 5 was used to screen a series of serine protease inhibitors. 100 pM antipain was incubated with tau 4R2N trimer for one hr at room temperature before addition of the peptide substrate. This result indicates that tau protease is in the class of serine proteases and that molecules may be screened using this assay to identify inhibitors of tau protease. The asterisk indicates an artifactual peak unrelated to the peptide;

FIG. 14C shows that aprotinin strongly inhibited tau protease activity. The peptide assay for tau protease activity described in FIG. 5 was used to screen a series of serine protease inhibitors. 800 nM aprotinin was incubated with tau protease for 1 hr at room temperature before addition of the peptide substrate. This result indicates that tau protease is in the class of serine proteases and that molecules may be screened using this assay to identify inhibitors of tau protease. The asterisk indicates an artifactual peak unrelated to the peptide;

FIG. 14D shows that chymostatin inhibited tau protease activity. Chymostatin is a mixture of several components (Cymostatin A, Chymostatin B, Chyomstain C), and is a strong inhibitor of many proteases including chymotrypsin, chymotrypsin-like serine proteinases, chymases. 99 pM chymostatin strongly inhibited cleavage of the peptide. The peptide assay for tau protease activity described in FIG. 5 was used to screen a series of serine protease inhibitors. 99 pM chymostatin was incubated with tau protease for 1 hr at room temperature before addition of the peptide substrate. This result indicated that tau protease was in the class of serine proteases and that molecules may be screened using this assay to identify inhibitors of tau protease. The asterisk indicates an artifactual peak unrelated to the peptide;

FIG. 14E shows that PMSF inhibited tau 4R2N trimer activity. 1 mM PMSF an irreversible inhibitor of serine proteases, strongly inhibited cleavage of the peptide. The peptide assay for tau protease activity described in FIG. 5 was used to screen a series of serine protease inhibitors. 1 µM PMSF was incubated with tau 4R2N trimer for one hr at room temperature before addition of the peptide substrate. This result indicates that tau protease is in the class of serine proteases and that molecules may be screened using this assay to identify inhibitors of tau protease. The asterisk indicates an artifactual peak unrelated to the peptide. Also inhibits papain (reversible by DTT treatment) and acetylcholinesterase, but does not inhibit metallo-, aspartic- and most cysteine proteases;

FIG. 14F shows that gabexate mesylate, a serine protease-specific inhibitor, did not significantly inhibit cleavage of the peptide at the tested concentration. The peptide assay for tau protease activity described in FIG. 5 was used to screen a series of serine protease inhibitors. 150 pM of gabexate mesylate was incubated with tau protease for 1 hr at room temperature before addition of the peptide substrate. This result indicates that tau protease shows selectivity for serine protease-specific inhibitors. The asterisk indicates an artifactual peak unrelated to the peptide. Gabexate mesylate is a synthetic serine protease inhibitor used therapeutically in treatment of pancreatitis;

FIG. 15 illustrates fragments of tau FRET peptide cut by tau protease. Shown is a test of cutting peptide OP-002 designed for the tau protease FRET assay using tau 4R2N trimer protease and reverse phase HPLC analysis. Peptide OP-002 for FRET analysis of tau protease activity has sequence: MCA-GGQVEVKSE{Lys(DNP)} (SEQ ID NO:15) in which MCA is the fluorophore methoxycoumarin and DNP is the quench dinitrophenol. The addition of a Lys residue at the C-terminus of the peptide was necessary to conjugate DNP to the peptide. Peptide OP-002 was custom synthesized by Genscript (Piscataway, N.J., USA). 5 µg of peptide OP-002 was incubated with 0, 120 ng, 600 ng or 1200 ng tau 4R2N trimer in 20 microliter of buffer (25 mM Tris-HCl pH 7.4) and incubated 20 hr at 37° C. 10 µL of H₂O was added prior to HPLC to provide a sufficient volume for analysis. Analysis was performed by reverse phase HPLC (SystemGold® 32Karat™ LC-CE System, Beckman Coulter, Inc., (Indianapolis, Ind., USA)) using a linear gradient of acetonitrile in 0.1% TFA 0-60% acetonitrile on an analytical $C_{18}$ column (12.5 cm×2.1 mm, 5 µm, (Supelco);

FIG. 16 shows fluorescence of tau FRET peptide cut by tau protease. 5 µg of peptide OP-002 was incubated with 0, 120 ng, 600 ng or 1200 ng tau 4R2N trimer in 20 µL of buffer (25 mM Tris-HCl pH 7.4) and incubated 23 hrs at 37° C. 10 µL of each sample was transferred to wells containing 40 µL 25 mM Tris-HCl pH 7.4 in a black 96-well plate and mixed so that the sample volume was able to cover the well bottom. An EnVision® plate reader (Perkin Elmer, Waltham, Mass., USA) was used to measure the fluorescence in the wells;

FIG. 17 shows tau protease cut sites in the amyloid precursor protein (APP);

FIG. 18 shows a disease model for the tau protease mode of action in Alzheimer's disease leading to activation of Aβ(1-42) production. Cuts at additional sites in APP including the intracellular domain may interfere with normal APP and APP fragment functions;

FIG. 19 shows the nucleic acid sequence (SEQ ID NO:7) of a construct that encodes the 210 amino acid truncated tau protein, Tau 4R2N 131-340 (TP-210), (SEQ ID NO:1);

FIG. 20 shows the nucleic acid sequence (SEQ ID NO:9) of a construct that encodes the 99 amino acid truncated tau protein, Tau 4R2N 241-240 (TP-99), (SEQ ID NO:3);

FIG. 21 shows a flow chart for a large-scale purification of truncated tau proteins in accordance with one aspect of the present invention. Tau protein was expressed in *E. coli* BL21 (DE3) Gold (Agilent Technologies, La Jolla, Calif., USA). A 500 mL culture was grown at 37° C. with shaking at 250 rpm until the optical density at a wavelength of 600 nm reached 0.6 OD. Protein expression was enabled with the addition of isopropyl β-D-1-thiogalactopyranoside (IPTG; ThermoFisher Scientific) at a final concentration of 1 mM for 3 hrs at 37° C. with shaking at 250 rpm. The cells were harvested by centrifugation and frozen until future use. The cell pellet was resuspended in cell lysis buffer pH 7.0 comprising CelLyticB (Sigma, St. Louis, Mo.), 0.2 mg/mL lysozyme (Sigma, St Louis, Mo.), benzonase (Sigma) at 1750 Units total and protease inhibitors (Sigma) 100 µM chymostatin, 4 µM soybean trypsin inhibitor, and aprotinin at 0.8 µM. The cells are lysed at 4° C. for 30-60 min followed by centrifugation at 15,317×g to clear the lysate. The lysate was incubated with pre-equilibrated cation exchange resin SP Sepharose (GE Healthcare) at 4° C. for 1 hr with gentle end-over-end rotation. The resin was centrifuged at 4° C. at low speed, washed with a low salt buffer three times and the bound protein was eluted with 2× Laemmli sample buffer (Sigma). The preparative electrophoresis system (BioRad, Hercules, Calif.) was run at approximately 220V and fractions are collected at a flow rate of 1 mL/min using a peristaltic pump (BioRad). Fractions were analyzed by SDS-PAGE under reducing conditions using a 4-20% gradient Tris-HCl gel (BioRad). Protein fractions were pooled and buffer exchanged into 50 mM Tris-HCl pH 7.4 using an Amicon ultrafiltration device (Merck Millipore) with a molecular weight cut-off of 30,000 Da;

FIG. 22 shows exemplary peptide sequences used for HPLC studies showing tau OP-001 (aa335-353) (SEQ ID NO:16), aa 667-676 of human APP (SEQ ID NO:14), and human α-endorphin peptide (SEQ ID NO:13) sequences with the cut site for each indicated by the arrow;

FIG. 23A and FIG. 23B show specific labeling of proteins with a probe for active serine hydrolases that were immunopurified with an antibody against tau protein from a specimen of Alzheimer's brain suggesting that tau protein has serine hydrolase activity. Serine hydrolases include a class of enzymes that include serine proteases. The serine hydrolase superfamily is one of the largest known enzyme families that share a catalytic mechanism that involves a serine nucleophile. Phenylmethanesulfonyl fluoride (PMSF) irreversibly binds to the active site serine of serine hydrolases to inactivate their enzymatic activity and prevents the probe from labeling them. The proteins in the bands that had reduced labeling after treatment with PMSF were specifically labeled by the probe for active serine hydrolases (indicated by arrows). Protein was extracted from an AD brain by Dounce homogenization in TPER buffer (ThermoFisher Scientific) with 1 mM EDTA, 1 µg/mL pepstatin A, 20 mM phosphoramidon, phosphatase inhibitor (ThermoFisher Scientific). The lysate was cleared by centrifugation at 10,000×g for 20 min. The supernatant was depleted for biotin using Streptavidin-agarose (ThermoFisher Scientific). A probe specific for active serine hydrolases, fluorophosphonate (FP) labeled with a fluorescent carboxytetramethylrhodamine (TAMRA) tag (ThermoFisher Scientific), was incubated with the lysate at a final concentration of 2 µM. As a control for non-specific labeling, a portion of the lysate was treated with phenylmethanesulfonyl fluoride (PMSF), an irreversible inhibitor of serine hydrolases, including tau protease, before using the FP-TAMRA probe. Biotinylated monoclonal antibody HT7 (ThermoFisher Scientific) was used to capture total tau from the lysate with streptavidin-agarose beads (ThermoFisher Scientific). Protein that was bound by the antibody and captured by the beads was resolved by SDS-PAGE with or without the disulfide reductant β-mercaptoethanol. Fluorescent images were captured with a Typhoon® scanner (GE Healthcare Biosciences). Lane 1: Lysate after tau immunodepletion, no PMSF treatment; Lane 2: Lysate after tau immunodepletion, with PMSF treatment with PMSF; Lane 3: Immunocaptured protein, no PMSF treatment; Lane 4: Immunocaptured protein, with PMSF treatment. Samples were run without (FIG. 23A) and with (FIG. 23B) reductant to determine whether there were disulfide-mediated tau oligomers being labeled. White bands are due to overexposure at the voltage used for image capture. High voltage was necessary to visualize the bands from the tau immunoprecipitation. These results show that AD brain contains tau with serine protease activity supporting its role in the disease process;

FIG. 24 shows the amino acid sequence of the human amyloid precursor protein (APP) (SEQ ID NO:17); and FIG. 25 shows Tau 4R2N 260-340 cuts tau FRET peptide. A FRET assay was conducted to determine if the Tau 4R2N 260-340 construct has protease activity using the tau FRET peptide described in FIG. 22 and FIG. 23. 2.5 µg of tau FRET peptide was incubated alone or with 10, 25 or 50 µg of oligomerized Tau 4R2N 260-340 in 30 µL of buffer (25 mM Tris-HCl pH 7.4) for 17 hrs at 37° C. To determine the background values for the wells of the 96-well plate 95 microliter of buffer was added to the wells of a black 96-well Microfluor I plate (ThermoFisher Scientific) and an EnVision plate reader was used to determine signal (as described in FIG. 23). 5 µL of each sample was mixed with the buffer in the wells and the signal was determined. The difference between the samples and background is shown in the bar graph.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Tau protease is activated through the formation of oligomeric tau species stabilized by disulfide linkages. Tau protease has been demonstrated to cut a number of proteins that are important for Alzheimer's disease including tau monomer and higher order aggregates, tubulin, APP, and also important neuropeptides such as alpha-endorphin.

The accumulation of tau protease in the brain is believed to be a primary cause for the progression of Alzheimer's disease. Since there is no effective drug for the treatment of Alzheimer's disease, there is an intense interest in studying the inhibition of Tau protease and for identifying inhibitors useful for therapeutic intervention in Alzheimer patients. Infusion of active tau oligomer preps into wild type mice show inhibition of memory formation and decreases in CREB phosphorylation and inhibition of histone4 acetylation, both molecular markers for memory formation. Additionally, infusion studies using mouse hippocampal slices shows a dose dependent impairment in long-term potentiation (LTP), an electrophysiological measure of memory formation. Furthermore, Tau has shown to be present in CSF and to increase with disease severity and may be responsible for the spread of its own pathology. Moreover, its ability to cleave APP may activate the amyloid cascade model resulting in both increased BACE production and diminished ability for diseased cells to enter apoptosis. Extracellular tau protease is thought to be pathological with no known function. Therefore, development of inhibitors for blocking this activity either extracellular in the CSF or intracellular may show significant clinical benefit for AD patients at all stages of disease without detrimental side effects and therefore without major toxicity.

Isoforms of Tau Protein

Tau structural isoforms can differ from each other in the number of tubulin-binding domains (three or four repeats located in the C-terminal half of the protein), and are referred to as 3R or 4R tau isoforms, respectively. They can also differ in the presence or absence of either one or two 29-amino-acid-long, highly acidic inserts at the N-terminal portion of the protein (the projection domain). Between the projection domain and the microtubule-binding domain lies a basic proline-rich region. Tau 4R2N undergoes autoproteolytic cleavage when it forms disulfide-mediated oligomers when incubated at 37° C. in buffer (25 mM Tris-HCl pH 7.4 after removal of SDS). Tau 4R1N showed similar properties. Self-interaction of inactive monomer to form an active protease is exemplified by the caspases. Dimerization is central to procaspase activation because the active sites are comprised of loops from both monomers. The activity of trimer was greater than dimer in both protease and neurotoxicity assays. During incubation, tau monomer and tau dimer form higher order aggregates as observed as distinct upper bands on gels, whereas trimer does not form additional higher order aggregates. Lack of reactivity to form higher order oligomers suggests that the structure does not contain any free thiols. A model based on formation of tau trimer disulfides identifies potential proposed catalytic triad amino acids.

Purified tau trimer demonstrated the most complete autoproteolytic activity rendering three major fragments during prolonged incubation. The monomer preparation formed oligomers during purification and at the same time formed fragments. The dimer and trimer preparations began autoproteolytic fragmentation during buffer exchange and concentration at the end of the purification process. Formation of disulfide mediated tau oligomers activated tau protease activity. Zymogram analysis demonstrated that the protease activity correlated with tau species (higher order aggregates and tau fragments in addition to activity observed for monomer band which forms disulfide mediated aggregates during incubation) ruling out the possibility that it is caused by contamination. The spatial correlation between tau bands and proteolytic activity indicated that tau itself has activity and not a contaminating protease.

Tau Protease Cleaves Tubulin

Tau protease, in addition to its autocatalytic cleavage reaction cuts tubulin. Normal activity of monomer tau is to interact with tubulin to form and stabilize microtubules in axons. In disease, tau oligomers form with activity that degrades tubulin suggests a direct pathological mechanism for disruption of microtubules and neuronal function. When tau trimer protease was incubated overnight with or without protease inhibitor (PI) cocktail (containing serine protease, amino-peptidase, cysteine protease and aspatic protease inhibitors) the PI cocktail inhibited additional fragmentation in a manner that was consistent with an enzymatic function. Current data suggest that tau trimer has the highest protease activity whereas tau dimer has intermediate activity and tau monomer has low protease activity. Data also suggest that there are no free thiols in active trimer protease, and tau protease is not a cysteine protease.

Western blot analysis using antibodies specific for the C-terminal and N-terminal portions of tau pinpointed a 6.2 KDa fragment (Fragment 1) to the carboxy-terminus of tau, and suggests that a 1.7-KDa fragment (Fragment 3) contains the microtubule binding domain and a 19.5-KDa fragment (Fragment 2) contains the N-terminus of tau. In addition to binding microtubules, tau also interacts with components of the plasma membrane. The N-terminal projection domain of tau associates with the plasma membrane. In oligodendrocytes, tau regulates process formation (membrane extensions) through interactions with fyn. Phosphorylation within the N-terminal half of tau at serine/threonine residues regulates its association with the neuronal membrane. Fyn, a tyrosine kinase, interacts with tau through its proline-rich region and phosphorylates tau at the N-terminus causing it to translocate to the plasma membrane. Phosphorylation at serine/threonine residues inhibits the tau-Fyn interaction and translocation to the membrane. This dendritic role of tau confers Aβ toxicity at the postsynapse with direct implications for pathogenesis and treatment of AD. Sequence analysis suggests that tau protease can cut APP adjacent to the (3-secretase site resulting in Aβ. This may be important in Alzheimer's disease as it ties directly together both Aβ and tau pathologies. Inhibition of tau protease would therefore be an affective therapeutic intervention that would ameliorate both tau and Aβ pathologies.

Truncated Tau Polypeptides Retain Protease Activity

Exemplary truncated tau peptides (designated herein as TP-210, TP-99, TP-118, TP-83, and TP-81, respectively) have been identified and prepared that retain tau protease enzymatic activity. The amino acid positions shown correspond to the numbering of that of the wild-type, 4R2N form:

TP-210: (4R2N131-340)
```
  1 ATGAGCAAAGACGGTACTGGTAGCGACGACAAAAAAGCAAAAGGT
    M   S   K   D   G   T   G   S   D   D   K   K   A   K   G

46 GCTGATGGTAAAACCAAGATCGCAACCCCGCGTGGTGCAGCACCG
    A   D   G   K   T   K   I   A   T   P   R   G   A   A   P

91 CCGGGCCAGAAAGGCCAGGCCAACGCCACCCGTATTCCGGCAAAA
    P   G   Q   K   G   Q   A   N   A   T   R   I   P   A   K

136 ACCCCGCCGGCTCCGAAAACCCCGCCGAGCTCTGGTGAACCGCCG
    T   P   P   A   P   K   T   P   P   S   S   G   E   P   P

181 AAATCTGGTGACCGTAGCGGCTACAGCAGCCCGGGCTCTCCGGGC
    K   S   G   D   R   S   G   Y   S   S   P   G   S   P   G

226 ACTCCGGGCAGCCGTTCTCGTACCCCGTCTCTTCCGACCCCGCCG
    T   P   G   S   R   S   R   T   P   S   L   P   T   P   P

271 ACCCGTGAACCGAAAAAGGTTGCAGTGGTCCGTACTCCGCCGAAA
    T   R   E   P   K   K   V   A   V   V   R   T   P   P   K

316 TCTCCGTCTTCTGCAAAGAGCCGTCTGCAGACCGCACCGGTTCCG
    S   P   S   S   A   K   S   R   L   Q   T   A   P   V   P

361 ATGCCGGACCTGAAAAATGTTAAATCTAAGATCGGCTCTACTGAA
    M   P   D   L   K   N   V   K   S   K   I   G   S   T   E

406 AACCTGAAACACCAGCCGGGIGGCGGTAAAGTTCAGATCATTAAT
    N   L   K   H   Q   P   G   G   G   K   V   Q   I   I   N

451 AAGAAACTGGACCTTAGCAACGTTCAGTCTAAATGTGGCTCTAAG
    K   K   L   D   L   S   N   V   Q   S   K   C   G   S   K

496 GACAATATCAAACACGTTCCGGGTGGCGGCTCTGTTCAAATCGTT
    D   N   I   K   H   V   P   G   G   G   S   V   Q   I   V

541 TACAAACCGGTTGACCTGAGCAAAGTTACCTCTAAGTGTGGCTCT
    Y   K   P   V   D   L   S   K   V   T   S   K   C   G   S

586 TTAGGCAACATCCATCATAAACCGGGTGGTGGCCAGGTTGAAGTA
    L   G   N   I   H   H   K   P   G   G   G   Q   V   E   V

631 AAATAG (SEQ ID NO: 7)
    K   -  (SEQ ID NO: 1) (210 amino acids)
```

TP-118: (4R2N268-385)
```
ATGCACCAGCCGGGAGGCGGGAAGGTGCAGATAATTAATAAGAAGCTG
 M   H   Q   P   G   G   G   K   V   Q   I   I   N   K   K   L

GATCTTAGCAACGTCCAGTCCAAGTGTGGCTCAAAGGATAATATCAAACACGTCCCGGGA
 D   L   S   N   V   Q   S   K   C   G   S   K   D   N   I   K   H   V   P   G

GGCGGCAGTGTGCAAATAGTCTACAAACCAGTTGACCTGAGCAAGGTGACCTCCAAGTGT
 G   G   S   V   Q   I   V   Y   K   P   V   D   L   S   K   V   T   S   K   C

GGCTCATTAGGCAACATCCATCATAAACCAGGAGGTGGCCAGGTGGAAGTAAAATCTGAG
 G   S   L   G   N   I   H   H   K   P   G   G   Q   V   E   V   K   S   E

AAGCTTGACTTCAAGGACAGAGTCCAGTCGAAGATTGGGTCCCTGGACAATATCACCCAC
 K   L   D   F   K   D   R   V   Q   S   K   I   G   S   L   D   N   I   T   H

GTCCCTGGCGGAGGAAATAAAAAGATTGAAACCCACAAGCTGACCTTCCGCGAGAACGCC
 V   P   G   G   G   N   K   K   I   E   T   H   K   L   T   F   R   E   N   A

AAAGCCAAGTAG (SEQ ID NO: 8)
 K   A   K   -  (SEQ ID NO: 2) (118 amino acids)
```

TP-99: (4R2N241-340)
```
  1 ATGCGTCTGCAGACCGCACCGGITCCGATGCCGGACCTGAAAAAT
    M   R   L   Q   T   A   P   V   P   M   P   D   L   K   N

46 GTTAAATCTAAGATCGGCTCTACTGAAAACCTGAAACACCAGCCG
    V   K   S   K   I   G   S   T   E   N   L   K   H   Q   P

91 GGIGGCGGTAAAGTTCAGATCATTAATAAGAAACTGGACCTTAGC
    G   G   G   K   V   Q   I   I   N   K   K   L   D   L   S

136 AACGTTCAGTCTAAATGGGCTCTAAGGACAATATCAAACACGTT
    N   V   Q   S   K   C   G   S   K   D   N   I   K   H   V
```

```
                        -continued
181 CCGGGTGGCGGCTCTGTTCAAATCGTTTACAAACCGGTTGACCTG
       P  G  G  G  S  V  Q  I  V  Y  K  P  V  D  L 226 AGCAAAGTTACCTCTAAGTGTGGCTCTTTAGGCAACATCCATCAT
       S  K  V  T  S  K  C  G  S  L  G  N  I  H  H 271 AAACCGGGTGGTGGCCAGGTTGAAGTAAAATAG 303 (SEQ ID NO: 9)
       K  P  G  G  Q  V  E  V  K  -(SEQ ID NO: 3)(99 amino acids)

TP-83: (4R2N258-340)
                  (SEQ ID NO: 10)    ATGTCCAAGATCGGCTCC
(83 amino acids) (SEQ ID NO: 4)     M  S  K  I  G  S
ACTGAGAACCTGAAGCACCAGCCGGGAGGCGGGAAGGTGCAGATAATTAATAAGAAGCTG
 T  E  N  L  K  H  Q  P  G  G  G  K  V  Q  I  I  N  K  K  L GATCTTAGCAACGTCCAGTCCAAGTGTGGCTCAAAGGATAATATCAAACACGTCCCGGGA
 D  L  S  N  V  Q  S  K  C  G  S  K  D  N  I  K  H  V  P  G GGCGGCAGTGTGCAAATAGICTACAAACCAGTTGACCTGAGCAAGGTGACCTCCAAGTGT
 G  G  S  V  Q  I  V  Y  K  P  V  D  L  S  K  V  T  S  K  C GGCTCATTAGGCAACATCCATCATAAACCAGGAGGTGGCCAGGTGGAAGTAAAATAG
 G  S  L  G  N  I  H  H  K  P  G  G  Q  V  E  V  K  -

TP-81: (4R2N260-340)
                  (SEQ ID NO: 11)    ATGATCGGCTCC
(81 amino acids) (SEQ ID NO: 5)     M  I  G  S
ACTGAGAACCTGAAGCACCAGCCGGGAGGCGGGAAGGTGCAGATAATTAATAAGAAGCTG
 T  E  N  L  K  H  Q  P  G  G  G  K  V  Q  I  I  N  K  K  L GATCTTAGCAACGTCCAGTCCAAGTGTGGCTCAAAGGATAATATCAAACACGTCCCGGGA
 D  L  S  N  V  Q  S  K  C  G  S  K  D  N  I  K  H  V  P  G GGCGGCAGTGTGCAAATAGICTACAAACCAGTTGACCTGAGCAAGGTGACCTCCAAGTGT
 G  G  S  V  Q  I  V  Y  K  P  V  D  L  S  K  V  T  S  K  C GGCTCATTAGGCAACATCCATCATAAACCAGGAGGTGGCCAGGTGGAAGTAAAATAG
 G  S  L  G  N  I  H  H  K  P  G  G  Q  V  E  V  K  -
```

Tau Protease Polynucleotides and Expression

Important aspects of the present invention concern isolated DNA segments and recombinant vectors encoding one or more tau protease-active polypeptides, and the creation and use of recombinant host cells through the application of DNA technology, that express one or more tau protease-active polypeptides. DNA segments, recombinant vectors, recombinant host cells and expression methods that produce such polypeptides are also provided by the present invention. As used herein, the term "nucleic acid segment" refers to a polynucleotide that has been isolated free of total genomic nucleic acids of a particular species. Therefore, a DNA segment encoding a tau protease refers to a DNA segment that contains tau protease-coding sequences, yet is isolated away from, or purified free from, total mammalian or human genomic DNA. Included within the term "DNA segment," are DNA segments and smaller fragments of such segments, and also recombinant vectors, including, for example, plasmids, cosmids, phage, viruses, and the like.

Similarly, a DNA segment comprising an isolated or purified tau protease gene refers to a DNA segment including tau protease coding sequences and, in certain aspects, regulatory sequences, isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, complementary DNA (cDNA) sequences and smaller engineered gene segments that express, or may be adapted to express, tau proteases, polypeptides, domains, peptides, fusion proteins and mutants.

"Isolated substantially away from other coding sequences" means that the gene of interest, in this case a tau protease or gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors that encode substantially full-length tau proteases, or to segments and recombinant vectors that encode one or more truncated tau proteases, variants, mutants, fusions, or epitopes thereof that include a contiguous amino acid sequence of at least about 15 amino acids, and more preferably, of at least about, 20, 25, 30, 35, 40, 45, 50, 55, 60, 65, or 70 or more contiguous amino acids from any one of SEQ ID NO:1, SEQ ID NO:2, SEQ ID NO:3, SEQ ID NO:4, SEQ ID NO:5, SEQ ID NO:6, or a biologically functional equivalent thereof.

The tau protease-encoding nucleic acid segments of the invention generally encode a protein or polypeptide that includes a contiguous amino acid sequence of at least about 12 amino acids or so, or more preferably, of at least about 16 amino acids or so, and more preferably still, of at least about 20 contiguous amino acids from any one of SEQ ID NO:1, SEQ ID NO:2, SEQ ID NO:3, SEQ ID NO:4, SEQ ID NO:5, or SEQ ID NO:6, or a biologically functional equivalent thereof; or the genes and/or DNA segments encoding such sequence hybridize to such a coding sequence under stringent hybridization conditions.

The term "a sequence essentially as set forth in SEQ ID NO:XX" means that the sequence substantially corresponds to a portion of the sequence recited in SEQ ID NO:XX, and has relatively few amino acids that are not identical to, or a biologically functional equivalent of, the amino acid sequence as recited in SEQ ID NO:XX. The term "biologically functional equivalent" is well understood in the art and is further defined in detail herein. Accordingly, sequences that have from about 85% to about 90%; or more preferably, between about 91% and about 95%; or even more preferably, from about 96% to about 99%; of amino acids that are identical or functionally equivalent to the amino acids of SEQ ID NO:1, SEQ ID NO:2, SEQ ID NO:3, SEQ ID NO:4, SEQ ID NO:5, or SEQ ID NO:6 will be sequences that are "essentially as set forth in SEQ ID NO:1, SEQ ID NO:2, SEQ ID NO:3, SEQ ID NO:4, SEQ ID NO:5, or SEQ ID NO:6," provided the biological activity (i.e., protease activity) of the protein is maintained.

The term "functionally equivalent codon" is used herein to refer to codons that encode the same amino acid, such as the six codons for arginine or serine, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have from about 75% to about 79%; or more preferably, from about 80% to about 89%; or even more preferably, from about 90% to about 99%; of nucleotides that are identical to one or more of the nucleotide sequences disclosed herein.

Sequences that are essentially the same as those set forth herein may also be functionally defined as sequences that are capable of hybridizing to a nucleic acid segment containing the complement of such a sequence under relatively stringent conditions. Suitable relatively stringent hybridization conditions will be well known to those of skill in the art.

Suitable standard hybridization conditions for the present invention include, for example, hybridization in 50% formamide, 5×Denhardts' solution, 5×SSC, 25 mM sodium phosphate, 0.1% SDS and 100 µg/mL of denatured salmon sperm DNA at 42° C. for 16 hr followed by 1 hr of sequential washes with 0.1×SSC, 0.1% SDS solution at 60° C. to remove the desired amount of background signal. Lower stringency hybridization conditions for the present invention include, for example, hybridization in 35% formamide, 5×Denhardts' solution, 5×SSC, 25 mM sodium phosphate, 0.1% SDS and 100 µg/mL denatured salmon sperm DNA or *E. coli* DNA at 42° C. for 16 hr followed by sequential washes with 0.8×SSC, 0.1% SDS at 55° C. Those of ordinary skill in the molecular biology arts will recognize that conditions can be readily adjusted to obtain the desired level of stringency.

Naturally, the present invention also encompasses nucleic acid segments that are complementary, or essentially complementary, to one or more of the sequences set forth herein. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to one or more of the nucleic acid segments disclosed herein under relatively stringent conditions such as those described immediately above.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

The various oligonucleotide detection probes and amplification primers designed around the disclosed tau protease-encoding nucleic acid sequences of the present invention may be of any suitable length. By assigning numeric values to a sequence, for example, the first residue is 1, the second residue is 2, etc., an algorithm defining all primers can be proposed:

n to n+y where n is an integer from 1 to the last number of the sequence and y is the length of the primer minus one, where n+y does not exceed the last number of the sequence. Thus, for a 125-mer, the probes correspond to bases 1 to 125, 2 to 126, 3 to 127 . . . and so on. For a 315-mer, the probes correspond to bases 1 to 315, 2 to 316, 3 to 317 . . . and so on. For a 360-mer, the probes correspond to bases 1 to 360, 2 to 361, 3 to 362 . . . and so on.

It will also be understood that this invention is not limited to the particular nucleic acid and amino acid sequences disclosed herein. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins or peptides that have variant amino acids sequences.

The polynucleotide segments of the present invention may encode one or more biologically-functional equivalent tau proteases, or one or more tau protease-derived truncated proteins, or one or more tau protease-related peptides, epitopes, fragments, variants, and/or mutants thereof. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine the function of tau protein or one or more of its proteolytic substrates in vivo and/or in vivo.

One may also prepare fusion proteins and peptides, e.g., where the tau protease coding regions are aligned within the same expression unit with other proteins or peptides having desired functions, such as for purification or immunodetection purposes (e.g., proteins that may be purified by affinity chromatography and enzyme label coding regions, respectively).

Also encompassed by the invention are nucleic acid segments encoding relatively small peptides, such as, for example, peptides of from about 7 to about 50 amino acids in length, and more preferably, of from about 10 to about 30 amino acids in length; and also larger polypeptides up to and including proteins corresponding to one or more contiguous amino acid sequences as set forth in SEQ ID NO:1, SEQ ID NO:2, SEQ ID NO:3, SEQ ID NO:4, SEQ ID NO:5, or SEQ ID NO:6.

The polynucleotides and nucleic acid segments comprising them may also be employed for a variety of applications. For example, a particularly useful application concerns the recombinant production of tau proteases or peptides, variants, truncations, fusions, mutants, or epitopes thereof. Additionally, the tau protease-encoding nucleic acid segments of the present invention can also be used in the preparation of tau-specific nucleic acid detection probes or amplification primers, which can, for example, be used in the identification and cloning of tau protease genes or related genomic sequences, or in the study of gene expression, and the like.

Nucleic Acid Detection and Hybridization

In addition to their use in directing the expression of the tau protein or to peptide or polypeptide variants or derivatives thereof that possess a serine protease enzymatic activity, the nucleic acid sequences disclosed herein also have a variety of other uses. For example, they also have utility as probes or primers in nucleic acid hybridization embodiments for the identification of tau protein- or tau protease-encoding polynucleotides.

The use of a hybridization probe, e.g., of about 14-20, 25-30, 50, 75, 100, 120, 150, 200, 250, 300 or so nucleotides in length allows the formation of a duplex molecule that is both stable and selective. Molecules having complementary sequences over stretches greater than about 20 bases in length are generally preferred, in order to increase stability and selectivity of the hybrid, and thereby improve the quality and degree of particular hybrid molecules obtained. In using sequences from any region of those disclosed herein, one may generally prefer to design nucleic acid molecules having stretches of about 75 to about 300 nucleotides, or even longer where desired. By choosing from more unique regions, as already disclosed herein, those of ordinary skill in the art will appreciate that smaller oligonucleotides probes and primers may be designed and utilized, e.g., of about 14-20, about 25, about 30, or about 35 or so nucleotides in length in applications where such smaller sequences are preferable.

All such fragments may be readily prepared by methods known to those of ordinary skill in the art, including, for example, directly synthesizing the fragment by chemical methodologies or by introducing selected sequences into recombinant vectors for recombinant production. These chemical methodologies can include, for example, the polymerase chain reaction (PCR™) technology of U.S. Pat. Nos. 4,683,195, 4,683,202, 4,800,159, and 4,603,102 (each of which is specifically incorporated herein in its entirety by express reference thereto) or by introducing selected sequences into recombinant vectors for recombinant production.

Accordingly, the nucleotide sequences of the invention may be used for their ability to selectively form duplex molecules with complementary stretches of genes or RNAs or to provide primers for amplification of DNA or RNA from tissues. Depending on the application envisioned, one will desire to employ varying conditions of hybridization to achieve varying degrees of selectivity of probe towards target sequence. For certain applications, for example, substitution of nucleotides by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, low stringency hybridization conditions for the present invention provide hybridization in 35% formamide, 5×Denhardts' solution, 5×SSC, 25 mM sodium phosphate, 0.1% SDS and 100 µg/mL denatured salmon sperm DNA or E. coli DNA at 42° C. for 16 hr followed by sequential washes with 0.8×SSC, 0.1% SDS at 55° C. and allows for cross-species hybridization to homologous proteins to occur.

In other embodiments, more stringent hybridization may be achieved under conditions of, for example, 50% formamide, 5×Denhardts' solution, 5×SSC, 25 mM sodium phosphate, 0.1% SDS and 100 µg/mL of denatured salmon sperm DNA at 42° C. for 16 hr followed by 1-hr sequential washes with 0.1×SSC, 0.1% SDS solution at 60° C. to remove the desired amount of background signal.

In certain embodiments, it will be advantageous to employ nucleic acid sequences of the present invention in combination with an appropriate means, such as a label, for determining hybridization. A wide variety of appropriate indicator means are known to those of ordinary skill in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally-undesirable reagents. In the case of enzyme tags, colorimetric indicator substrates are known that can be employed to provide a detection means visible to the human eye or spectrophotometrically, to identify specific hybridization with complementary nucleic acid-containing samples.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface to remove non-specifically bound probe molecules, hybridization is detected, or even quantified, by means of the detectable label.

Amplification and PCR™

Nucleic acid used as a template for amplification is isolated from cells contained in the biological sample, according to standard methodologies that are known to those of ordinary skill in the molecular biology arts. Such nucleic acids may be contained with genomic DNAs, or in populations of polynucleotides obtained from fractionated or whole-cell nucleic acid isolation and/or extraction. Pairs of primers that selectively hybridize to nucleic acids corresponding to tau protein or a truncated tau-protease, or a tau protease variant or mutant thereof are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced. Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals. A number of template dependent processes are available to amplify the marker sequences present in a given template sample. One of the best known amplification methods is the PCR™ methods discussed above.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation. In one embodiment, visualization is achieved indirectly. Following separation of amplification products, a labeled, nucleic acid probe is brought into contact with the amplified marker sequence. The probe preferably is conjugated to a detectable label (e.g., a chromophore, a fluorescent moiety, or one or more magnetic, spin resonance, or radioactive labels). In another embodiment, the probe is conjugated to a binding partner, such as an antibody or biotin, and the other member of the binding pair carries a detectable moiety.

In another embodiment, detection may be accomplished using methodologies such as Southern hybridization analysis (i.e., "Southern blots") via hybridization to a detectable, labeled probe. The techniques involved in Southern hybridization are well known to those of ordinary skill in the art, and can be found in many standard books on molecular protocols. Briefly, amplification products are separated by gel electrophoresis. The gel is then contacted with a membrane, such as PVDF or nitrocellulose, permitting transfer of the nucleic acid and non-covalent binding. Subsequently, the membrane is incubated with a labeled probe (such as a chromophore-conjugated or radiolabeled probe) that is capable of hybridizing with a target amplification product. Detection is by exposure of the membrane to X-ray film, or standard detection instruments.

One example of the foregoing is described in U.S. Pat. No. 5,279,721, specifically incorporated herein in its entirety by express reference thereto, which discloses an apparatus and method for the automated electrophoresis and transfer of nucleic acids. The apparatus permits electrophoresis and blotting without external manipulation of the gel and is ideally suited to carrying out such methods in the practice of the present invention.

All the essential materials and reagents required for detecting tau proteases in a sample may be assembled together in convenient "kit" form. Such kits are widely used in diagnostic and research methodologies, and generally include one or more preselected amplification primers, and, optionally, or one or more preselected labeled detection probes, molecular weight standards, and/or one or more positive or negative control samples. Also included may be enzymes suitable for amplifying nucleic acids including various polymerases (reverse transcriptase Taq, etc.), mixtures of deoxynucleotides, and one or more buffers or other reagents necessary to prepare suitable reaction mixtures for the given amplification and/or detection protocol(s) being employed.

Such kits generally will comprise, in suitable packaging, distinct containers for each individual reagent or enzyme as well as distinct containers for each set of primers and/or probes.

In another embodiment, such kits will comprise hybridization probes specific for tau protease-encoding sequences. Such kits generally will comprise, in suitable containers, one or more individual reaction components, buffers, enzyme(s), deoxynucleotide mixtures, as well as each of the selected hybridization probe(s) and or detection reagent(s) necessary to perform the test. Such kits also further optionally include one or more sets of instructions for performing the particular type of reactions, as well as individualized protocols, standard curves, positive and negative control sample, and/or such like.

Truncated, Mutated, or Substituted Tau Proteases

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the techniques of site-specific mutagenesis are well known to those of ordinary skill in the molecular biological arts. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

Site-directed mutagenesis is often performed by first obtaining a single-stranded vector, or melting of two strands of a double-stranded vector that includes within its sequence a nucleic acid segment that encodes the desired tau protease, or the protease-active fragment, variant, epitope, or mutant thereof. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement. The preparation of sequence variants of tau protease-encoding nucleic acid sequences using site-directed mutagenesis is provided as a means of producing potentially useful species and is not meant to be limiting, as there are other ways in which sequence variants of genes may be obtained. For example, recombinant vectors encoding the desired tau-encoding polynucleotide may be treated with one or more mutagenic agents, such as hydroxylamine, to obtain sequence variants of the tau protease.

Recombinant Vectors, Host Cells and Expression

Recombinant vectors form important further aspects of the present invention. The term "expression vector" or "expression construct" means any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of an RNA into a gene product. In other embodiments, expression only includes transcription of the nucleic acid, for example, to Generate antisense constructs.

Particularly useful vectors are contemplated to be those vectors in which the coding portion of the DNA segment, whether encoding a full length protein or smaller polypeptide or peptide, is operably positioned under the transcriptional control of at least a first promoter that is capable of expressing the sequence in suitable host cells. The phrases "operatively positioned," "under control" or "operably linked," and "under transcriptional control" mean that the promoter is in the correct location and orientation in relation to the nucleic acid to control RNA polymerase initiation and drive expression of the nucleic acid segment by the linked promoter. The promoter may be in the form of the promoter that is naturally associated with a gene that encodes a tau protein or a tau protease, as may be obtained by isolating the 5' non-coding sequences located upstream of the coding segment or exon, for example, using recombinant cloning and/or PCR™ technology, in connection with the compositions disclosed herein.

In other embodiments, it is contemplated that certain advantages will be gained by positioning the coding nucleic acid segment under the control of one or more recombinant, or heterologous, promoter(s). As used herein, a recombinant or heterologous promoter is intended to refer to a promoter that is not normally associated with a gene that encodes tau protein or a tau protease in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally well-known to those of ordinary skill in the art of molecular biology. The promoters employed may be constitutive, or inducible, and can be used under the appropriate conditions to direct high level expression of the introduced nucleic acid segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between the promoter elements can be increased to ~50 bp apart, before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a selected human host cell.

In various other embodiments, the human cytomegalovirus (CMV) immediate early gene promoter, the Simian virus 40 (SV40) early promoter, and the Rous sarcoma virus long-terminal repeat can be used to obtain high-level expression of the selected transgene. The use of other viral or mammalian cellular or bacterial phage promoters which are well-known in the art to achieve expression of a transgene is contemplated as well, provided that the levels of expression are sufficient for a given purpose. A number of expression elements, enhancers, and/or promoters may be employed in the context of the present invention to regulate the expression of tau protein or to facilitate expression of one or more nucleic acid segments encoding a tau protease-active fragment or variant thereof. Such enhancers, promoters, and expression elements are well-known to those of ordinary skill in the art.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization. Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Turning to the expression of a tau protease or a tau protease-active fragment or variant thereof, once a suitable clone or clones have been obtained (whether they be cDNA based or genomic) one may proceed to prepare a suitable expression system. The engineering of DNA segment(s) for expression in a prokaryotic or eukaryotic system may be performed by techniques generally known to those of ordinary skill in the art, and the inventors contemplate that virtually any conventional expression system in the art may be employed in the expression of the proteins, peptides, polypeptides, enzymes and/or epitopic sequences of the present invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired. As used herein, the terms "engineered" and "recombinant" cells are intended to refer to a cell into which an exogenous nucleic acid segment or gene, such as a cDNA or gene encoding a tau protein, or a tau protease-active truncate, variant, or mutant thereof, has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant tau protease, whether mutant, truncated, or wild-type, in accordance with the present invention one would prepare an expression vector that comprises a tau protease-encoding nucleic acid under the control of one or more suitable promoters. To bring a coding sequence "under the control of" a promoter, one positions the 5' end of the transcription initiation site of the transcriptional reading frame generally from about 1 to about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E. coli* and *B. subtilis* transformed with recombinant bacteriophage DNA, plasmid DNA or cosmid DNA expression vectors.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, and the like.

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more tau protease-encoding polynucleotide sequences.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired tau protein or tau protease-encoding polynucleotide sequence, provided such control sequences are compatible with the selected host cell system(s) to be employed. A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the BgII site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing tau proteases in infected hosts.

Specific initiation signals may also be required for efficient translation of certain tau protease-encoding sequences. These signals include the ATG initiation codon and adjacent sequences. Exogenous translational control signals, including the ATG initiation codon, may additionally need to be provided. This is particularly true in the case of tau protease fragments that lack an initiating methionine codon (see, e.g., the construction of TP-81, TP-99, TP-210, etc. discussed in the examples which follow). One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly-A addition site is placed about 30 to 2000 nucleotides "downstream" of the termination site of the protein at a position prior to transcription termination.

For long-term, high-yield production of recombinant tau proteases, stable expression is preferred. For example, cell lines that stably express constructs encoding tau proteases may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus (HSV) tk, hypoxanthine-guanine phosphoribosyltransferase (hgprt) and adenine phosphoribosyltransferase genes (aprt), in tk−, hgprt− or aprt− cells, respectively. Also, antimetabolite resistance can be used as the basis of selection for dhfr, that confers resistance to methotrexate; gpt, that confers resistance to mycophenolic acid; neo, that confers resistance to the aminoglycoside G-418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth). Non-anchorage dependent or suspension cultures from continuous established cell lines are the most widely used means of large scale production of cells and cell products. However, suspension cultured cells have limitations, such as tumorigenic potential and lower protein production than adherent cells. Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by devices such as magnetically-coupled drives and the like. Indirect drives reduce the risk of microbial contamination through seals on stirrer shafts. Airlift reactors (initially described for microbial fermentation and later adapted for mammalian culture), rely on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is about 10:1. The airlift reactor scales up relatively easily, has good mass transfer of gases and generates relatively low shear forces.

It is contemplated that the tau proteases or proteins of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

Tau Proteins, Peptides, and Polypeptides

The present invention therefore provides purified, and in preferred embodiments, substantially purified tau proteases, as well as truncated fragments, mutants or variants thereof. The term "purified tau protease" as used herein, is intended to refer to a tau proteinaceous composition, isolatable from suitable recombinant host cells, wherein the tau protease is prepared at levels that could not be previously obtained prior to the identification and characterization of nucleic acid segments that encode one or more tau proteases. A purified tau protease therefore also refers to a tau protease free from the environment in which it naturally occurs.

Where the term "substantially purified" is used, this will refer to a composition in which the tau protease, subunit or peptide forms the major component of the composition, such as constituting about 50% of the proteins in the composition or more. In preferred embodiments, a substantially purified tau protease will constitute more than 60%, 70%, 80%, 90%, 95%, 99% or even more of the proteins present in the composition.

A polypeptide or protein that is "purified to homogeneity," as applied to the present invention, means that the polypeptide or protein has a level of purity where the polypeptide or protein is substantially free from other proteins and biological components. For example, a purified polypeptide or protein will often be sufficiently free of other protein components so that degradative sequencing may be performed successfully.

Various methods for quantifying the degree of purification of tau proteases are known to those of ordinary skill in the art in light of the present disclosure. To purify a tau protease, a natural or recombinant composition that comprises at least some tau proteases will be subjected to fractionation to remove various non-tau protease components from the composition. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Tau Protease-Specific Antibodies, Immunological Reagents, and Epitopic Core Sequences Peptides corresponding to one or more antigenic determinants, or "epitopic core regions," of tau proteins or tau protease variants, mutants, or fragments thereof can also be prepared. Such peptides should generally be at least 7 or 8 amino acid residues in length, will preferably be about 10, 15, 20, 25 or about 30 amino acid residues in length, and may contain up to about 35-50 residues or so. Synthetic peptides may be fabricated using automated peptide synthesis instrumentation, or alternatively, by one or more recombinant methodologies.

U.S. Pat. No. 4,554,101 (specifically incorporated herein in its entirety by express reference thereto, teaches the identification and preparation of epitopes from primary amino acid sequences on the basis of hydrophilicity. Using methods that are known to those of ordinary skill in the antibody arts, one is able to identify epitopes from within an amino acid sequence of one of the tau protease sequences disclosed herein.

Moreover, computer programs are currently available to assist with predicting antigenic portions and eptiopic core regions of proteins. Examples include those programs based upon the Jameson-Wolf analysis and various computer programs for protein tertiary structure prediction, which are known to those of ordinary skill in the protein biology arts.

In further embodiments, major antigenic determinants of a polypeptide may be identified by an empirical approach in which portions of the gene encoding the polypeptide are expressed in a recombinant host, and the resulting proteins tested for their ability to elicit an immune response. For example, PCR™ can be used to prepare a range of peptides lacking successively longer fragments of the C-terminus of the protein. The immunoactivity of each of these peptides is determined to identify those fragments or domains of the polypeptide that are immunodominant. Further studies, in which only a small number of amino acids are removed at each iteration, permits more precise determination of the location of the antigenic determinants of the polypeptide.

Once one or more such analyses are completed, polypeptides are prepared that contain at least the essential features of one or more antigenic determinants. The peptides are then employed in the generation of antisera against the polypeptide. Minigenes or gene fusions encoding these determinants can also be constructed and inserted into expression vectors by standard methods, for example, using PCR™ cloning methodology.

The use of such small peptides for vaccination typically requires conjugation of the peptide to an immunogenic carrier protein, such as hepatitis B surface antigen, keyhole limpet hemocyanin or bovine serum albumin. Methods for performing this conjugation are well known to those of ordinary skill in the art.

Preparation of Tau-Specific Antibodies

In certain embodiments, the present invention provides antibodies that bind with high specificity to tau protein and other antibodies that bind to one or more truncated or mutated variants of a tau protease as disclosed herein. Antibodies specific for the wild type tau proteins and peptides and those specific for any one of a number of particular tau variants or mutants may be prepared using conventional methods known in the art. As detailed above, in addition to antibodies generated against substantially full-length proteins, antibodies may also be generated in response to smaller constructs comprising one or more epitopic core regions, including wild type and mutant epitopes from tau or other serine proteases. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. Monoclonal antibodies (MAbs) are recognized to have certain advantages, e.g., reproducibility and large-scale production, and their use is generally preferred. The invention thus provides Mabs of the human, murine, monkey, rat, hamster, rabbit and even chicken origin. Due to the ease of preparation and ready availability of reagents, murine Mabs are often preferred.

However, "humanized" antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's tumor are likewise known to those of ordinary skill in the art, and such custom-tailored antibodies are also contemplated to be useful in the creation of tau epitope-specific antibodies and the like. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are well known to those of ordinary skill in the art. The methods for generating Mabs generally begin along the same lines as those for preparing polyclonal antibodies. Briefly, a polyclonal antibody is prepared by immunizing an animal with an immunogenic tau composition in accordance with the present invention and collecting antisera from that immunized animal.

A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies. As is well known to those of ordinary skill in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria; MPL; trehalose dimycolate (TDM); and cell wall skeleton (CWS) in a 2% squalene/Tween 80 emulsion. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant. In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/m$^2$) (Johnson/Mead, N.J.) and Cytokines such as 7-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, which is specifically incorporated herein in its entirety by express reference thereto. Typically, this technique involves immunizing a suitable animal with a selected immunogen composition, e.g., a purified or a partially-purified tau protease, or a protease-active tau peptide fragment, mutant, variant, or epitopic domain, be it a wild-type or one or more variants, truncations, or mutations thereof. The immunizing composition is administered in a manner effective to stimulate antibody producing cells. The methods for generating MAbs generally begin along the same lines as those for preparing polyclonal antibodies. Rodents such as mice and rats are preferred animals; however, the use of rabbit, sheep, or other cell types is also possible. The use of rats may provide certain advantages, but mice are often preferred, as they generally give a higher percentage of stable fusions. The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals. Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes. The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of ordinary skill in the art. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the medium may be supplemented with a compound such as hypoxanthine.

MAbs produced by either means may be further purified, if desired, using filtration, centrifugation and various chromatographic methods such as HPLC or affinity chromatography. Fragments of the Mabs of the invention can be obtained from the Mabs so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer. It is also contemplated that a molecular cloning approach may be used to generate monoclonal antibodies that specifically bind to one or more of the tau protease compositions disclosed herein. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies. Alternatively, monoclonal antibody fragments encompassed by the present invention can be synthesized using an automated peptide synthesizer, or by expression of full-length gene or of gene fragments in one or more host cells, including, without limitation, bacterial, yeast, or fungal host cells.

Antibody Conjugates

The present invention further provides anti-tau protein antibodies, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of ordinary skill in the art. Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected and further quantified if desired. Another such example is the formation of a conjugate comprising an antibody linked to a cytotoxic or anti-cellular agent, as may be termed "immunotoxins." In the context of the present invention, immunotoxins are generally less preferred. Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Again, antibody-directed imaging is less preferred for use with this invention.

Many appropriate imaging agents are known in the art, as are methods for their attachment to antibodies (see, e.g., U.S. Pat. Nos. 5,021,236 and 4,472,509, each of which is specifically incorporated herein in its entirety by express reference thereto). Certain attachment methods involve the use of a metal chelate complex employing, for example, an organic chelating agent such a DTPA attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III). In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$Iodine is often being preferred for use in certain embodiments, and technicium$^{99m}$ and indium$^{111}$ are also often preferred due to their low energy and suitability for long range detection.

Radioactively-labeled tau protease-specific Mabs of the present invention may be produced according to well-known methods in the art. For instance, Mabs can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with technetium-$^{99}$m by ligand exchange process, for example, by reducing pertechnate with stannous solution, chelating the reduced technetium onto a Sephadex column and applying the antibody to this column or by direct labeling techniques, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) and ethylene diaminetetracetic acid (EDTA). Fluorescent labels include rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of ordinary skill in the art in light and is described, for example, in U.S. Pat. Nos. 3,817,837; 3,850,752; 3,939,350; 3,996,345; 4,277,437; 4,275,149 and 4,366,241 (each of which is specifically incorporated herein in its entirety by express reference thereto).

Immunodetection Methods and Kits

Immunodetection methods may be employed to identify novel compounds, polynucleotides, polypeptides, proteins or peptides or epitopes thereof that bind to, react with, inhibit, or are cleaved by, tau protease, and/or to identify a new property of a known protein, allowing the definition of that protein as a tau-binding protein, or a tau-protease target protein. In any event, the identification of an additional viral protein that binds to tau protease will allow the identified protein to become the target of new anti-Aβ strategies. The first step of such approaches will, again, often be based upon a binding assay in which potential compounds are tested for their ability to inhibit the binding of, prevent autoproteolysis of, prevent the cleavage of, or inhibit the protease activity of tau protease or of the newly discovered protein(s) or compound(s) so identified.

Antibodies and labeled antibodies against the tau proteases, peptides, or epitopes of the present invention may even further be employed to detect tau proteins or tau protease substrates in samples, including recombinant host cells and clinical samples. Such antibodies may ultimately be employed in diagnostic embodiments to detect increased or decreased levels of tau protease or to detect mutant tau proteins, truncated proteases or tau-derived peptides in biological samples such as human tissues and/or fluid samples.

Accordingly, detection of tau protease alone is another important aspect of the invention. In general, simple tau protease immunobinding methods include obtaining a sample suspected of containing a tau protease, variant, peptide, or mutant thereof, and contacting the sample with a first anti-tau protease antibody or anti-mutant tau protease antibody in accordance with the present invention, under conditions effective to allow the formation of immunocomplexes, and then detecting the immunocomplexes so formed.

In the clinical diagnosis or monitoring of patients with diseases such as AD, the detection of a tau protease mutant or an alteration in the levels of tau protease, in comparison to the levels in a corresponding biological sample from a normal subject will be indicative of a patient with AD. However, as is known to those of skill in the art, such a clinical diagnosis would not necessarily be made on the basis of this method in isolation. Those of skill in the art are very familiar with differentiating between significant differences in types or amounts of biomarkers, which represent a positive identification, and low level or background changes of biomarkers. Indeed, background expression levels are often used to form a "cut-off" above which increased detection will be scored as significant or positive.

Biological Functional Equivalents

As will be understood by those of skill in the art, modification and changes may be made in the structure of one or more of the disclosed tau proteases, and one or more of the tau protease-derived polypeptides described herein that possess serine protease activity, and still obtain a molecule having like or otherwise desirable characteristics. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. It is thus contemplated by the inventor that various changes may be made in the sequence of tau proteins or tau protease-active oligomers or fragments thereof (or the underlying DNA sequences that encode such a protein) without appreciable loss of their biological utility or activity.

In terms of functional equivalents, it is also well understood by the ordinary-skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where small peptides are concerned, less amino acids may be changed. Of course, a plurality of distinct proteins/peptides with different substitutions may easily be made and used in accordance with the invention.

It is also well understood that where certain residues are shown to be particularly important to the biological or structural properties of a protein or peptide, e.g., residues in the active site of the tau protease, such residues may not generally be exchanged without affecting the enzymatic activity of the resulting mutant protein. This is the case in the present invention, where residues in the active site of the protease should not generally be changed where it is the intention to maintain proteolytic function.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biological functional equivalent protein or peptide thereby created is intended for use in immunological embodiments, as in the present case. U.S. Pat. No. 4,554,101, specifically incorporated herein in its entirety by express reference thereto, states that the greatest local average hydrophilicity of a protein, as governed by the hydrophilicity of its adjacent amino acids, correlates with its immunogenicity and antigenicity, i.e. with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred. While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Pharmaceutical Compositions

Aqueous compositions of the present invention comprise an effective amount of one or more of the disclosed proteases dissolved or dispersed in one or more pharmaceutically-acceptable carriers, diluents, buffers, or aqueous medium. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, and general safety and purity standards as required by the FDA Office of Biologics.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intralesional, or even intraperitoneal routes. The preparation of an aqueous composition that contains a tau protease as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions containing one or more of the compounds of the present invention (either as free base or as pharmacologically-acceptable salts thereof) may be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. A protease composition in accordance with the present invention can also be formulated in a neutral or salt form. Pharmaceutically acceptable salts include the acid addition salts (formed with the free amino groups of the protein), and those which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the compositions can be brought about by the use in the compositions of agents delaying absorption, for example, aluminum monostearate, gelatin, or such like.

Sterile injectable solutions are prepared by incorporating one or more of the disclosed compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Exemplary Definitions

In accordance with the present invention, polynucleotides, nucleic acid segments, nucleic acid sequences, and the like, include, but are not limited to, DNAs (including and not limited to genomic or extragenomic DNAs), genes, peptide nucleic acids (PNAs) RNAs (including, but not limited to, rRNAs, mRNAs and tRNAs), nucleosides, and suitable nucleic acid segments either obtained from natural sources, chemically synthesized, modified, or otherwise prepared or synthesized in whole or in part by the hand of man.

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

As used herein, the term "protease" or "proteolytic enzyme(s)" means a hydrolytic enzyme that acts to break down one or more polypeptide substrates. Exemplary proteases may be of mammalian, and particularly, of human origin.

As used herein, the term "homology" is an indicator of the degree of identical elements between biological sequences, for example, the percent of identical amino acids between two aligned protein sequences. Gaps can be introduced into one or both of a first and a second amino acid or nucleic acid sequence for optimal alignment and non-homologous sequences may be disregarded for comparison purposes. As used herein, the term "similarity" is an indicator of the degree of similarity between biological sequences, for example, the percent of similar amino acids with similar functions and/or structures at similar positions between two aligned protein sequences.

The term "for example" or "e.g.," as used herein, means by way of example, without limitation intended, and should not be construed as referring only those items explicitly enumerated in the specification.

In accordance with long standing patent law convention, the words "a" and "an" when used in this application, including the claims, denote "one or more."

As used herein, the term "substrate" means a chemical compound that can be catalyzed by one or more of the proteases disclosed herein.

As used herein, the term "substantially free" or "essentially free" in connection with the amount of a component means a composition that contains less than about 10 weight percent, less than about 5 weight percent, and less than about 1 weight percent of a compound. In an embodiment, these terms refer to less than about 0.5 weight percent, less than about 0.1 weight percent, or less than about 0.01 weight percent.

The term "protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is intended to refer to any amino acid chain length, including those of short peptides from about 2 to about 20 amino acid residues in length, oligopeptides from about 10 to about 100 amino acid residues in length, and longer polypeptides including from about 100 amino acid residues or more in length. Furthermore, the term is also intended to include enzymes, i.e., functional biomolecules, including at least one amino acid polymer. Polypeptides and proteins of the present invention also include polypeptides and proteins that are or have been post-translationally modified, and include any sugar or other derivative(s) or conjugate(s) added to the backbone amino acid chain.

As used herein, the term "polypeptide" means a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including, without limitation, glycosylation, acetylation, phosphorylation, amidation, derivatization, proteolytic cleavage, post-translation processing, or modification by inclusion of one or more non-naturally occurring amino acids. Throughout the disclosure, common one-letter and three-letter amino acid abbreviations have been employed following the conventional nomenclature in the art: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M; Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "t" isomeric form may be substituted for any L-amino acid residue provided the desired properties of the polypeptide are retained. All amino-acid residue sequences represented herein conform to the conventional left-to-right amino-terminus to carboxy-terminus orientation.

As used herein, the term "operably linked" means a linkage of two or more polynucleotides or two or more nucleic acid sequences in a functional relationship. A nucleic acid is "operably linked" when it is placed into a functional relationship with another nucleic acid sequence. For instance, a promoter or enhancer is operably linked to a coding sequence if it affects the transcription of the coding sequence. "Operably linked" means that the nucleic acid sequences being linked are typically contiguous, or substantially contiguous, and, where necessary to join two protein coding regions, contiguous and within a reading frame. Since enhancers generally function when separated from the promoter by several kilobases (Kb) and intronic sequences may be of variable lengths; however, some polynucleotide elements may be operably linked but not contiguous.

The phrases "isolated" or "biologically pure" means material that is substantially, or essentially, free from components that normally accompany the material as it is found in its native state. Thus, an embodiment provides that the isolated peptides do not contain materials normally associated with the peptides in their in situ environment.

"Link" or "join" means any method well known by those of ordinary skill in the art for functionally connecting two or more molecules, including, without limitation, recombinant fusion, covalent bonding, disulfide bonding, ionic bonding, hydrogen bonding, electrostatic bonding, and such like.

As used herein, the terms "active," "biologically active," and "activity" mean biological activity associated with a particular protein or amino acid sequence and are used interchangeably herein. For example, the enzymatic activity associated with a lipase is hydrolysis and/or alcoholysis, i.e., ethanolysis, so as to hydrolyze or esterify at least a portion of a trans-fatty acid or carboxylic acid moiety. Lipase activity is measured as the ability to hydrolyze and/or esterify at least a portion of a trans-fatty acid or carboxylic acid moiety.

Certain embodiments also encompass DNA sequences that are complementary, or essentially complementary, with one or more of the specific sequences set forth herein. Nucleic acid sequences that are "complementary" are those that are capable of base pairing according to the standard Watson-Crick complementarity rules. As used herein, the term "complementary sequences" means nucleic acid sequences that are substantially complementary, as may be assessed by the same nucleotide comparison set forth above, or are defined as being capable of hybridizing to one or more of the specific nucleic acid segments disclosed herein under relatively stringent conditions such as those described immediately above.

The tem' "a sequence essentially as set forth in SEQ ID NO:X" means that the sequence substantially corresponds to at least a first portion of SEQ ID NO:X and has relatively few nucleotides that are not identical to, or a biologically functional equivalent of, the nucleotides of SEQ ID NO:X. Accordingly, sequences that have about 85% to about 90%; about 91% to about 95%; or about 96% to about 99% of nucleotides that are identical or functionally equivalent to one or more of the nucleotide sequences provided herein are particularly contemplated to be useful in the practice of the invention. In the context of peptides, polypeptides, and proteins, the term "a sequence essentially as set forth in SEQ ID NO:X" means that the sequence substantially corresponds to at least a first portion of SEQ ID NO:X and has relatively few amino acid residues that are not identical to, or a biologically functional equivalent of, the amino acid residues of SEQ ID NO:X. The term "biologically functional equivalent" is well understood by one of ordinary skill in the art, and is further defined in detail herein. Accordingly, peptide, polypeptide, or protein sequences that have about 85% to about 90%; about 91% to about 95%; or about 96% to about 99% of the amino acids that are identical or functionally equivalent to one or more of the amino acid sequences provided herein are particularly contemplated to be useful in the practice of the invention.

As used herein, the term "primer" refers to a single-stranded oligonucleotide that acts as a point of initiation of template-directed DNA synthesis using well-known methods (e.g., PCR) including, but not limited to those described herein. The appropriate length of a primer depends on its particular use, but typically ranges from about 15 to about 30 nucleotides or so.

As used herein, the term "expression" means the biological production of a product encoded by a coding sequence. In most cases, a polynucleotide (i.e., DNA) sequence, including the coding sequence, is transcribed to form a messenger-RNA (mRNA). The messenger-RNA is then translated to form a polypeptide product that has a relevant biological activity. The process of expression may involve further processing steps to the RNA product of transcription, such as splicing to remove introns, and/or post-translational processing of a polypeptide product.

As used herein, the term "heterologous" is used in relation to a predetermined referenced gene sequence. For example, with respect to a structural gene sequence, a heterologous promoter is defined as a promoter that does not naturally occur adjacent to the referenced structural gene, but which is positioned by laboratory manipulation. Likewise, a heterologous gene or nucleic acid segment or sequence is defined as a gene or segment that does not naturally occur adjacent to the referenced promoter and/or enhancer elements. Similarly, the term "heterologous" is also used in relation to a predetermined amino acid sequence. For example, with respect to an amino acid sequence, a heterologous protein tag, such as a poly-histidine tag, is defined as a peptide sequence that does not naturally occur adjacent to the referenced amino acid sequence. Likewise, a heterologous amino acid segment or sequence is defined as a segment or sequence that does not naturally occur adjacent to the referenced tag. Additionally, a heterologous protein refers to a protein that is not natively produced by or found within a particular organism. This can occur, for example, by the cloning and expression of a non-native lipase gene in a host organism such as E. coli.

As used herein, the term "protease variant" means a protease that differs from the native or wild-type protease from which it is derived by the substitution, insertion, and/or deletion of one or more amino acid residues at one or more sites within the polypeptide sequence of the "parent" protease; in the case of amino acid substitutions, the variant is typically substituted at one or more amino acid residues by one or more other amino acid residue(s) not ordinarily found in the corresponding, unsubstituted, or "wild-type" protease.

As used herein, the term "primer" or "primer sequence" refers to any nucleic acid sequence or segment that selectively hybridizes to a complementary template nucleic acid strand ("target sequence") and functions as an initiation point for the addition of nucleotides to replicate the template strand. Primer sequences of the present invention may be labeled or contain other modifications which allow the detection and/or analysis of amplification products. In addition to serving as initiators for polymerase-mediated duplication of target DNA sequences, primer sequences may also be used for the reverse transcription of template RNAs into corresponding DNAs.

As used herein, the term "structural gene" means a polynucleotide that is expressed to produce an encoded peptide, polypeptide, protein, ribozyme, catalytic RNA molecule, or antisense molecule.

A "target sequence" or "target nucleotide sequence" as used herein includes any nucleotide sequence to which one of the primer sequences hybridizes under conditions which allow an enzyme having polymerase activity to elongate the primer sequence, and thereby replicate the complementary strand.

As used herein, the term "transformation" means a process of introducing an exogenous polynucleotide sequence (e.g., a viral vector, a plasmid, or a recombinant DNA or RNA molecule) into a host cell or protoplast in which the exogenous polynucleotide is incorporated into at least a first chromosome or is capable of autonomous replication within the transformed host cell. Transfection, electroporation, and "naked" nucleic acid uptake all represent examples of techniques used to transform a host cell with one or more polynucleotides.

As used herein, the term "transformed cell" means a host cell whose nucleic acid complement has been altered by the introduction of one or more exogenous oligo- or polynucleotides into that cell.

As used herein, the term "vector" refers typically to a nucleic acid molecule (typically comprised of DNA) capable of replication in a host cell and/or to which another nucleic acid segment can be operatively linked so as to bring about replication of the attached segment. A plasmid, cosmid, or a virus is an exemplary vector.

The terms "substantially corresponds to," "substantially homologous," or "substantial identity" as used herein denotes a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared. The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more oligo- or polynucleotide sequences, the reference sequence will typically comprise at least about 10-15 nucleotides, more typically at least about 16 to 25 nucleotides, and even more typically at least about 26-35 nucleotides, at least about 40 nucleotides, at least about 45 nucleotides, at least about 50 nucleotides, or at least about 60, 70, 80, 90, or even at least about 100 or so nucleotides.

Preferably, when highly homologous fragments are desired, the percent identity between the two sequences (often referred to as "target" and "probe" sequences) will be at least about 80% identical, preferably at least about 85% identical, and more preferably at least about 90% identical, at least about 92% identical, at least about 93% identical, at least about 94% identical, or even at least about 95%, 96%, 97%, 98%, or 99% or higher. The percentage of homology or percentage of identity between 2 or more oligo- or polynucleotide sequences may readily be determined by one of skill in the art, using one or more of the standard sequence comparison algorithms, such as, e.g., the FASTA program analysis described by Pearson and Lipman (1988).

The term "naturally-occurring" as used herein as applied to an object refers to the fact that an object can be found in nature. For example, a polypeptide or polynucleotide sequence that is present in an organism that can be isolated from a source in nature and which has not been intentionally modified by the hand of man in a laboratory is naturally-occurring.

The term "substantially complementary," when used to define either amino acid or nucleic acid sequences, means that a particular subject sequence, for example, an oligonucleotide sequence, is substantially complementary to all or a portion of the selected sequence, and thus will specifically bind to a portion of an mRNA encoding the selected sequence. As such, typically the sequences will be highly complementary to the rnRNA "target" sequence, and will have no more than about 1, 2, 3, 4, 5, 6, 7, 8, 9, or 10 base mismatches throughout the complementary portion of the sequence. In many instances, it may be desirable for the sequences to be exact matches, i.e., be completely complementary to the sequence to which the oligonucleotide specifically binds, and therefore have zero mismatches along the complementary stretch. As such, highly complementary primer or probe sequences will typically bind quite specifically to the target sequence region of the plurality of polynucleotides and will therefore be highly efficient in directing amplification of the target sequence via real-time PCR.

Substantially complementary oligonucleotide sequences will be greater than about 80 percent complementary, greater than about 85 percent complementary, greater than about 90 percent complementary, or even greater than about 95 percent complementary (or "% exact-match") to the corresponding target nucleic acid sequence to which the oligonucleotide specifically binds, and will, more preferably be greater than about 96% or higher complementary to the corresponding nucleic acid sequence to which the oligonucleotide specifically binds. In certain aspects, as described above, it will be desirable to have even more substantially complementary oligonucleotide sequences for use in the practice of the invention, and in such instances, the oligonucleotide sequences will be greater than about 96%, 97%, 98%, 99%, or even 100% complementary to all or a portion of the target nucleic acid sequence to which the designed oligonucleotide probe or primer specifically binds.

Percent similarity or percent complementary of any of the disclosed sequences may be determined, for example, by comparing sequence information using the GAP computer program, version 6.0, available from the University of Wisconsin Genetics Computer Group (UWGCG). The GAP program utilizes the alignment method of Needleman and Wunsch (1970). Briefly, the GAP program defines similarity as the number of aligned symbols (i.e., nucleotides or amino acids) that are similar, divided by the total number of symbols in the shorter of the two sequences. The preferred default parameters for the GAP program include: (1) a unary comparison matrix (containing a value of 1 for identities and 0 for non-identities) for nucleotides, and the weighted comparison matrix of Gribskov et al., (2) a penalty of 3.0 for each gap and an additional 0.10 penalty for each symbol in each gap; and (3) no penalty for end gaps.

As used herein, "fluorescence resonance energy transfer pair" or "FRET pair" refers to a pair of fluorophores comprising a donor fluorophore and acceptor fluorophore, wherein the donor fluorophore is capable of transferring resonance energy to the acceptor fluorophore. In preferred fluorescence resonance energy transfer pairs, the absorption spectrum of the donor fluorophore does not substantially overlap the absorption spectrum of the acceptor fluorophore. As used herein, a "donor" probe refers to a probe that is labeled with a donor fluorophore of a fluorescent resonance energy transfer pair. As used herein, an "acceptor" probe refers to a probe that is labeled with an acceptor fluorophore of a fluorescent resonance energy transfer pair. In some cases, the donor and the acceptor may both be operably linked to a single probe, or, as is often the case in oligonucleotide-based FRET analysis, each is operably linked to dinstinct probes. As used herein, a "FRET oligonucleotide pair" will typically comprise an "anchor" or "donor" oligonucleotide probe and an "acceptor" or "sensor" oligonucleotide probe, and such a pair forms a fluorescence resonance energy transfer (FRET) relationship when the donor oligonucleotide probe and the acceptor oligonucleotide probe are both hybridized to their complementary target nucleic acid sequences. Acceptable fluorophore pairs for use as fluorescent resonance energy transfer pairs are well known to those skilled in the art and include, but are not limited to, fluorescein/rhodamine, phycoerythrin/Cy7, fluorescein/Cy5, fluorescein/Cy5.5, fluorescein/LC Red 640, fluorescein/LC Red 705, and combinations thereof.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Autoproteolytic Activity of Tau Oligomers

This example describes the identification of the autoproteolytic activity of tau oligomers. The study demonstrates that tau 4R2N undergoes autoproteolytic cleavage (i.e., self-cleavage) when it forms disulfide-mediated oligomers upon incubation at 37° C. in reaction buffer (25 mM Tris-HCl pH 7.4). Tau 4R1N showed similar properties.

Purified recombinant human tau 4R2N was prepared as described in the flow chart. Monomer, dimer and trimer species were purified preparative electrophoresis from a tau 4R2N preparation that had formed oligomers. The electrophoresis buffer contained 0.1% SDS which inhibited the proteolytic activity. Fractions containing the tau species were buffer exchanged into 25 mM Tris-HCl pH 7.4 using and Amicon ultrafiltration device (Merck Millipore, Billerica, Mass.), which led to restoration of tau autoproteolytic activity. Protein concentrations of the preparations were determined using the BCA kit (ThemoFisher Scientific).

Samples were run on a pre-cast 4-20% polyacrylamide Tris-HCl gel (BioRad, Hercules, Calif.) without using reductant in order to visualize the disulfide mediated oligomers. The gel was stained with GelCodeBlue Safe (ThermoFisher Scientific, Rockford, Ill.). Lane 1: 5.2 µg of tau 4R2N oligomer standard; Lane 2: 2 microliter of monomer fraction before buffer exchange; Lane 3: 0.5 µg monomer after buffer exchange; Lane 4: 5 pL of dimer fraction before buffer exchange; Lane 5: 0.5 µg dimer after buffer exchange; Lane 6: 20 µL trimer fraction before buffer exchange; Lane 7: 0.5 µg trimer after buffer exchange.

Tau 4R2N undergoes autoproteolytic cleavage (self-cleavage) when it forms disulfide-mediated oligomers upon incubation. Tau autoproteolyic activity co-purified with the dimer and trimer species. The amount of autoproteolytic activity was greatest with trimer which fragmented to the extent where no full size trimer remained after incubation. Dimer also showed autoproteolytic activity, whereas monomer only showed minor activity subsequent to forming oligomers upon incubation. This shows that tau protein has proteolytic activity, indicated by self-fragmentation, and that oligomer formation was necessary for the observable proteolytic activity. This also shows that the trimer form is more active than the dimer form which in turn is more active than an oligomer ladder formed from monomer. It was also shown that Tau autoproteolytic activity co-purified with dimer and trimer species. This autoproteolytic activity was observed with trimer activity>>dimer activity>>monomer activity. Full-length trimer digested completely into smaller fragments, and upon incubation, monomer formed an oligomeric ladder that produced a low level of autoproteolytic activity.

Example 2—Protease Activity of Purified Monomer, Dimer, and Trimer

This example describes the results of studies demonstrating the protease activity of purified tau monomers, dimers, and trimers. Monomer, Dimer, and Trimer of Tau 441 were purified under non-reducing conditions using continuous-elution electrophoresis. Fractions of each oligomer sample were pooled and buffer exchanged into stabilization buffer using an Amicon spin concentrator with a molecular weight cut-off of 30,000 daltons. 0.35 µg of each sample was incubated overnight at 37° C. while non-incubated control was kept on ice at 4° C. Next day, 2×SDS sample buffer without reductant was added to each sample and loaded onto a 4-20% gradient Tris-HCl Criterion Gel (Bio-Rad, Hercules, Calif.).

Multiple lots of Tau 4R2N protease have been produced to date and show similar properties of protease activity only after formation of disulfide mediated aggregates with maximal activity for the trimer. Lane 1—Oligomer Ladder: Lane 2—Monomer no incubation; Lane 3—Monomer with incubation; Lane 4—Dimer no incubation; Lane 5—Dimer with incubation; Lane 6—Trimer no incubation; Lane 7—Trimer with incubation; and 4°=Tetramer; 3°=Trimer; 2°=Dimer; 1°=Monomer.

Tau trimer activity>>tau dimer activity>>tau monomer activity

During incubation, tau monomer and tau dimer form higher order aggregates as observed as distinct upper bands (shown in box 1), whereas trimer does not form additional higher order aggregates (shown in box 2). Lack of reactivity to form higher order oligomers suggested that the trimer structure contains few free thiols because they are already in a disulfide linkage or are sterically hindered. This experiment reproduces the results from Example 1 showing the highest activity for trimer followed by dimer. The purified tau 4R2N trimer from this preparation also is seen not to form any additional higher order species during incubation which may indicate that it does not have any free thiols or that any free thiols that exist are sterically hindered and thus unreactive.

Multiple lots of Tau 4R2N protease have been produced and each showed similar properties of protease activity only after formation of disulfide mediated aggregates with maximal activity for the trimer. During incubation, tau monomer and tau dimer formed higher order aggregates as observed as distinct upper bands, whereas trimer did not form additional higher order aggregates. Lack of reactivity to form higher order oligomers confirmed that the trimer structure contained few free thiols because they were already in a disulfide linkage or were sterically hindered.

Example 3—Contamination Control Study

This example presents results from a contamination control study of tau protease. Monomer, Dimer, and Trimer of Tau 441 were purified under non-reducing conditions using continuous-elution electrophoresis. Fractions of each oligomer sample were pooled and buffer exchanged into stabilization buffer using an Amicon spin concentrator with a molecular weight cut-off of 30,000 daltons. 0.35 µg of each sample was incubated overnight at 37° C. while non-incubated control was kept on ice at 4° C. Next day, 2× sodium dodecyl sulfate sample buffer without reductant was added to each sample and loaded onto a 4-20% gradient Tris-HCl Criterion Gel (Bio-Rad, Hercules, Calif.).

It was shown that tau trimer is preferentially degraded whereas minimal cleavage of monomer and dimer using equal sample volumes from purification which would contain equal amounts of contaminating protease if it were responsible for the activity. Lane 1—tau oligomer ladder standard; Lane 2—empty; Lane 3—purified monomer no incubation (fraction from purification plate); Lane 4—purified monomer without incubation; Lane 5—purified monomer with incubation; Lane 6—purified dimer without incubation; Lane 7—purified dimer with incubation; Lane 8—purified trimer without incubation; purified trimer with incubation overnight at 37° C. Lanes 3-9 were treated with sample buffer containing β-mercaptoethanol (BME). The results of this study demonstrated that tau trimer was preferentially degraded, whereas minimal cleavage of monomer and dimer were observed when equal sample volumes from purification were used.

During preparation, the same volumes of monomer, dimer and trimer were pooled and buffer exchanged and concentrated such that each sample was exposed to the same amount of buffer. This controls for any contaminating proteases that would be contained within the buffers used during this step of the purification.

Example 4—Development of Stabilization Buffer for Tau Protease

This example describes the development and characterization of a stabilization buffer for preserving the activity of tau protease. An enzyme stabilization buffer has been developed that contains 0.002% SDS, which is the minimal inhibitory concentration for the enzymatic activity. The stabilization buffer contained 50 mM Tris, pH 7.4 and 0.002% sodium dodecyl sulfate. Dilution of the tau protease enzyme greater than or equal to 10-fold in reaction buffer restored activity.

For each sample, 0.3 μg of purified tau 4R2N trimer was incubated overnight at 37° C. in the presence of varying amounts of sodium dodecyl sulfate in 50 mM TrisHCl pH 7.4. Serial dilutions of SDS in 50 mM TrisHCl pH 7.4 were prepared on ice and a fixed volume of tau 4R2N trimer was added to each dilution. The samples were incubated overnight at 37° C. while the non-incubated control was kept on ice in 4° C. The next day, 2×SDS with reductant was added to each sample and loaded onto a 4-20% gradient Tris-HCl Criterion gel (Bio-Rad, Hercules, Calif.).

The concentration of SDS tested was Lane 1=0%; Lane 2=0.000050%; Lane 3=0.000100%; Lane 4=0.000200%; Lane 5=0.000390%; Lane 6=0.000780%; Lane 7=0.001560%; Lane 8=0.003130%; Lane 9=0.006250%; Lane 10=0.012500%; Lane 11=0.025000%; Lane 12=0.050000%; Lane 13=0.100000%. Lane 14=empty; Lane 15=Tau 4R2N monomer with beta mercaptoethanol This study permitted the formulation of a buffer whereby the tau protease is stable that can be activated by a dilution of 10 fold in reaction buffer (i.e., 25 mM Tris pH 7.4). An enzyme stabilization buffer has been developed that contains 0.002% SDS, which is the minimal inhibitory concentration for the enzymatic activity. Dilution of the Tau Protease enzyme greater than or equal to 10-fold in reaction buffer restores activity

Example 5—Stabilization Buffer Prevents Self-Cutting

This example demonstrates that the stabilization buffer described in Example 4 prevented self-cutting of the tau protein by its proteolytic domain, and permits the production of full-length monomer, dimer and trimer tau proteases.

Purified tau 4R2N monomer, dimer, and trimer individual fractions were buffer exchanged into stabilization buffer using Amicon spin concentrators with a molecular weight cut-off of 30,000 daltons. The same day, an aliquot of each oligomer sample was prepared for gel analysis by addition of 2×SDS without reductant followed by loading onto a 4-20% gradient TrisHCl Criterion gel (Bio-Rad, Hercules, Calif.).

Stabilization buffer enables production of full length monomer, dimer and trimer for tau protease. Lane 1—unpurified tau 4R2N oligomer ladder; Lane 2—empty; Lane 3—empty; Lane 4—Tau 4R2N purified monomer in stabilization buffer; Lane 5—Tau 4R2N purified dimer in stabilization buffer; Lane 6—Tau 4R2N trimer in stabilization buffer.

The results showed that intact monomer, dimer and trimer can be purified and remain stable in the stabilization buffer described in example 3.

Example 6—Tau Monomer, Dimer, and Trimer Degradation

The study presented in this example demonstrates the mass determination of 5 tau fragments. Fragments from tau trimer, dimer and monomer degradations were purified and subject to mass spectroscopy analysis. Fragment 3 was cut at 340KS341 based on N-terminal sequencing, and at 353KI354 and 370KI371 based on mass determination. Fragments 1-4 were shown to have the same N-terminus indicating that they were all cut at 130KS131, but differ on the C-terminus. Table 3 reports the apparent molecular weights of the fragments using molecular weight marker size standards to generate a standard curve.

TABLE 2

MASSES FROM MALDI MW DETERMINATION FOR FRAGMENT 3

| m/z | Intensity | MW Determination [Da] (Average) |
|---|---|---|
| 1080.98 | 9735.00 | 1079.98 |
| 1098.05 | 4191.55 | 1097.05 |
| 1255.91 | 1803.00 | 1254.91 |
| 1271.43 | 2441.00 | 1270.43 |
| 1285.79 | 3085.00 | 1284.79 |
| 1344.30 | 1817.00 | 1343.30 |
| 1361.10 | 3121.00 | 1360.10 |
| 1531.69 | 27740.96 | 1530.69 |
| 1702.85 | 42540.61 | 1701.85 |
| 1724.20 | 25842.82 | 1723.20 |
| 1740.89 | 17117.26 | 1739.89 |
| 1928.69 | 3937.00 | 1927.69 |
| 2401.70 | 1924.00 | 2400.70 |
| 2572.03 | 20798.00 | 2571.03 |
| 2594.30 | 10060.00 | 2593.30 |
| 2610.25 | 7324.00 | 2609.25 |
| 3442.88 | 1726.00 | 3441.88 |

TABLE 3

N-TERMINAL SEQUENCING FOR FIVE FRAGMENTS

|  | 1 | 2 | 3 | 4 | 5 | 6 |
|---|---|---|---|---|---|---|
| Fragment F3 (6 kD) | S | E | K | L | D | F |
| 1 (25 kD) | S | K | D | G | T | G |
| 2 (30 kD) | S | K | D | G | T | G |
| 3 (35 kD) | S/V | K/P | D/P/(G) | G/(A) | T | G |
| 4 (37 kD) | S/(V) | K/(P/I) | D/P | G/(A) | T | G |

Preparation of low molecular weight tau fragment for mass determination and N-terminal sequencing. 50 μL of 2.45 mg/mL purified tau 4R2N dimer was incubated at 37° C. for 38.5 hrs to enable autoproteolysis. The sample was combined with an equal volume of 2× sample buffer (126 mM Tris-HCl pH 7.0, 20% glycerol, 4% SDS, 0.05% bromophenol blue) and run in 5 wells of a pre-cast 15% polyacrylamide Tris-glycine gel (BioRad). The gel was stained one hour with GelCode® Blue Safe (ThermoFisher Scientific) and destained overnight with highly purified water. The bands, indicated by arrow labeled F3, were excised and finely minced with a fresh razor blade (washed with water and ethanol) and incubated in 5 mM Tris-HCl pH 7.0 at 4° C. with agitation overnight. The buffer containing eluted protein was sent to Alphalyse for analysis. Higher-molecular-weight fragments 1-4 were prepared for N-terminal sequencing by transfer to a PVDF membrane. The fragments were visualized with Ponceau staining and excised with a cleaned fresh razor. The membrane-bound fragments were sent to Alphalyse for N-terminal sequence analysis. The N-terminal sequence of the four fragments was the same: SKDGTG (SEQ ID NO:18). This indicates that the cut site between amino acids K130 and S131 is a primary autoproteolytic site of tau protease.

Molecular weight determination by MALDI Mass Spectrometry (MALDI MS). In MALDI MS, the dissolved sample is deposited on a metal target and the peptides and proteins are co-crystallized with a light-absorbing matrix. A laser beam is directed at the dry matrix sample, the sample molecules are desorbed and ionized and the masses are measured in a timeof-flight (TOF) mass analyzer. Larger proteins are often observed in the mass spectrum (m/z) as singly (MH+), doubly (MH2 2+) and triply protonated (MH3 3+) ions. The mass of the protein is calculated as the average mass of the intact non-protonated protein. The MALDI process requires that the protein preparation is relatively pure from interfering salts and detergents, and usually results in mass determinations within 5-10 Da of intact proteins up to approximately 60 kDa. In the present analysis, the proteins were micro-purified using Millipore ZipTips® ($C_{18}$ material) according to the ZipTip® User Guide. The proteins were eluted with 50% methanol. The proteins were analyzed by MALDI mass spectrometry in linear mode using HCCA as matrix. The mass spectra were calibrated using external calibration.

N-terminal Edman sequencing was performed on an ABI Procise® 494 sequencer. The procedure determines the N-terminal amino acid sequence of proteins and peptides by the Edman degradation chemistry. The sequencing takes place on an acid-etched glass fiber disk or on a PVDF membrane.

Figure 6A:
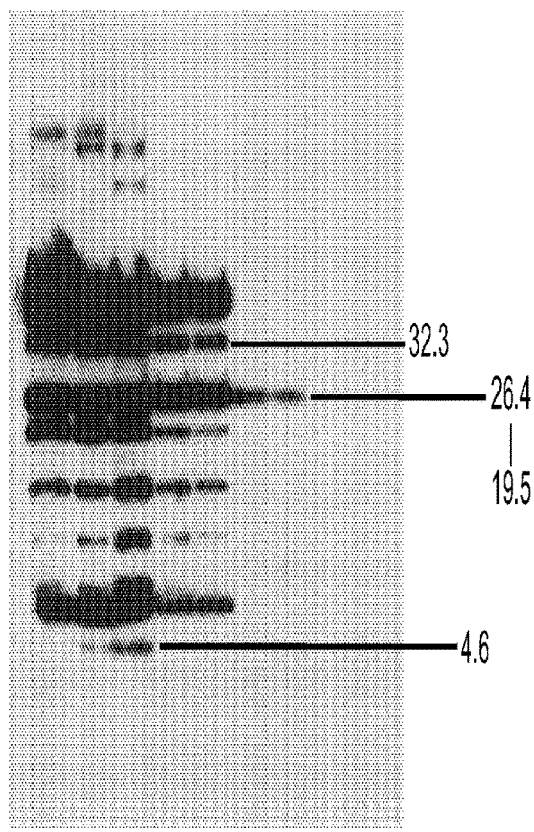
FIG. 6A and FIG. 6B show fragment-pairs identified from partial digests. Western blots were performed to identify fragments observed from a partial digest of tau 4R2N protein using antibodies specific for the C-terminus and N-terminus.

The Edman degradation is a cyclic procedure where amino acid residues are cleaved off one at a time and identified by chromatography. There are 3 steps in the cyclic procedure. In Step 1 the PITC reagent is coupled to the N-terminal amino group under alkaline conditions. In Step 2 the N-terminal residue is cleaved in acidic media. In Step 3, the PITC coupled residue is transferred to a flask, converted to a PTH-residue and identified by HPLC chromatography. The next cycle is then started for identification of the next N-terminal residue. The N-terminal sequence fo fragment F3 was determined to be SEKLDF corresponding to amino acids 341-346 of Tau 4R2N indicating that tau protease cut itself between lysine 340 and serine 341;

The isolation and sequencing of fragments enabled us to identify two cut sites in tau that we designate as primary cut sites because 4 fragments had the same n-terminus (cut at 130K-S131) and one fragment on the which is readily cleaved during the reaction (340K-S341) resulting in the loss of signal seen in the Western blot (FIG. 6A).

TABLE 4

FRAGMENT PAIRS IDENTIFIED FROM PARTIAL DIGESTS

| N-terminal Ab | C-terminal Ab | Cut Motif (P1-P1') |
|---|---|---|
| Matched Pairs | | |
| 11,826.1 | 32,262.6 | KS |
| 22,370.2 | 25,274.4 | KS |
| 25,969.3 | 20,903.5 | KS |
| 28,945.4 | 15,511.0 | KS |
| 33,149.7 | 11,826.1 | KS |
| 34,061.2 | 9,016.5 | KS |
| 41,183.2 | 6,781.9 | KS |
| 41,745.5 | 7,873.0 | KS |
| Match not found | | |
| | 14,692.0 | KT |
| | 18,252.4 | KT |
| | 19,799.8 | KT |
| 39,541.2 | | KS |

Table 4 shows the calculated MW from the tau 4R2N partial digest that were observed using Western blots with labeled antibodies specific for the C-terminus and N-terminus. The cut site motifs P1-P1' were identified in this analysis. Purified tau 4R2N monomer, dimer and trimer preparations were incubated for 0, 2 and 16 hours at 37° C. in buffer (25 mM Tris-HCl pH 7.4) and run on a 4-20% polyacrylamide Tris-HCl gel with sample buffer with reductant. From the left, lanes 1-3—monomer, 0, 2, 16 hr incubation; lanes 4-6—dimer 0, 2, 16 hr incubation; lanes 7-9—trimer, 0, 2, 16 hr incubation. The gel was stained with GelCode® Blue Safe (ThermoFisher Scientific) and the protein was transferred to a PVDF membrane (Merck Millipore, Billerica, Mass.). Immunoblots were performed using to identify fragments observed from a partial digest of tau 4R2N protein using an antibody specific for the C-terminus, epitope at amino acids 404-441 tau 4R2N (monoclonal T46, Life Technologies, Grand Island, N.Y.). The blot was stripped and reprobed with an antibody to the N-terminus, epitope at amino acids 83-120 tau 4R2N (monoclonal antibody T14, Life Technologies, Grand Island, N.Y.);

The molecular weight (MW) of the migrating fragments was determined by using the oligomer ladder as standard and plotting migration (Rf) versus the log(MW). For this calculation, the following MW were used: 45,900 Da for monomer; 91,800 Da for dimer; 137,700 Da for trimer; 183,600 Da for tetramer from which a standard curve was calculated and fitted linearly to $\log(Mw)=-0.5893Rf+5.5107$; $R^2=0.9832$. From the standard curve, the MW of monomeric tau was calculated to be 44,674 Da and differs from the actual MW by approximately 1,225 Da. Thus the calculated MW is an approximation of the actual MW (not the apparent MW).

Figure 1:
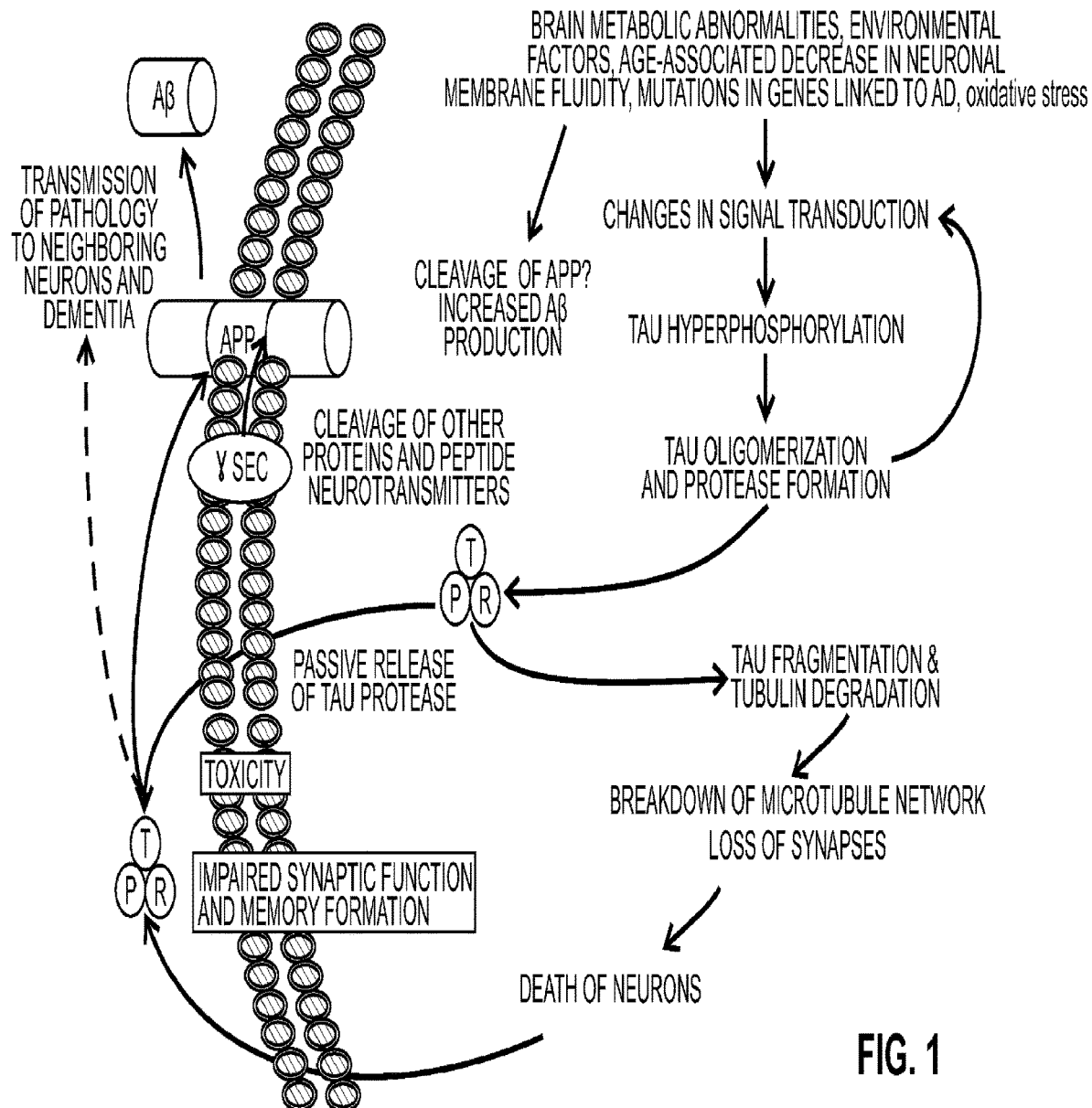
FIG. 1 shows tau protease disease mechanism in AD. Neuronal cellular stress can lead to oxidative conditions that favor intracellular formation of disulfide mediated tau oligomers if accompanied by accumulation of tau in the somatodendridic compartments. Mitochondrial dysfunction and inflammation can potentially stimulate the hyperphosphorylation of tau. These conditions are expected to lead to the formation of tau protease in conditions such as Alzheimer's disease. Once formed, these species undergo self cleavage leading to loss of function. Tau fragmentation has been identified as a key element in fibrils in disease. A large percentage of the fragmentation observed in disease may be the result of tau proteases autoproteolytic activity, and may represent the cells attempt to neutralize these neurotoxic species. Importantly, tau protease formation may also be associated with tau's gain of toxic function which could result from its proteolytic activity against other protein targets and neuropeptides. For example, cleavage of tubulin which can lead to microtubule disintegration, cleavage of APP adjacent to the β-secretase cut site which could generate Aβ(1-42) that could stimulate inflammation leading to BACE up regulation and expression. Cleavage of peptide neurotransmitters may play an important role in the disease symptomatology particularly early in disease.
Figure 2:
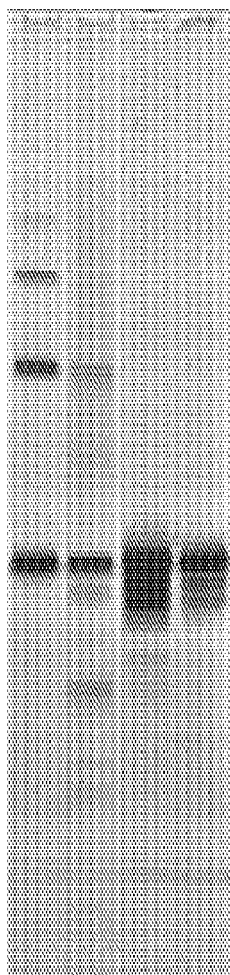
FIG. 2 illustrates the formation of disulfide mediated tau oligomers preceded truncation and higher order aggregate formation. Tau 4R2N oligomers were purified by continuous-elution electrophoresis and monomer was further purified by pooling and buffer exchanging using spin columns with a molecular weight cut-off of 7000 Da into 25 mM Tris-HCl pH 7.4. A small amount of the monomer was treated with freshly-prepared NEM at a final concentration of 1 mM for 2 hr at ambient temperature. For incubations, monomer treated and untreated with NEM was allowed to incubate at 37° C. over the weekend (approximately 50 hrs), followed by separation on 4-20% sodium dodecyl sulfate (SDS)-polyacrylamide gel electrophoresis (PAGE) (SDS-PAGE) Tris-HCl gel (Bio-Rad Catalogue #345-0033 Hercules, Calif., USA) without reductant. Tau 4R2N—Disulfide-mediated oligomer formation preceded truncation, and truncation preceded higher-order aggregation. Aggregate formation was time dependent. Tau 4R2N+N-ethylmaleimide (NEM Sigma Catalogue #04-260, St Louis, Mo., USA) irreversibly inhibited disulfide-mediated oligomer formation, leading to a loss of autoproteolytic activity, and inhibition of higher order aggregate formation. Lane 1: tau 4R2N that spontaneously formed an oligomeric ladder containing monomer, dimer, and trimer, and tetramer; Lane 2: upon incubation overnight at 37° C. tau 4R2N showed evidence of degradation but preferentially shows reduction in dimer, trimer, and tetramer relative to monomer; Lane 3: NEM-treated tau 4R2N does not readily form an oligomeric ladder; and Lane 4: NEM-treated 4R2N did not show evidence of degradation upon incubation overnight at 37° C. indicating the necessity for formation of disulfide for the enzymatic activity.
Figure 3:
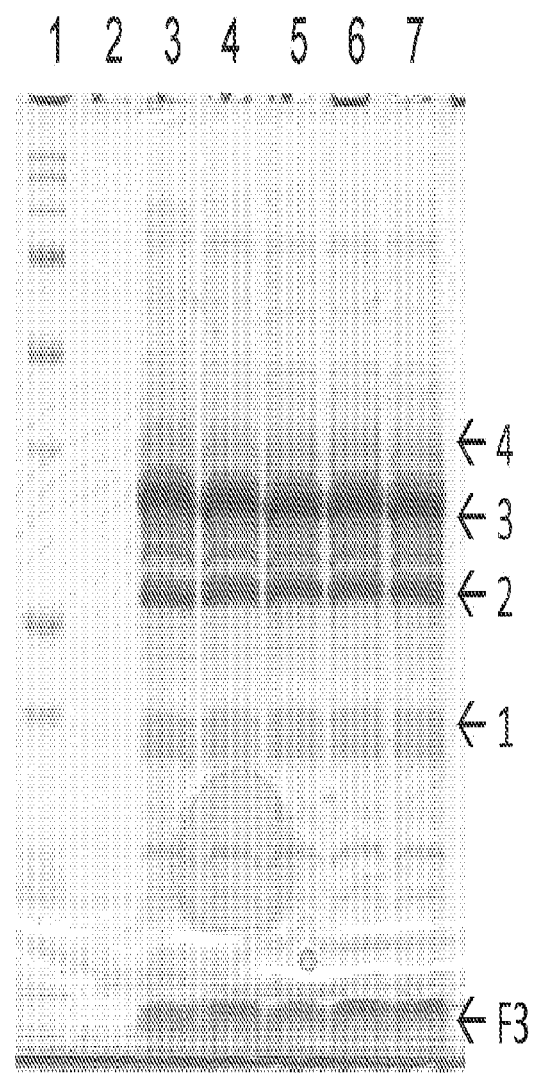
FIG. 3 shows the preparation of tau fragments for mass spectroscopy analysis and N-terminal sequencing. Fifty microliter of 2.45 mg/mL purified tau 4R2N dimer was incubated at 37° C. for 38.5 hr to enable autoproteolysis. The sample was combined with an equal volume of 2× sample buffer (126 mM Tris-HCl pH 7.0, 20% glycerol, 4% SDS, 0.05% bromophenol blue) and run in 5 wells of a pre-cast 15% polyacrylamide Tris-glycine gel (BioRad). The gel was stained 1 hr with GelCode™ Blue Safe Stain (ThermoFisher Scientific, Rockford, Ill., USA) and destained overnight with highly purified water. The bands, indicated by arrow labeled F3, were excised and finely minced with a fresh razor blade (washed with water and ethanol) and incubated in 5 mM Tris-HCl pH 7.0 at 4° C. with agitation overnight. The buffer containing eluted protein was sent to Alphalyse for analysis. Higher-molecular-weight fragments 1-4 were prepared for N-terminal sequencing by transfer to a PVDF membrane. The fragments were visualized with Ponceau staining and excised with a cleaned fresh razor. The membrane-bound fragments were sent to Alphalyse for N-terminal sequence analysis. The N-terminal sequence of the four fragments was the same: SKDGTG (SEQ ID NO:18). This indicates that the cut site between amino acids K130 and S131 is a primary autoproteolytic site of tau protease.
Figure 4:
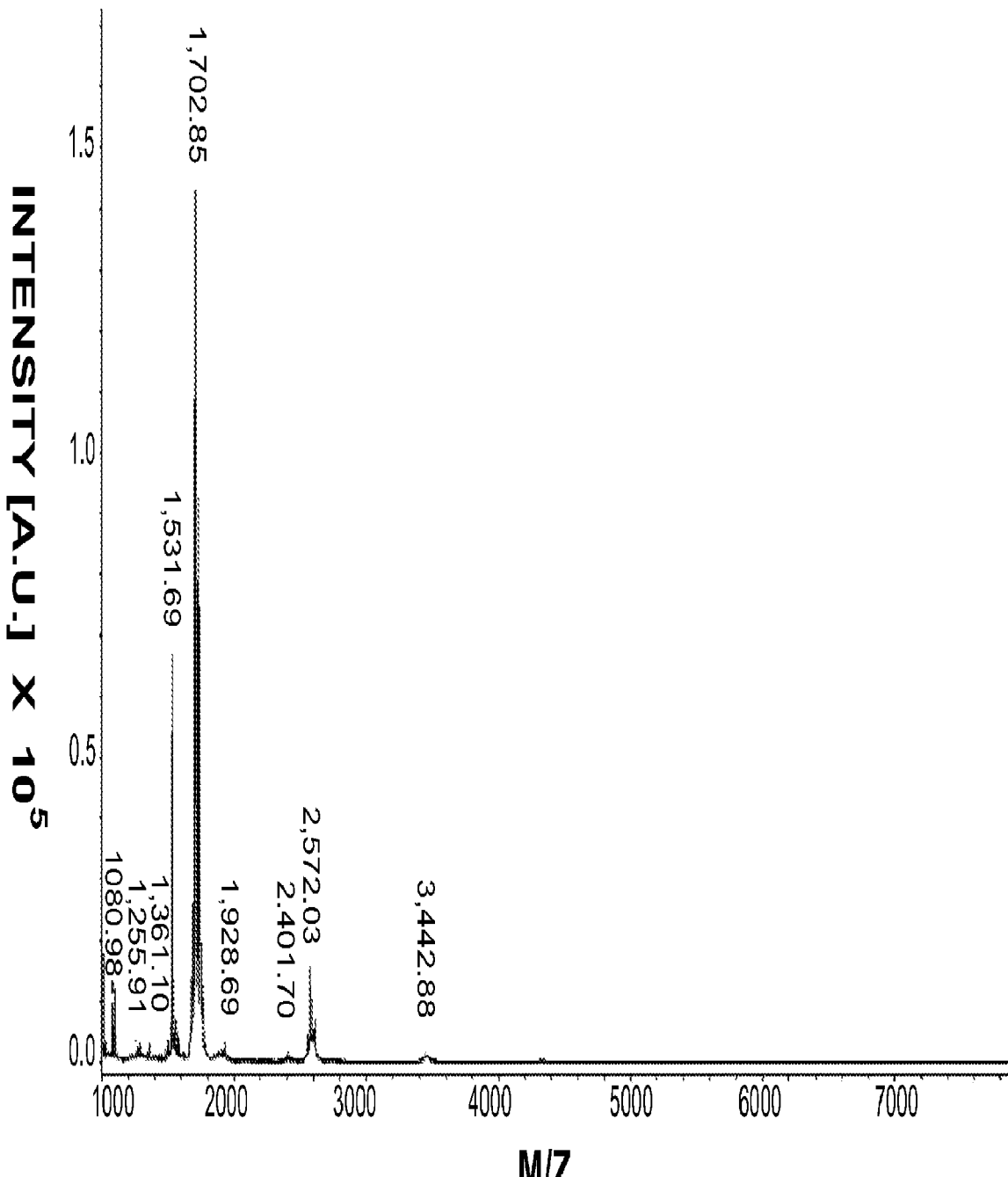
FIG. 4 shows the matrix-assisted laser desorption/ionization (MALDI) mass spectrum (MS) of Fragment F3 used to determine the fragment's molecular weight (MW). In MALDI MS, the dissolved sample is deposited on a metal target and the peptides and proteins are co-crystallized with a light-absorbing matrix. A laser beam was directed at the dry matrix sample, the sample molecules were desorbed and ionized and the masses were measured in a timeof-flight (TOF) mass analyzer. Larger proteins were often observed in the mass spectrum (m/z) as singly (MH+)–, doubly (MH2 2+)– and triply-protonated (MH3 3+) ions. The mass of the protein was calculated as the average mass of the intact non-protonated protein. The MALDI process requires that the protein preparation is relatively pure from interfering salts and detergents, and usually results in mass determinations within 5-10 Da of intact proteins up to approximately 60 kDa. In the present analysis, the proteins were micro-purified using pipette tips (ZipTips®, Merck Millipore, Billerica, Mass., USA) ($C_{18}$ material) according to the manufacturer's protocol. The proteins were eluted with 50% methanol. The proteins were analyzed by MALDI mass spectrometry in linear mode using HCCA as matrix. The mass spectra were calibrated using external calibration. N-terminal Edman sequencing was performed on an ABI PROCISE® 494 sequencer. The procedure determines the N-terminal amino acid sequence of proteins and peptides by the Edman degradation chemistry. The sequencing takes place on an acid-etched glass fiber disk or on a PVDF membrane. The Edman degradation is a cyclic procedure where amino acid residues are cleaved off one at a time and identified by chromatography. There are 3 steps in the cyclic procedure. In Step 1, the phenulisothiocyanate (PITC) Edman's reagent is coupled to the N-terminal amino group under alkaline conditions. In Step 2, the N-terminal residue is cleaved in acidic media. In Step 3, the PITC-coupled residue is transferred to a flask, converted to a PTH-residue and identified by HPLC. The next cycle is then started for identification of the next N-terminal residue. The N-terminal sequence for fragment F3 was determined to be SEKLDF (SEQ ID NO:18) corresponding to amino acids 341-346 of tau 4R2N indicating that tau protease cut itself between Lys340 and Ser341.

Matching the fragment pairs that summed to the molecular weight of the tau 4R2N MW of 45.9 kDa enabled identification of KS sites that were cut during the partial digest. In addition, fragments consistent with cutting at KT sites were also identified using this method. Thus, the tau cut site motifs identified from the mass spec and western blot were P1-K-(S, T or I)-P1'. The MW of each fragment observed on the western blots for the N and C terminal specific antibodies was calculated using this standard curve. Each possible fragment containing an N-terminus and each possible fragment containing a C-terminus are represented because the cleavage reactions did not go to completion. As such, the fragments can be recombined or matched such that the MW of the N-terminus+MW of the C-terminus approximates the MW of Tau 4R2N (45,900). From this analysis, 16 fragments were matched with an average calculated MW of 46,087 Da and a standard deviation of 2,267 Da. From the analysis, there were 4 unmatched fragments that could represent fragments cut at alternate sites. The results are consistent with cut sites identified via mass spectroscopy including K-S and K-I sites. A total of 12 cut sites for K-S and KI are expected from the sequence of tau 4R2N, but two sets of fragments are indistinguishable by PAGE based on anticipated MW of the fragments. Thus 20 out of 22 expected fragments were observed, with 16 fragments forming matched pairs. Four fragments do not apparently relate to cutting at K-S and K-I but are consistent with cutting at K-T which may represent secondary cut sites for tau protease. The fragments identified from this analysis allow us to identify the cut sites in tau that are most readily cut during the autoproteolytic reaction. This allows us to also see that in addition to cutting at K-S sites, that there is cutting at K-I and K-T sites in tau. Cutting at K-I sites is supported by the mass determination in FIG. 4.

Example 7—Tau 4R2N Proteolytic Fragments

Figure 6B:
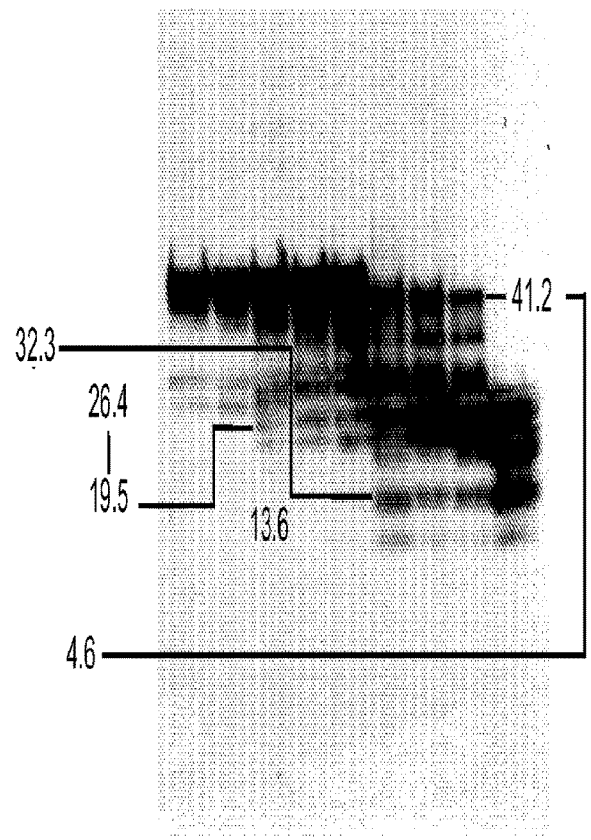

Based on the results presented in Table 4 and also the results of the n-terminal sequencing in Example 6 and the Western blot that probes at the n-terminal and c-terminal regions of full length tau (FIG. 6A, FIG. 6B) we can identify fragments that are likely to be generated. These fragments have potential utility as biomarkers and also may have intrinsic protease activity or be neurotoxic (hypothetical). Western blots were performed on incomplete digests that enabled identification of cut sites P1-K-(S, T, or I)-P1' for a total of 16 cut sites:

(SEQ ID NO: 5)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIINKKLDLSNVQSKCGSKDNIKHV

PGGGSVQIVYKPVDLSKVTSKCGSLGNIHHKPGGGQVEVKSEKLDFKDRV

QSKIGSLDNITHVPGGGNKKIETHKLTFRENAKAKTDHGAEIVYKSPVVS

GDTSPRHLSNVSSTGSIDMVDSPQLATLADEVSASLAKQGL.

Three of the observed cuts were primary cut sites seen in the tau 4R2N trimer protease autoproteolysis reaction (i.e., 130KS131, 340KS341, 353KI354, and 395KS396), which resulted in three fragments following an overnight incubation of the reaction mixture. The other 13 cuts observed were secondary cut sites, which may represent sites of TPR on monomeric or dimeric tau (i.e., 67KS68, 130KS131, 148KT149, 150KI151, 174KT175, 180KT181, 190KS191, 234KS235, 240KS241, 257KS258, 259KI260, 353KI354, 370KI371, 385KT386, and 395KS396).

Two primary cut sites 130KS131 and 340KS341 allowed us to identify the active fragment from TP-210 (131-340). After cloning this fragment we were able to demonstrate that it has protease activity (FIG. 7) and therefore this fragment spans the active site region of tau.

Based on the cut sites identified, there were 16 potential cut sites in tau. Complete digest yielded 17 fragments that are listed in Table 5. Partial digests potentially yielded 257 fragments. These fragments represent likely biomarkers for tau proteolytic activity in disease. Furthermore, since tau has an anionic N-terminus and a cationic C-terminus, it was expected that these fragments might display vastly different properties. Human blast on Fragment 15 showed that it is only present in tau, and tau derivatives, and in MAP4. This fragment may represent a highly-specific biomarker for AD. Also, due to its size, charge, and composition, it is expected to readily enter the plasma enabling detection of AD with a simple blood test.

TABLE 5

TAU 4R2N FRAGMENTS FROM CUTS AT KS, KT, AND KI

MAEPRQEFEVMEDHAGTYGLGDRKDQGGYTMHQDQEGDTDAGLKESPLQT
PTEDGSEEPGSETSDAK (SEQ ID NO: 23)

STPTAEDVTAPLVDEGAPGKQAAAQPHTEIPEGTTAEEAGIGDTPSLEDE
AAGHVTQARMVSK (SEQ ID NO: 24)

SKDGTGSDDKKAKGADGK (SEQ ID NO: 25)

TK (SEQ ID NO: 26)

IATPRGAAPPGQKGQANATRIPAK (SEQ ID NO: 27)

TPPAPK (SEQ ID NO: 28)

TABLE 5-continued

TAU 4R2N FRAGMENTS FROM CUTS AT KS, KT, AND KI

TPPSSGEPPK (SEQ ID NO: 29)

SGDRSGYSSPGSPGTPGSRSRTPSLPTPPTREPKKVAVVRTPPK (SEQ ID NO: 30)

SPSSAK (SEQ ID NO: 31)

SRLQTAPVPMPDLKNVK (SEQ ID NO: 32)

SK (SEQ ID NO: 33)

IGSTENLKHQPGGGKVQIINKKLDLSNVQSKCGSKDNIKHVPGGGSVQIV
YKPVDLSKVTSKCGSLGNIHHKPGGGQVEVK (SEQ ID NO: 34)

SEKLDFKDRVQSK (SEQ ID NO: 35)

IGSLDNITHVPGGGNKK (SEQ ID NO: 36)

IETHKLTFRENAKAK (SEQ ID NO: 37)

TDHGAEIVYK (SEQ ID NO: 38)

SPVVSGDTSPRHLSNVSSTGSIDMVDSPQLATLADEVSASLAKQGL
(SEQ ID NO: 39)

Example 8—Zymogram Analysis of Tau Protease Activity

Zymogram analysis was performed on a 4-16% PA tris-glycine gel system using blue casein, (10-well, Invitrogen, Inc.). Samples were run using non-reducing sample buffer, gel was washed 2× with purified water, 1×30 min 200 mL 25 mM Tris-HCl pH 7.0. The gels were incubated in 200 mL 25 mM Tris-HCl pH 7.0 at 37° C., and scanned after 2 hrs' incubation.

Zymogram analysis was performed on a 4-16% PA tris-glycine blue casein gel (Life Technologies, Grand Island, N.Y.). Clearing of the blue casein within the gel indicates proteolytic activity at that olocation within the gel. Samples were run using non-reducing sample buffer gel to maintain the disulfide-mediated oligomers. The gel was washed with purified water to remove the SDS which is inhibitory to protease activity, and equilibrated in reaction buffer (25 mM Tris-HCl pH 7.0). The gel was incubated in reaction buffer at 37 degrees Celsius for two hours, imaged and incubated an additional 18 hours. After the gel was imaged it was stained with GelCodeBlue Safe (ThermoFisher Scientific, Rockford, Ill.) to visualize the protein samples run into the gel and to correlate them with the observed protease activity within the gel. Lane 1—Protein standards, SeeBluePlus2 (Life Technologies, Grand Island, N.Y.); Lane 2-25 microgram Tau 4R2N oligomer ladder; Lane 3-25 microgram Tau 4R2N dimer; Lane 4-5 microgram Tau 4R2N dimer; Lane 5-1 microgram Tau 4R2N dimer.

The spatial correlation between tau protein bands and proteolytic activity indicated that the activity was intrinsic to tau and was not a contaminating protease. The higher order aggregates and tau fragments demonstrated activity by clearing of the blue casein. Clearing of blue casein was also found in the region of the monomer band from the tau oligomer ladder. It was subsequently demonstrated, by running the protein from this band on another gel, that tau had oligomerized within the gel at the location of the monomer band and that it had autoproteolytic activity. Another observation was that tau had the ability to cut the casein protein substrate in the zymogram.

Example 9—Tau 4R2N Trimer Protease Cuts Tubulin

Tau protease, in addition to its autocatalytic reaction, also cleaves tubulin. One of the major normal functions of tau is to facilitate the polymerization of tubulin into microtubules and to maintain their structure within the axons of neurons. This work shows that when tau forms oligomers it can degrade tubulin demonstrating a direct pathological mechanism for disruption of microtubules and neuronal function.

In a result not shown, tau 4R2N trimer cut tubulin. In that study, Lane 1—tubulin, no incubation; Lane 2—tubulin incubated without tau; Lane 3—tubulin with tau 4R/2N trimer, no incubation; Lane 4—tubulin incubated with tau 4R2N trimer. Incubation of tubulin alone led to the formation of some tubulin dimer but did not cause tubulin to fragment. Incubation of tubulin with tau4R2N trimer led to the formation of tubulin fragments and degradation of tubulin dimer.

Lyophilized tubulin (Cat# TL238, Cytoskeleton Inc.) was suspended in 200 μL buffer for 6 mg/mL solution. Samples were incubated for 19.25 hrs at 37° C. 10 μL 2× Laemmli sample buffer (BME) was added to each sample. Samples heated at 95° C. for 5 min in a thermal cycler with heated lid 5 min prior to loading.

α-endorphin is an endogenous opioid peptide whose amino acid sequence is: Tyr-Gly-Gly-Phe-Met-Thr-Ser-Glu-Lys-Ser-Gln-Thr-Pro-Leu-Val-Thr (SEQ ID NO:13). It is the 16-amino acid sequence of the N-terminal of β-endorphin and differs from gamma-endorphin by one amino acid (beta-endorphin 1-17). Thus, tau protease should cut all of these proteins because alpha endorphin is a sub-fragment of them.

The degradation of opioid peptides by tau protease in Alzheimer's disease may provide a mechanism for the mood changes associated with the disease, and inhibiting tau protease activity may have utility in improving mood disorder in the disease.

12 μg of α-endorphin peptide (Anaspec, Fremont, Calif.) was incubated with 1.2 μg of tau 4R/2N trimer in reaction buffer (25 mM Tris-HCl pH 7.4) for 20 hrs at 37° C. Reverse phase HPLC was used to monitor the cleavage of the peptide. The lower trace shows the peak for the intact peptide incubated without tau protease, and the upper trace shows the formation of peaks F1 and F2 indicating cleavage of alpha endorphin. The asterisk indicates an artifact peak that is derived from the incubation tube.

Amyloid precursor protein (APP) is cleaved to form Aβ, thought to be a key player in Alzheimer's disease pathology. The peptide derived from amino acids 667-676 of APP (SEV KMDAEFR) (SEQ ID NO:14) also contains the cleavage site for beta secretase which cuts APP to generate the N-terminus of A. Beta secretase cuts between M and D, whereas tau protease presumably cuts between K and M (underlined in peptide sequence).

Example 10—Tau Trimer Activity Inhibited by Protease Inhibitor Cocktail

Tau trimer protease was incubated with and without protease inhibitor cocktail overnight containing serine protease, amino-peptidase, cysteine protease and aspatic protease inhibitors. The protease inhibitor cocktail inhibited additional fragmentation consistent with an enzymatic function.

TABLE 6

SERINE SPECIFIC PROTEASE INHIBITOR EFFECT ON TRIMER ACTIVITY

| Inhibitor | Protese Class Specificity | Activity |
|---|---|---|
| Chymostatin | Serine (Chymotrypsin-like), Cysteine | ++ |
| Aproptinin | Serine (broad range) | + |
| Antipain | Calcium-dependent Serine and Cysteine | + |
| Trypsin Inhibitor | Serine (trypsin) | + |
| AEBSF | Serine | + |
| Phosphoramidon | Metalloproteases (thermolysin, collagenase) | − |
| Benzamidine HCl | Serine | − |
| Leupeptin | Serine, Cysteine | − |
| EACA | Plasminogen | − |
| Bestatin | Metalloprotease (aminopeptidase) | − |
| Pep statin | Aspartyl peptidases | − |
| NEM | Cysteine | − |
| EDTA | Metalloprotease | − |
| E-64 | Cysteine | − |

For each sample, 0.45 μg of tau 4R2N trimer was incubated at 0.2 mg/mL overnight at 37° C. in the presence of various freshly prepared protease inhibitors. Non-incubated control was kept on ice overnight at 4° C. Next day, 2× sodium dodecyl sulfate sample buffer with reductant was added to each sample and loaded onto a 4-20% gradient Tris-HCl Criterion Gel (Bio-Rad).

Protease inhibitors targeted include serine proteases, amino-peptidases, cysteine proteases, metallo-proteases, and aspartic proteases. S=Serine Protease Inhibitors; N=Non-specific Serine Protease Inhibitors. Lane 1=Non-incubated Control; Lane 2=Incubated Control; Lane 3=AEBSF; Lane 4=EACA; Lane 5=Antipain; Lane 6=Aprotinin; Lane 7=Benzamidine HCl; Lane 8=Chymostatin; Lane 9=EDTA; Lane 10=NEM; Lane 11=Leupeptin; Lane 12=Phosphoramidon; Lane 13=Trypsin Inhibitor; Lane 14=Pepstatin; Lane 15=Bestatin; and Lane 16=E-64. These results demonstrated that tau protease is a serine protease based on the classes of inhibitors that were active as shown in Table 6.

Example 11—TAMRA-FP Labeling of Tau Ladder 4-(2-Aminoethyl)benzenesulfonyl fluoride hydrochloride (AEBSF) was prepared fresh in anhydrous DMSO. (Sigma Chemical Co.) A8456-≥97%, Molecular Weight: 239.69; 9 mg AEBSF/187.2 μL DMSO=200 mM. Serine hydrolase FP probes were equilibrated to room temperature in pouch with desiccant. Serine hydrolase FP probe was dissolved in 100 μL of DMSO to make a 0.1 mM stock solution. Samples were aliquotted in 5-μL/tubes and store in −80° C. freezer. For the assay, samples were incubated 1 hr with AEBSF at room temperature then 0.5 μL TAMRA-FP added (4.55 μM final), mixed and incubated at room temperature for 4 hrs. 20 μL of 2× sample buffer (no BME) was added to samples, mixed, stored in a −80° C. freezer overnight.). 10 μL of each sample was transferred to another set of tubes containing 10 μL of 2× sample buffer (+BME), mixed and heated with "boil" program on thermal cycler. The remaining 30 μL of sample was loaded as is (this sample has multiple bands so ⅔ of sample was devoted to the non-reducing lanes). Samples were run on 4-20% PA gels with Tris-glycine, 18-well gel (BioRad).

Example 12—FP-TAMRA Labeling of Tau from AD Brain

This study showed the specific labeling of proteins with a probe for active serine hydrolases that were immunopurified with an antibody against tau protein from a specimen of Alzheimer's brain suggesting that tau protein has serine hydrolase activity. Serine hydrolases include a class of enzymes that include serine proteases. The serine hydrolase superfamily is one of the largest known enzyme families that share a catalytic mechanism that involves a serine nucleophile. Phenylmethanesulfonyl fluoride (PMSF) irreversibly binds to the active site serine of serine hydrolases to inactivate their enzymatic activity and prevents the probe from labeling them. The proteins in the bands that had reduced labeling after treatment with PMSF were specifically labeled by the probe for active serine hydrolases (indicated by arrows).

Protein was extracted from an AD brain by Dounce homogenization in TPER buffer (ThermoFisher Scientific) either 1 mM EDTA, 1 µg/mL pepstatin A, 20 mM phosphoramidon, or phosphatase inhibitor 1× (ThermoFisher Scientific). The lysate was cleared by centrifugation 10,000×g for 20 min. The supernatant was depleted for biotin using streptavidin-agarose (ThermoFisher Scientific). A probe specific for active serine hydrolases, fluorophosphonate (FP) labeled with a fluorescent carboxytetramethylrhodamine (TAMRA) tag (ThermoFisher Scientific), was incubated with the lysate at a final concentration of 2 µM. As a control for non-specific labeling, a portion of the lysate was treated with PMSF, an irreversible inhibitor of serine hydrolases including tau protease before using the FP-TAMRA probe. Biotinylated monoclonal antibody HT7 (ThermoFisher Scientific) was used to capture total tau from the lysate with Streptavidin agarose beads (ThermoFisher Scientific). Proteins bound by the antibody and captured by the beads were resolved by SDS-PAGE with or without the disulfide reductant β-mercaptoethanol (BME). Fluorescent images were captured with a Typhoon scanner (GE Healthcare). Assayed in Lane 1: Lysate after tau immunodepletion, no PMSF treatment; Lane 2: Lysate after tau immunodepletion, with PMSF treatment with PMSF; Lane 3: Immunocaptured protein, no PMSF treatment; Lane 4: Immunocaptured protein, with PMSF treatment. Left panel—no reductant; Right panel—reductant added to samples before loading gel.

AEBSF is a serine protease inhibitor. Inhibition constant was similar to those of PMSF and DFP. AEBSF inhibits trypsin, chymotrypsin, plasmin, kallikrein, and thrombin. The data in FIG. 15A showed AEBSF also inhibited tau protease activity. 10 uL of water was added to each sample and mixed before loading for HPLC analysis. 2 blanks run on HPLC before analysis of samples. Test of cutting peptide for FRET assay OP-002 using tau 441 trimer(2) and EnVision plate reader.

Samples were incubated for 23 hrs at 37° C. 10 µL of each sample was transferred to wells containing 40 µL of 25 mM Tris-HCl pH 7.4 in a black 96-well plate and mixed so that the sample covered the well bottom. A control well with 50 µL buffer was also employed. The gain on the EnVision® was lowered to 10 from 100 to reduce the counts so that the buffer only well was only 1 unit.

The resulting gel was subsequently used to prepare an immunoblot with monoclonal antibody BT2 (ThermoFisher Scientific) against tau. The immunoblot of the gel indicated the location of tau protein recognized by a tau-specific antibody. Signal from the serine hydrolase probe and the immunoblot in the same location supported the conclusion that tau was being labeled by the serine hydrolase probe. However, since the monoclonal antibody used for the immunoblot recognized a single epitope (small region) of tau only the fragments of tau containing this epitope is recognized by this antibody.

Example 13—Western Blot with C-Terminal Antibody

Results showed that when the C-terminus was cut, the signal was lost for antibody with epitope in a 30-amino acid region of the C-terminus of tau. This region of tau appears to be most readily cut and may represent an important biomarker for tau protease activity in vivo and in AD. The ratio of detection of total tau/detection with C-terminal antibody is a potential biomarker for AD.

From FIG. 6A, purified tau 4R2N monomer, dimer and trimer preparations were incubated for 0, 2 and 16 hours at 37 degrees Celsius in buffer (25 mM Tris-HCl pH 7.4) and run on a 4-20% polyacrylamide Tris-HCl gel with sample buffer with reductant. From the left, lanes 1-3—monomer, 0, 2, 16 hr incubation; lanes 4-6—dimer 0, 2, 16 hr incubation; lanes 7-9—trimer, 0, 2, 16 hr incubation. The gel was stained with GelCode™ Blue Safe (ThermoFisher Scientific) and the protein was transferred to a PVDF membrane (Merck Millipore, Billerica, Mass.). Immunoblots were performed using to identify fragments observed from a partial digest of tau 4R2N protein using an antibody specific for the C-terminus, epitope at amino acids 404-441 tau 4R2N (monoclonal T46, Life Technologies, Grand Island, N.Y.). The blot was stripped and reprobed with an antibody to the N-terminus, epitope at amino acids 83-120 tau 4R2N (monoclonal antibody T14, Life Technologies, Grand Island, N.Y.);

Example 14—Tau Protease Activity Detection Kit

The present example describes a Tau Protease Activity Assay Kit that has been designed for tau protease inhibitor screening. It provides all the reagents (including a sample of Tau protease for use as a positive control) required for an efficient detection of tau protease activity. The assay is based on a convenient method of fluorescence resonance energy transfer (FRET) in which the fluorescence signal enhancement is observed after the substrate is cleaved by tau protease.

Reagents:

An exemplary commercial formulation of the kit provides sufficient reagents for 250 reactions in 96-well microtiter plate format.
Fluorescent Assay Buffer 50 mL
Stop Solution 15 mL
Assay Standard Tau Protease, 1 vial
7-Methoxycumarin-4-acetyl 0.5 mg
Tau peptide fragment 334-342 (OP-002) GGQVEVKSE (SEQ ID NO:15) an example for any of the tau cut sites defined by KS, KI, or KM for example that can be used for a FRET based compound screening assay that is the substrate for the Tau Protease screening assay and that contains a fluorophore and quench such that fluorescent signal is observed upon cleavage by Tau Protease at the KS site.
Equipment and Reagents required but not included in the commercial form of the kit:
Fluorimeter
96-well microtiter plate for fluorescence assay
Dimethyl sulfoxide
Storage/Stability: The kit is shipped on dry ice and stored at 20° C. After first thaw, the Fluorescent Assay Buffer and Stop Solution should be stored at 2-8° C. Multiple freeze-thaw cycles of the substrate, enzyme, and standard should be avoided for optimum performance of the kit.

Reagent Preparation:The volume of reagents detailed below is for assays performed in 96-well plates. For plates or wells of different sizes, the amount of reagents required may be adjusted accordingly.

Tau Protease Substrate Solution:Prepare a 1 mg/mL solution by adding 0.5 mL of DMSO to the tau protease substrate. Aliquot the tau protease substrate solution and store at −20° C.

Just before beginning the assay, dilute an aliquot of the tau protease substrate solution 10-fold with Fluorescent Assay Buffer. Mix well.

Tau Protease Solution:Just before beginning the assay, dilute the Tau Protease 10-fold with Fluorescent Assay Buffer. Mix well.

Assay Standard Solution:

Just before beginning the assay, dilute the Assay Standard 10-fold with Fluorescent Assay Buffer. Mix well.

Assay Protocol:Set the fluorimneter on well plate reader mode with excitation at 320 nm, and emission at 405 nm. Bring all components (except the Tau Protease Enzyme Solution) to room temperature. Add components to a fluorimeter 96-well plate as described. Mix well by gentle pipetting. Add the Tau Protease Enzyme Solution just before reading.

Reaction 1: Negative control (no enzyme) reaction and standard curve blank. The "blank" reaction tube reflects fluorescence due to substrate alone.

Reaction 2: Positive control supplied with assay kit.
Reaction 3: Enzyme inhibition test.
Reaction 4: Sample enzyme activity test.

Read the fluorescence immediately after adding the enzyme. This is the "time zero" reading. The signal in the wells could increase between the addition of enzyme and this initial reading. Cover the plate with a Parafilm and incubate at 37° C. for 2 hrs. Read the signal at "time zero"+2 hrs. The plate should be at room temperature before reading. Optional: After the readings are made, add 40 μL of Stop Solution. The addition of the Stop Solution will stabilize the signal for at least 24 hrs.

Data Analysis:

The assay is designed so that the enzyme converts 5-20% of the substrate to a fluorescent product during 1-2 hrs at 37° C. To determine the standard curve, Subtract the fluorescence units (FU) of the blank value (reaction 1) from all signal readings (reactions 5-8) at 2 hrs. Plot the fluorescence units against pmol present in each standard. Typical Standard Curve y=1.3736x+8.7973 obtained using Perkin Elmerluminescence spectrometer ISSOB, excitation 320 nm (slit 12 nm) and emission 405 nm (slit 12 nm).

Calculation of the Percentage of Substrate Cleavage

The percentage of substrate cleavage is based on the fluorescence signal reading of tube 8. This reading reflects the fluorescence from the 500 pmol standard, which indicates 50% cleaved product, since the amount of the substrate in the reaction is 1,000 pmol. To calculate the percentage of substrate cleavage in the test sample subtract the FU value of the blank (reaction 1) and follow the equation below.S=amount (pmol) of fluorescent product in the test sample (reaction 4) as obtained from the standard curve.

% cleavage=S (pmol)
500 (pmol)

Assay of Tau Protease inhibitors

Enzyme activity inhibition reactions were set using reactions 1-3 (i.e., blank, enzyme activity reaction, and inhibition reaction tubes). Reaction 3 was expanded to include a few wells with different concentrations of the inhibitor and the reaction was performed at 37° C. for 2 hrs.

Example 15—Tau Protease UmuD' Protease Homology

Tau 268His-Tau 385Lys showed 35% homology at >90% consensus to UmuD', a serinelysine protease involved in the bacterial SOS response. UmuD was activated by RecA binding and an autoproteolysis reaction that cleaves a 24-aa fragment from the N-terminal tail. Amino acids with 100% match are given as the amino acid abbreviation between tau (upper sequence) and UmuD'.

Example 16—Protease-Active Tau Variants

```
TAU PROTEIN 4R2N FULL-LENGTH
                                        (SEQ ID NO: 6)
MAEPRQEFEVMEDHAGTYGLGDRKDQGGYTMEQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAVVRTPPKSPSSAKSRLQTAPVPM

PDLKNVKSKIGSTENLKHQPGGGKVQIINKKLDLSNVQSKCGSKDNIKHV

PGGGSVQIVYKPVDLSKVISKCGSLGNIHHKPGGGQVEVKSEKLDFKDRV

QSKIGSLDNITHVPGGGNKKIETHKLTFRENAKAKTDHGAEIVYKSPWSG

DTSPRHLSNVSSTGSIDMVDSPQLATLADEVSASLAKQGL (45

Serines)
```

Tau Protease Variants:

Lys274, Lys280, Lys281, Lys311, Lys340 and Lys343 (shown in the full-length sequence above in bold-face, underlined type) were evaluated for active site residues in the catalytic site. Lys274 is between β-turn and β-sheet structures and may be in close proximity to putative active site Ser305 when the there is a disulfide linkage between Cys291 and Cys322 and/or interaction between hexapeptide motifs PHF6* and PHF6. The adjacent Gly273 is also a mutation site in tauopathy frontotemporal dementia.

Lys280 is a mutation site in frontotemporal dementia in which it may be deleted and Lys281 may substitute for Lys280 in this scenario. The redundancy of lysines at this location suggests significance for this residue at this location. These lysines are also located at the carboxyl end of the β-sheet forming PHF6* hexapeptide motif. Lys311 is located at the carboxyl end of the β-sheet forming PHF6 hexapeptide motif. Lys340 is found at the carboxyl terminus of tau fragments formed by autocatalytic proteolysis. Lys343 corresponds to the active site lysine in the homologous serine protease UmuD.

The present example also describes tau protease variants that contain single amino acid substitutions in the wild-type 4R2N isoforms of the tau protein. Numbering is based on the wild-type 4R2N isoform of tau as shown in SEQ ID NO:6.

FTD Mutations in Tau Protein

R5H, R5L, K257T, I260V, L266V, G272V, G273R, N279K, ΔK280, L284V, N296A, N296H, P301L, P301S, P301T, G303V, G304S, S305I, S305N, L315R, K317M, S320F, P332S, G335S, G335V, Q336R, V337M, E342V, S352L, S356T, V363I, K369I, G389R, R406W, T427M 29 mutated sites in FTD with 37 coding region mutations, 20 of which involve removal or insertion of a Lysine, Serine, or Isoleucine. 19 are present in Tau truncated proteins TP-210 and TP-99 with 26 coding region mutations. 23 coding mutations have direct or potential affects on tau protease cut sites or active site serine:

2 eliminate putative tau protease cleavage sites: K257T eliminates 257KS258; and I260V eliminates 259KI260. 1 creates putative tau protease cleavage site: P332S. 2 substitute serines, one of which could be part of the catalytic triad, S305I and S305N. 6 are adjacent to tau protease cleavage sites (K257T adjacent to 259KI260; I260V adjacent to 257KS258; K369I adjacent to 370KI371; E342V adjacent to 340KS341; S352L adjacent to 353KI354; K369I adjacent to 370KI371). 17 create or eliminate or are adjacent to potential cleavage sites by one or two amino acids (R5H & R5L; L266V; G272V G273R; N279K, AK280, P301L, P301S, P301T, L315R, K317M, S320F, Q336R, E342V, S352L, G389R, and R406W).

Paired Helical Filament Regions:
Two mutations in PHF6*: N279K and AK280
Pro-Gly Repeat Regions:
Proline along with glycine repeat is more commonly found in sharp turns connecting β strands (β bends). Tau 81 contains three such regions 270PGGG273, 301PGGG304, 332PGGG335. In these three regions, there are 7 coding mutation sites in FTD and a total of 10 coding mutations. The mutations are: G272V, G273R, N279K, P301L, P301S, P301T, G304S, P332S, G335S, and G335V. In addition, there are a total of four mutations at the first amino acid position on the C-terminal side of two of the Pro-Gly repeat regions (S305I, S305N, S305S, and Q336R). Further, there is an additional mutation at the second amino acid position of the C-terminal side of one of the Pro-Gly repeat regions (V337M).
4 have no apparent association with tau protease:
L284L, ΔN296, N296A, and N296H Tau 4R2N with an amino acid substitution of Ser285 to Ala285: Tau 4R2N S285A
(SEQ ID NO: 40)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAWRTPPKSPSSAKSRLQTAPVPMP

DLKNVKSKIGSTENLKEQPGGGKVQIINKKLDLANVQSKCGSKDNIKHVP

GGGSVQIVYKPVDLSKVTSKCGSLGNIHHKPGGGQVEVKSEKLDFKDRVQ

SKIGSLDNITHVPGGGNKKIETHKLTFRENAKAKTDHGAEIVYKSPWSGD

TSPRHLSNVSSTGSIDMVDSPQLATLADEVSASLAKQGL

Ser285 (bold, underlined) was chosen as a putative active site serine because it follows residue Leu284 which is a site for mutations in the tauopathy frontotemporal dementia. Leu284 is also conserved in the alignment of this region to the active site region of serine protease umuD'.

Tau 4R2N with an amino acid substitution of Ser305 to Ala305: Tau 4R2N S305A
(SEQ ID NO: 41)
MAEPRQEFEVMEDHAGTYGLGDRKDQGGYTMHQDQEGDIDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAWRTPPKSPSSAKSRLQTAPVPMP

DLKNVKSKIGSTENLKEQPGGGKVQIINKKLDLSNVQSKCGSKDNIKHVP

GGGAVQIVYKPVDLSKVTSKCGSLGNIHHKPGGGQVEVKSEKLDFKDRVQ

SKIGSLDNITHVPGGGNKKIETHKLTFRENAKAKTDHGAEIVYKSPWSGD

TSPRHLSNVSSTGSIDMVDSPQLATLADEVSASLAKQGL

Ser305 (bold, underlined) was chosen as a putative active site serine because it is in the same region as the homologous active site region in umud' also which is situated between β-turn and β-sheet structures. Ser305 is also a frequent site for mutations in the tauopathy frontotemporal dementia. The β-turn region (Pro301-Gly304) immediately before Ser305 is a "hotspot" for mutations in frontotemporal dementia. Ser305 is also substituted with Lysine in tau 3R isoforms. Overexpression of tau 4R isoforms is frequently associated with tauopathies. Phosphorylation of Ser305 is also modulated in Alzheimer's disease.

Tau 4R2N with an amino acid substitution of Ser316 to Ala316: Tau 4R2N S316A
(SEQ ID NO: 42)
MAEPRQEFEVMEDHAGTYGLGDRKDQGGYTMHQDQEGDTDAGLKESPLQT

PTEDGSEEPGSETSDAKSTPTAEDVTAPLVDEGAPGKQAAAQPHTEIPEG

TTAEEAGIGDTPSLEDEAAGHVTQARMVSKSKDGTGSDDKKAKGADGKTK

IATPRGAAPPGQKGQANATRIPAKTPPAPKTPPSSGEPPKSGDRSGYSSP

GSPGTPGSRSRTPSLPTPPTREPKKVAWRTPPKSPSSAKSRLQTAPVPMP

DLKNVKSKIGSTENLKEQPGGGKVQIINKKLDLSNVQSKCGSKDNIKHVP

GGGSVQIVYKPVDLAKVTSKCGSLGNIHHKPGGGQVEVKSEKLDFKDRVQ

SKIGSLDNITHVPGGGNKKIETHKLTFRENAKAKTDHGAEIVYKSPWSGD

TSPRHLSNVSSTGSIDMVDSPQLATLADEVSASLAKQGL

Ser316 (bold, underlined) was chosen as a putative active site serine because is located between residues Leu315 and Lys317, both of which are sites for mutations in the tauopathy frontotemporal dementia.

| SUMMARY OF DISCLOSED POLYPEPTIDE AND POLYNUCLEOTIDE SEQUENCES | |
|---|---|
| SEQ ID NO: 1 | Polypeptide sequence of TP-210 |
| SEQ ID NO: 2 | Polypeptide sequence of TP-118 |
| SEQ ID NO: 3 | Polypeptide sequence of TP-99 |
| SEQ ID NO: 4 | Polypeptide sequence of TP-83 |
| SEQ ID NO: 5 | Polypeptide sequence of TP-81 |
| SEQ ID NO: 6 | Polypeptide sequence of full-length Tau Protein |
| SEQ ID NO: 7 | DNA sequence encoding TP-210 |
| SEQ ID NO: 8 | DNA sequence encoding TP-118 |
| SEQ ID NO: 9 | DNA sequence encoding TP-99 |
| SEQ ID NO: 10 | DNA sequence encoding TP-83 |
| SEQ ID NO: 11 | DNA sequence encoding TP-81 |
| SEQ ID NO: 12 | DNA sequence encoding full-length Tau Protein |
| SEQ ID NO: 13 | Human α-endorphin Peptide |
| SEQ ID NO: 14 | Human APP Peptide aa667-676 |
| SEQ ID NO: 15 | Tau Peptide OP-2 |
| SEQ ID NO: 16 | Tau Peptide OP-1 |
| SEQ ID NO: 17 | Human APP Protein |
| SEQ ID NO: 18 | N-Terminal Sequence of Fragment F3 |
| SEQ ID NO: 19 | aa335-353 of Tau Protease |
| SEQ ID NO: 20 | Human APP Peptide Fragment aa155-169 |
| SEQ ID NO: 21 | Human APP Peptide Fragment aa663-678 |
| SEQ ID NO: 22 | Human APP Peptide Fragment aa 746-759 |
| SEQ ID NO: 23 | Tau 4R2N fragment from Cuts at KS, KT and KI |
| SEQ ID NO: 24 | Tau 4R2N fragment from Cuts at KS, KT and KI |
| SEQ ID NO: 25 | Tau 4R2N fragment from Cuts at KS, KT and KI |
| SEQ ID NO: 26 | Tau 4R2N fragment from Cuts at KS, KT and KI |

SUMMARY OF DISCLOSED POLYPEPTIDE AND POLYNUCLEOTIDE SEQUENCES

| | |
|---|---|
| SEQ ID NO: 27 | Tau 4R2N fragment from Cuts at KS, KT and KI |
| SEQ ID NO: 28 | Tau 4R2N fragment from Cuts at KS, KT and KI |
| SEQ ID NO: 29 | Tau 4R2N fragment from Cuts at KS, KT and KI |
| SEQ ID NO: 30 | Tau 4R2N fragment from Cuts at KS, KT and KI |
| SEQ ID NO: 31 | Tau 4R2N fragment from Cuts at KS, KT and KI |
| SEQ ID NO: 32 | Tau 4R2N fragment from Cuts at KS, KT and KI |
| SEQ ID NO: 33 | Tau 4R2N fragment from Cuts at KS, KT and KI |
| SEQ ID NO: 34 | Tau 4R2N fragment from Cuts at KS, KT and KI |
| SEQ ID NO: 35 | Tau 4R2N fragment from Cuts at KS, KT and KI |
| SEQ ID NO: 36 | Tau 4R2N fragment from Cuts at KS, KT and KI |
| SEQ ID NO: 37 | Tau 4R2N fragment from Cuts at KS, KT and KI |
| SEQ ID NO: 38 | Tau 4R2N fragment from Cuts at KS, KT and KI |
| SEQ ID NO: 39 | Tau 4R2N fragment from Cuts at KS, KT and KI |
| SEQ ID NO: 40 | Tau 4R2N-derived Protease Variant S285A substitution |
| SEQ ID NO: 41 | Tau 4R2N-derived Protease Variant S305A substitution |
| SEQ ID NO: 42 | Tau 4R2N-derived Protease Variant S316A substitution |

REFERENCES

The following references, to the extent that they provide exemplary procedural or other details supplementary to those set forth herein, are specifically incorporated herein by reference.

Amos, L A, "Microtubule structure and its stabilization," *Org. Biomol. Chem.*, 2(15):2153-60 (2004).

Andorfer C, et al., "Hyperphosphorylation and aggregation of tau in mice expressing normal human tau isoforms," *J. Neurochem.*, 86(3):582-90 (2003).

Arnaud L, Myeku N, and Figueiredo-Pereira, N, "Proteasome caspase cathepsin sequence leading to tau phathology induced by prostaglandin J2 in neuronal cell," *J. Neurochem.*, 110:328-342 (2009).

Arriagada, P V, et al., "Neurofibrillary tangles but not senile plaques parallel duration and severity of Alzheimer's disease," *Neurology*, 42(3Pt 1):631 (1992).

Asuni, A A, et al., "Immunotherapy targeting pathological tau conformers in a tangle mouse model reduces brain pathology with associated functional improvements," *J. Neurosci.*, 27(34):9115-29 (2007).

Ballatore, C, Lee, V M, and Trojanowski, J Q, "Tau-mediated neurodegeneration in Alzheimer's disease and related disorders," *Nat. Rev. Neurosci.*, 8(9):663-72 (2007).

Bancher, C, et al., "Neuropathological staging of Alzheimer lesions and intellectual status in Alzheimer's and Parkinson's disease patients," *Neurosci. Lett.*, 162:179 (1993).

Berger, Z, et al., "Accumulation of pathological tau species and memory loss in a conditional model of tauopathy," *J. Neurosci.*, 27(14):3650-62 (2007).

Braak, H, Thal, D R, Ghebremedhin, E, et al., "Stages of the pathologic process in Alzheimer disease: age categories from 1 to 100 years," *J. Neuropathol. Exp. Neurol.*, 70:960-9 (2011).

Brandt, R, Leger, J, and Lee, G, "Interaction of tau with the neural plasma membrane mediated by tau's amino-terminal projection domain," *J. Cell Biol.*, 131(5):1327-40 (1995).

Brunden, K R, Trojanowski, J Q, and Lee, V M, "Evidence that non-fibrillar tau causes pathology linked to neurodegeneration and behavioral impairments," *J. Alzheimer's Disease*, 14(4):393-9 (2008).

Chirita, C N, Necula, M, and Kuret, J, "Anionic micelles and vesicles induce tau fibrillization in vitro," *J. Biol. Chem.*, 278(28):25644-50 (2003).

Chung, C W, et al., "Proapoptotic effects of tau cleavage product generated by caspase-3," *Neurobiol. Dis.*, 8(1):162-72 (2001).

Clavaguera, F, et al., "Transmission and spreading of tauopathy in transgenic mouse brain," *Nat. Cell Biol.*, 11(7): 909-13 (2009).

Congdon, E E, et al., "Nucleation-dependent tau filament formation: the importance of dimerization and an estimation of elementary rate constants," *J. Biol. Chem.*, 283(20): 13806-16 (2008).

Conrad, C et al., "Single molecule profiling of tau gene expression in Alzheimer's disease," *J. Neurochem.*, 103(3): 1228-36 (2007).

Davidowitz, E J, Chatterjee, I, and Moe, J G, "Targeting tau oligomers for therapeutic development for Alzheimer's disease and tauopathies," *Curr. Top. Biolechnol.*, 4:47-64 (2008).

de Calignon, A, Polydoro, M, Suarez-Calvet, M, et al., "Propagation of tau pathology in a model of early Alzheimer's disease," *Neuron*, 73:685-97 (2012).

Delobel, P, et al., "Analysis of tau phosphorylation and truncation in a mouse model of human tauopathy," *Am. J. Pathol.*, 172(1):123-31 (2008).

Deshpande, A, Win, K M, and Busciglio, J, "Tau isoform expression and regulation in human cortical neurons," *FASEB J.*, 22(7):2357-67 (2008).

Dubey, M, et al., "Tau inhibits anterograde axonal transport and perturbs stability in growing axonal neurites in part by displacing kinesin cargo: neurofilaments attenuate tau-mediated neurite instability," *Cell Motil. Cytoskeleton*, 65(2):89-99 (2008).

Fasulo, L, Ugolini, G, and Cattaneo, A. "Apoptotic effect of caspase-3 cleaved tau in hippocampal neurons and its potentiation by tau FTDP-mutation N279K," *J. Alzheimer's Dis.*, 7(1):3-13 (2005).

Fox, L M, William, C M, Adamowicz, D H, Pitstick, R, et al., "Soluble tau species, not neurofibrillary aggregates, disrupt neural system integration in a tau transgenic model," *J. Neuropathol. Exp. Neurol.*, 70:588-95 (2011).

Friedhoff, P, et al., "A nucleated assembly mechanism of Alzheimer paired helical filaments," *Proc. Natl. Acad. Sci. USA*, 95(26):15712-7 (1998).

Frost, B, et al., "Conformational diversity of wild-type Tau fibrils specified by templated conformation change," *J. Biol. Chem.*, 284(6):3546-51 (2009).

Gamblin, T C, et al., "Caspase cleavage of tau: linking amyloid and neurofibrillary tangles in Alzheimer's disease," *Proc. Natl. Acad. Sci. USA*, 100(17):10032-7 (2003).

Gendron, T F, and Petrucelli, L. "The role of tau in neurodegeneration," *Mol. Neurodegener.*, 4:13 (2009).

Ginsberg, S D, et al., "Shift in the ratio of three-repeat tau and four-repeat tau mRNAs in individual cholinergic basal forebrain neurons in mild cognitive impairment and Alzheimer's disease," *J. Neurochem.*, 96(5):1401-8 (2006).

Goedert, M, and Jakes, R. "Mutations causing neurodegenerative tauopathies," *Biochim. Biophys. Acta*, 1739(2-3): 240-50 (2005).

Gómez-Ramos, A, et al., "Extracellular tau is toxic to neuronal cells," *FEBS Lett.*, 580(20):4842-50 (2006).

Gómez-Ramos, A, et al., "Characteristics and consequences of muscarinic receptor activation by tau protein," *Eur. Neuropsychopharmacol.*, 19(10):708-717 (2009).

Gómez-Ramos, A, et al., "Extracellular tau promotes intracellular calcium increase through M1 and M3 muscarinic receptors in neuronal cells," Mol. Cell Neurosci., 37(4): 673-81 (2008).

Guillozet, A L, et al., "Neurofibrillary tangles, amyloid, and memory in aging and mild cognitive impairment," Arch. Neurol., 60(5):729-736 (2003).

Hanger, D P and Wray, S, "Tau cleavage and tau aggregation in neurodegenerative disease," Biochem. Soc. Trans., 38:1016-20 (2010).

Huang, Y, and Mucke, L, "Alzheimer mechanisms and therapeutic strategies," Cell, 148(6): 1204-22 (2012).

Iqbal K, et al., "Mechanisms of tau-induced neurodegeneration," Acta Neuropathol., 118(1):53-59 (2009).

Jeganathan, S, et al., "The natively unfolded character of tau and its aggregation to Alzheimer-like paired helical filaments," Biochemistry, 47(40):10526-39 (2008).

Josephs, K A, et al., "Beta-amyloid burden is not associated with rates of brain atrophy," Ann. Neurol., 63(2):204-12 (2008).

Kauwe, J S, et al., "Variation in MAPT is associated with cerebrospinal fluid tau levels in the presence of amyloid-beta deposition," Proc. Natl. Acad. Sci. USA, 105(23):8050-4 (2008).

Konzack, S, et al., "Swimming against the tide: mobility of the microtubule-associated protein tau in neurons," J. Neurosci., 27(37):9916-27 (2007).

Lasagna-Reeves, C A, Castillo-Carranza, D L, Sengupta, U, et al., "Tau oligomers impair memory and induce synaptic and mitochondrial dysfunction in wild-type mice," Mol. Neurodegener., 6:39 (2011).

Lasagna-Reeves, C A, Castillo-Carranza, D L, Sengupta, U, et al., "Identification of oligomers at early stages of tau aggregation in Alzheimer's disease," FASEB J., 26:1946-59 (2012).

Lee, G, Neve, R L, and Kosik K S, "The microtubule binding domain of tau protein," Neuron, 2(6):1615-24 (1989).

Leroy, K., et al., "Early axonopathy preceding neurofibrillary tangles in mutant tau transgenic mice," Am. J. Pathol., 171:976 (2007).

Liu, L, Drouet, V, Wu, J W, et al., "Trans-synaptic spread of tau pathology in vivo," PLoS One, 7(2):e31302 (2012).

Maas, T, Eidenmuller, J, and Brandt, R, "Interaction of tau with the neural membrane cortex is regulated by phosphorylation at sites that are modified in paired helical filaments," T. Biol. Chem., 275(21):15733-40 (2000).

Maeda, S, et al., "Granular tau oligomers as intermediates of tau filaments," Biochemistry, 46(12):3856-61 (2007).

Maeda, S, et al., "Increased levels of granular tau oligomers: an early sign of brain aging and Alzheimer's disease," Neurosci. Res., 54(3):197-201 (2006).

Mandelkow, E, et al., "Structural principles of tau and the paired helical filaments of Alzheimer's disease," Brain Pathol., 17(1):83-90 (2007).

Marx, J, "Alzheimer's disease. A new take on tau," Science, 316(5830):1416-7 (2007).

Matthews-Roberson, T A, et al., "Immortalized cortical neurons expressing caspase-cleaved tau are sensitized to endoplasmic reticulum stress induced cell death," Brain Res., 1234:206-12 (2008).

Mazanetz, M P, and Fischer, P M, "Untangling tau hyperphosphorylation in drug design for neurodegenerative diseases," Nat. Rev. Drug Discov., 6(6):464-79 (2007).

Mocanu, M M, et al., "The potential for beta-structure in the repeat domain of tau protein determines aggregation, synaptic decay, neuronal loss, and coassembly with endogenous Tau in inducible mouse models of tauopathy," J. Neurosci., 28(3):737-48 (2008).

Morris, M, Maeda, S, Vossel, K, et al., "The many faces of tau," Neuron, 70:410-26 (2011).

Mukrasch, M D, et al., "The "jaws" of the tau-microtubule interaction," J. Biol. Chem., 282(16):12230-9 (2007).

Myers, A J, et al., "The H1c haplotype at the MAPT locus is associated with Alzheimer's disease," Hum. Mol. Genet., 14(16):2399-404 (2005).

Needleman, S B and Wunsch, C D "A general method applicable to the search for similarities in the amino acid sequence of two proteins," J. Mol. Biol., 48(3):443-53 (1970).

Oddo, S, et al., "Reduction of soluble Aβ and tau, but not soluble Aβ alone, ameliorates cognitive decline in transgenic mice with plaques and tangles," Biol. Chem., 281: 39413 (2006).

Quintanilla, R A, et al., "Caspase-cleaved tau expression induces mitochondrial dysfunction in immortalized cortical neurons: implications for the pathogenesis of Alzheimer disease," J. Biol. Chem., 284(28):18754-66 (2009).

Rissman, R A, et al., "Caspase-cleavage of tau is an early event in Alzheimer disease tangle pathology," J. Clin. Invest., 114(1):121-30 (2004).

Roberson, E D, "Reducing endogenous tau ameliorates amyloid β-induced deficits in an Alzheimer's disease mouse model," Science, 316(5825):750-4 (2007).

Rocher, A B, Crimins, J L, Amatrudo, J M, et al., "Structural and functional changes in tau mutant mice neurons are not linked to the presence of NFTs," Exp. Neurol., 223(2):385-393 (2009).

Sahara, N, et al., "Assembly of two distinct dimers and higher-order oligomers from full-length tau," Eur. J. Neurosci., 25(10):3020-9 (2007).

Sahara, N, Maeda, S, and Takashima, A. "Tau oligomerization: a role for tau aggregation intermediates linked to neurodegeneration," Curr. Alzheimer Res., 5(6):591-8 (2008).

Santacruz, K, "Tau suppression in a neurodegenerative mouse model improves memory function," Science, 309 (5733):476-81 (2005).

Schonheit, B, Zarski, R, and Ohm, T G, "Spatial and temporal relationships between plaques and tangles in Alzheimer-pathology," Neurobiol. Aging, 25(6):697-711 (2004).

Schweers, O, et al., "Oxidation of cysteine-322 in the repeat domain of microtubule-associated protein tau controls the in vitro assembly of paired helical filaments," Proc. Natl. Acad. Sci. USA, 92(18):8463-7 (1995).

Seabrook, G R, et al., "Beyond amyloid: the next generation of Alzheimer's disease therapeutics," Mol. Interv., 7(5): 261-70 (2007).

Sennvik, K, et al., "Tau-4R suppresses proliferation and promotes neuronal differentiation in the hippocampus of tau knockin/knockout mice," FASEB J., 21(9):2149-61 (2007).

Shaw, L M, et al., "Alzheimer's disease neuroimaging initiative. cerebrospinal fluid biomarker signature in Alzheimer's disease neuroimaging initiative subjects," Ann. Neurol., 65(4):403-413 (2009).

Sigurdsson, E M, "Tau-focused immunotherapy for Alzheimer's disease and related tauopathies," Curr. Alzheimer Res., 6(5):446-50 (2009).

Spires, T L, et al., "Region-specific dissociation of neuronal loss and neurofibrillary pathology in a mouse model of tauopathy," Am. J. Pathol., 168:1598 (2006).

Spires-Jones, T L, et al., "In vivo imaging reveals dissociation between caspase activation and acute neuronal death in tangle-bearing neurons," *J. Neurosci.*, 28(4):862-7 (2008).

Sugino, E, et al., "Three-/four-repeat-dependent aggregation profile of tau microtubule-binding domain clarified by dynamic light scattering analysis," *Biochem. Biophys. Res. Commun.*, 385(2):236-40 (2009).

Tobin, J E, et al., "Haplotypes and gene expression implicate the MAPT region for Parkinson disease: the GenePD Study," *Neurology*, 71(1):28-34 (2008).

Turgeon, V, and Houenou, L, "The role of thrombin-like serine proteases in the development, plasticity and pathology of the nervous system," *Brain Res. Rev.*, 25:85-95 (1997).

von Bergen, M, et al., "Assembly of tau protein into Alzheimer paired helical filaments depends on a local sequence motif ((306)VQIVYK(311)) forming beta structure," *Proc. Natl. Acad. Sci. USA*, 97(10):5129-34 (2000).

Wang, J Z, and Liu, F, "Microtubule-associated protein tau in development, degeneration and protection of neurons," *Prog. Neurobiol.*, 85(2):148-75 (2008).

Wang, Y, Garg, S, Mandelkow, E M, et al., "Proteolytic processing of tau," *Biochem. Soc. Trans.*, 38:955-61 (2010).

Wang, Y, et al., "Tau fragmentation, aggregation and clearance: the dual role of lysosomal processing," *HMG Adv. Acc.*, 18(21):4153-4170 (2009).

Wilson, D M, and Binder, L I, "Free fatty acids stimulate the polymerization of tau and amyloid beta peptides. In vitro evidence for a common effector of pathogenesis in Alzheimer's disease," *Am. J. Pathol.*, 150(6):2181-95 (1997).

Xu, S, "Aggregation drives 'misfolding' in protein amyloid fiber formation," *Amyloid*, 14(2):119-31 (2007).

Yoshiyama, Y, et al., "Synapse loss and microglial activation precede tangles in a P301S tauopathy mouse model," *Neuron*, 53(3):337-51 (2007).

Zhang, Q, et al., "Role of caspase-3 in tau truncation at D421 is restricted in transgenic mouse models for tauopathies," *J. Neurochem.*, 109(2):476-84 (2009).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated truncated tau peptide or polypeptide of 50 to 300 amino acids in length, comprising an amino acid sequence that is at least 98% identical to an at least 50-amino acid contiguous sequence from SEQ ID NO:6, and the amino acid sequence is SEQ ID NO:6, wherein the isolated truncated tau peptide or polypeptide is configured to be a drug target, and the isolated truncated tau peptide or polypeptide comprises enhanced or diminished serine protease activity when compared to that of a naturally occurring tau peptide or a naturally occurring tau polypeptide; and the peptide or polypeptide comprises at least one substitution at a position that corresponds to amino acid residue 5, 257, 260, 266, 272, 273, 279, 280, 296, 301, 303, 304, 315, 317, 332, 335, 336, 337, 342, 363, 369, 389, 406 or 427 of SEQ ID NO:6, and the isolated truncated tau peptide or polypeptide is expressed in a bacterial host cell.

2. The isolated truncated tau peptide or polypeptide according to claim 1, comprising an amino acid sequence that is at least 98% identical to an at least 80-amino acid contiguous sequence from SEQ ID NO:6.

3. The isolated truncated tau peptide or polypeptide according to claim 1, comprising an amino acid sequence that is at least 99% identical to an at least 90-amino acid contiguous sequence from SEQ ID NO:6.

4. The isolated truncated tau peptide or polypeptide according to claims 1, of 70 to 250 amino acids in length.

5. The isolated truncated tau peptide or polypeptide according to claims 1, of 80 to 220 amino acids in length.

6. The isolated truncated tau peptide or polypeptide according to claims 1, of 100 to 210 amino acids in length.

7. The isolated truncated tau peptide or polypeptide according to claim 1, wherein the peptide has a serine protease activity that is at least 85% of that of the full-length Tau 4R2N trimer protease.

8. The isolated truncated tau peptide or polypeptide according to claim 1, wherein the peptide has a serine protease activity that is at least 95% of that of the full-length Tau 4R2N trimer protease.

9. The isolated truncated tau peptide or polypeptide according to claim 1, wherein the isolated truncated tau peptide or polypeptide is an oligomer having protease activity or is a fragment containing a cleavage site for tau protease.

10. A truncated tau protease variant peptide or polypeptide comprising an amino acid sequence of a starting mammalian tau protease that has been substituted in at least one amino acid at a position that corresponds to amino acid residue 5, 257, 260, 266, 272, 273, 279, 280, 285, 296, 301, 303, 304, 305, 315, 317, 320, 332, 335, 336, 337, 342, 352, 356, 363, 369, 389, 406, or 427 of SEQ ID NO:6, wherein the substitution confers to the truncated protease variant peptide or polypeptide an enhanced serine protease activity, when compared to that of the original, un-substituted tau protease peptide or polypeptide, and the amino acid sequence is SEQ ID NO:6, and the truncated tau protease variant peptide or polypeptide is expressed in a bacterial host cell.

11. The truncated tau protease variant peptide or polypeptide according to claim 10, wherein the one or more amino acid substitutions is an arginine-to-histidine substitution, an arginine-to-leucine substitution, an arginine-to-tryptophan substitution, an asparagine-to-alanine substitution, an asparagine-to-histidine substitution, an asparagine-to-lysine substitution, a glutamate-to-valine substitution, a glutamine- to-arginine substitution, a glycine-to-arginine substitution, a glycine-to-serine substitution, a glycine-to-valine substitution, an isoleucine-to-valine substitution, a leucine-to-arginine substitution, a leucine-to-valine substitution, a lysine-to- isoleucine substitution, a lysine-to-methionine substitution, a lysine-to-threonine substitution, a proline-to-leucine substitution, a proline-to- serine substitution, a proline-to-threonine substitution, a serine-to-asparagine substitution, a serine-to- isoleucine substitution, a serine-to-leucine substitution, a serine-to-phenalanine substitution, a threonine-to-methionine substitution, a valine-to-isoleucine substitution, a valine-to-methionine substitution, or any combination thereof.

12. The truncated tau protease variant peptide or polypeptide according to claim 10, wherein the one or more amino acid substitutions is an R5H substitution, an R5L substitution, a K257T substitution, a 1260V substitution, a L266V substitution, a G272V substitution, a G273R substitution, a N279K substitution, a L284V substitution, a N296A substitution, a N296H substitution, a P301L substitution, a P301S substitution, a P301T substitution, a G303V substitution, a G304S substitution, a S305I substitution, a S305N substitution, a L315R substitution, a K317M substitution, a S320F substitution, a P332S substitution, a G335S substitution, a G335V substitution, a Q336R substitution, a V337M substitution, an E342V substitution, a S352L substitution, a S356T substitution, a V363I substitution, a K369I substitution, a G389R substitution, a R406W substitution, a T427M substitution, or any combination thereof.

13. The truncated tau protease variant peptide or polypeptide according to claim 10, wherein the variant has a serine protease activity that is at least 85% of that of the full-length Tau 4R2N trimer protease.

14. The truncated tau protease variant peptide or polypeptide according to claim 10, wherein the variant has a serine protease activity that is at least 95% of that of the full-length Tau 4R2N trimer protease.

15. An isolated truncated tau peptide or polypeptide of 50 to 300 amino acids in length comprising an at least 40 contiguous amino acid sequence from SEQ ID NO:6, and that has been mutated at one or more amino acids that correspond to amino acid residue 5, 257, 260, 266, 272, 273, 279, 280, 285, 296, 301, 303, 304, 305, 315, 317, 320, 332, 335, 336, 337, 342, 352, 356, 363, 369, 389, 406, or 427 of SEQ ID NO:6, wherein the truncated tau peptide or polypeptide has a serine protease activity that is at least 85% of that of the full-length Tau 4R2N trimer protease, and the isolated truncated tau peptide or polypeptide is expressed in a bacterial host cell.

16. The isolated truncated tau peptide or polypeptide according to claims 15, of 70 to 220 amino acids in length comprising an at least 50 contiguous amino acid sequence from any one of SEQ ID NO: 1, SEQ ID NO;2, SEQ ID NO:3, SEQ ID NO:4, or SEQ ID NO:5, and that has been mutated at one or more amino acids corresponding to one or more of amino acid residues 5, 257, 260, 266, 272, 273, 279, 280, 285, 296, 301, 303, 304, 305, 315, 317, 320, 332, 335, 336, 337, 342, 352, 356, 363, 369, 389, 406, or 427 of SEQ ID NO:6, wherein the truncated tau peptide or polypeptide has a serine protease activity that is at least 70% of that of the full-length Tau 4R2N trimer protease.

* * * * *